United States Patent [19]
Gerald et al.

[11] Patent Number: 5,968,819
[45] Date of Patent: *Oct. 19, 1999

[54] DNA ENCODING A HYPOTHALAMIC ATYPICAL NEUROPEPTIDE Y/PEPTIDE YY RECEPTOR (Y5)

[75] Inventors: Christophe P. G. Gerald, Ridgewood; Richard L. Weinshank, Teaneck; Mary W. Walker, Elmwood Park; Theresa Branchek, Teaneck, all of N.J.

[73] Assignee: Synaptic Pharmaceutical Corporation, Paramus, N.J.

[*] Notice: This patent is subject to a terminal disclaimer.

[21] Appl. No.: 08/566,096

[22] Filed: Dec. 1, 1995

Related U.S. Application Data

[63] Continuation-in-part of application No. 08/349,025, Dec. 2, 1994, Pat. No. 5,602,024.

[51] Int. Cl.$^6$ .......................... C07H 21/00; C12N 15/12; C12N 15/63; C12N 5/10
[52] U.S. Cl. ........................ 435/325; 435/320.1; 536/23.5
[58] Field of Search ................................ 435/325, 320.1, 435/69.1, 252.3, 254.2, 348, 365, 369; 536/23.1, 23.5

[56] References Cited

U.S. PATENT DOCUMENTS

| | | |
|---|---|---|
| 5,516,653 | 5/1996 | Bard et al. |
| 5,545,549 | 8/1996 | Gerald et al. |
| 5,602,024 | 2/1997 | Gerald et al. |

FOREIGN PATENT DOCUMENTS

| | | |
|---|---|---|
| 2-037433 | 10/1991 | Canada . |
| 9309227 | 5/1993 | WIPO . |
| 9324515 | 12/1993 | WIPO . |
| 9517906 | 7/1995 | WIPO . |
| 9521245 | 8/1995 | WIPO . |
| 9614331 | 5/1996 | WIPO . |
| 9616542 | 6/1996 | WIPO . |
| 9623809 | 8/1996 | WIPO . |
| WO9717440 | 5/1997 | WIPO . |

OTHER PUBLICATIONS

Kalra, S.P. et al., Physiology & Behavior. 50:5–9, (1991).
Krause, J., et al. Molecular Pharmaceology. 41:817–821, (1992).
Larhammar, D., et al. J. Biol. Chem. 267(16):10935–10938, (1992).
Stanley, B.G., et al. Peptides. 13:581–587, (1992).
Balasubramaniam, A., et al. J. Med. Chem. 37:811–815, (1994).
Ball, H.J., et al. J. Biol. Chem. 270(45):27272–27276, (1995).
Gerald, C. et al., Letters To Nature. 382:168–171, (1996).
Weinberg, D.H. et al., J. Biol. Chem. 271(28):16435–16438, (1996).
George et al. Biochem. Biophys. Res. Comm., vol. 163, pp. 1265–1269, 1989.
Gehlert, D.R., "Subtype of Receptor For Neuopeptides Y: Implications For The Targeting", of Therapeutics, *Life Science* (1994) 55: 551–562 (Exhibit E).
Herzog, et al., "Cloned Human Neuropeptide Y Receptor Couples to Two Different Second Messenger Systems", *Proc. Natl. Acad. Sci. USA* (1992) 89: 5794–5798 (Exhibit F).
Wahlestedt, et al., "Identification of Cultured Cells Selectively Expressing Y1–, Y2–, or Y3– Type Receptor For Neuropides Y/Peptide YY" *Life Science* (1991) 50: PL 7–12 (Exhibit G).
Hu, Y. et al., Journal of Biol. Chem. 271: 26315–26319 (1996).

Primary Examiner—Patricia Duffy
Assistant Examiner—Stephen Gucker
Attorney, Agent, or Firm—John P. White; Cooper & Dunham Llp

[57] ABSTRACT

This invention provides methods of modifying feeding behavior, including increasing or decreasing food consumption, e.g., in connection with treating obesity, bulimia or anorexia. These methods involve administration of compounds are selective agonists or antagonists or the Y5 receptor. One such compound has the structure:

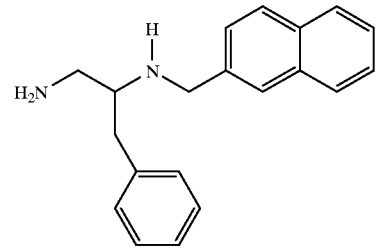

In addition, this invention provides an isolated nucleic acid molecule encoding a Y5 receptor, an isolated Y5 receptor protein, vectors comprising an isolated nucleic acid molecule encoding a Y5 receptor, cells comprising such vectors, antibodies directed to the Y5 receptor, nucleic acid probes useful for detecting nucleic acid encoding Y5 receptors, antisense oligonucleotides complementary to any unique sequences of a nucleic acid molecule which encodes a Y5 receptor, and nonhuman transgenic animals which express DNA a normal or a mutant Y5 receptor.

22 Claims, 40 Drawing Sheets

FIGURE 3

```
1    TTAGTTTGTTCTGAGAACGTTAGAGAGTTATAGTACCGTGCGATCGTGTTCTTCAAGCTGCTA      60
61   ATGGACGTCCTCTTCTTCCACCAGAGGATTCTAGTATGGGAGTTTAAGCTTGAGGAGCATTTT     120
121  AACAAGACATTGTCACAGAGAACAATACAGCTGCTCGGAATGCAGCCTTCCCTGCC            180
181  TGGGAGGACTACAGAGGCAGCGTAGACGATTTACAATACTTTCTGATTGGCTCTATACA         240
241  TTCGTAAGTCTCTTGCTTTATGGGCAATCTACTTATTTTAATGGCTGTTATGAAAAAG          300
301  CGCAATCAGAAGACTACAGTGAACTTTCTCATAGGCAACCTGGCTTCTCCGACATCTTG         360
361  GTCGTCCTGTTTGCTCCCCTTTCACCCTGACCCTCTGTCTTGTTGGATCAGTGGATGTTT        420
421  GGCAAAGCCATGTGCCATATCATGCCATTGTCAGGTATCATGTGTCAGTTCTGGTTTCAACT      480
481  CTGATTTTAATATCGCAAACCATGGCTACTTCCTGACAGTCTTGTGAACTTAAGGAGACCCTATTCTAAC 540
541  AATTTAACGGCAAACCATGGCTACTTCCTGACAGTCTGTCTGGAACTGTCTGGACACTGGGCTTTGCC   600
601  ATCTGTTCTCCCCTCCCCAGTGTTCCACAGTCTTGTGAACTTAAGGAGACCTTTGGCTCA        660
661  GCACTGCTGAGTAGCAAATATCTCTGTGTTGCAGTAGTGCAGTATATCCTGCCTCTGATTCATACAGAATT 720
721  GCTTTCACAATCTCTTTATGCTAGTGCAGTATATCCTGCCTCTAGTATGTTAACGGTA         780
781  AGTCATACCAGCGTCTGCCGAAGCATAAGCTGTGGATTGTCCCACAAAGAAAACAGACTC       840
841  GAAGAAATGAGATGATCAACTTAACCCTACAGCCATCCAAAAGAGCAGGAACCAGGCA        900
901  AAACCCCCAGCACTCAAAAGTGGAGCTACTCATTCATCAGAAAGCACACAGAAGGAGGTAC     960
961  AGCAAGAAGACGGCCTGTCTTACCCGCCCAGCAGGACCTTCCCAGGGGAAGCACCTA         1020
1021 GCCGTTCCAGAAATCCAGCCTCCGTCCGTAGCAACCTGCTGCCATCCAGTAAGGTCATT     1080
1081 CCAGGGTCCCAATCTGCTTTGAGGTGAAACCTCAGATGCTCATGAGATG              1140
1141 AGAGTCAAGCGTTCCATCACTAGAATAAAAAGAGATCTCGAAGTGTTTTCTACAGACTG      1200
1201 ACCATACTGATATCGTTCGCCGTTAGCTGGATGCCACTCCACGTCTTCCACGTGGTG       1260
1261 ACTGACTTCAATGATAACTTGATTTCCAATAGGCATTTCAAGCTGGTATACTGCATCTGT     1320
1321 CACTTGTTAGGCATGATGTCCTGTTGTCTAAATCCGATCCTATATGGTTTCCTTAATAAT     1380
1381 GGTATCAAAGCAGACTTGAGAGAAACGTGGTAATTGACACACATAATTTATACAGAAGTATTCTCTG     1440
1441 TGCACCAAAGAGAGAAGAAACGTGGTAATTGACACACATAATTTATACAGAAGTATTCTGGAT    1501
```

```
   1 GTTCCCTCTGAATAGATTAATTAAAGTAGTCATGTAATGTTTTTTGGTTGCTGACAA         60
  61 ATGTCTTTTATTCCAAGCAGGACTATAATATGGATTAGAGCTCGACGAGTATTATAAC        120
 121 AAGACACTTGCCACACAGAGAATAATACTGCTGCCACTCGGAATTCTGATTTCCCAGTCTGG    180
 181 GATGACTATAAAAGCAGTGTAGATGACTTACAGTATTTCTGATTGGGCTCTATACATTT       240
 241 GTAAGTCTCTTGGCTTTATGGGAATCTCTATTTTAATGGCCTTTCTGATATCTTGGTT        300
 301 AATCAGAAGACTACGGTAAACTTCCTCATAGGCAATCTGGCCTTTCTGATATCTTGGTT       360
 361 GTGCTGTTTTGCTCACCTTTCACACTGCCTCTCTGTCTTGCTGGATCAGTGGATGTTTGGC     420
 421 AAAGTCATGTGCCATATTATGCCTTTTCTCAATGTGTCAGTTTTGGTTTCAACTTTA         480
 481 ATTTTAATATCAATTGCCATTGTCAGGTATCATATGATAAAACATCCCATATCTAATAAT     540
 541 TTAACAGCAAACCATGGCTACTTTCTGATAGCTACTGTCTGGACACTAGGTTTTGCCATC      600
 601 TGTTCTCCCCTTCCAGTGTTTCACAGTCTTGTGAGTCTTGTTCAAGAACATTGGTTCAGCA     660
 661 TTGCTGAGCAGCAGGTATTTATGTGTCAGTATATTCTGCCCCTTAGTTTGTCTTACTGTAAGT   720
 721 TTTACTATCTCTTTATTGCTAGAAGTATAACTTCTGTCCAACAAAGAAAACAGACTTGAA      780
 781 CATACAAGTGTCTGCAGAAGTATAAGCTGTGGATTGTCCAACAAAGAAAACAGACTTGAA      840
 841 GAAAATGAGAGATGATCAACTAAAATGGAGTTATTCATTCATCAAAAGACCTTCAGGTGAAA    900
 901 CTCTCTGGCCAGCAGCATCATCTGGAATTACCTGCTCTGTTACCTGTGAAGAGATATAGC      960
 961 AAGAAGACAGCAGCATGTGTGTTGGCTCTGTTGAGATAAACCTGAGCTCTCTCTTCATCCAGA  1020
1021 ATACTTCCAGAAAACTTTGGCTCTTGCTTTGAGATAAACCTGAGCTCAGATGTTCATGAATTG  1080
1081 CCAGGGTCCCACTTCTGTTACAAGATAAAATAAAAGATCTCGAAGTGTTTCTACAGACTG     1140
1141 AGAGTAAAACGTTCTGTTACAAGAGATCTCGAAGTGTTTCTACAGACTG                1200
1201 ACCATACTGATATTAGTATTTGCTGTTAGTGGATGCCACTACACCTTTCCATGTGGTA       1260
1261 ACTGATTTTAATGACAATCTTATTCAAATAGGCATTTCAAGTTGGTGTATTGCATTTGT     1320
1321 CATTTGTTGGGCATGATGTCCTGTTGTCTTAATCACTGTCTTATATGGTTTCTTAATAAT    1380
1381 GGGATTAAAGCTGATTAGTGTCCCTTATACACTGTCTTCATATGTAATAATTCTCACTG    1440
1441 TTTACCAAGGAAAGAAC                                                1457
```

| FIGURE 7A |
|---|
| FIGURE 7B |
| FIGURE 7C |
| FIGURE 7D |
| FIGURE 7E |

```
  1  ATGGACGTCCTCTTCTTCC.ACCAGGATTCTAGTATGGAGTTTAAGCTTG   50
  1  ....ATGTCTTTTTATTCCAAGCAGGACTATAATATGGATTTAGAGCTCG   46

51  AGGAGCATTTTAACAAGACATTTGTCACAGAGAACAATACAGCTGCTGCT  100
 47  ACGAGTATTATAACAAGACACTTGCCACAGAGAATAATACTGCTGCCACT   96

101  CGGAATGCAGCCCTTCCCTGCCTGGGAGGACTACAGAGGCAGCGTAGACGA  150
 97  CGGAATTCTGATTCCCAGTCTGGGATGACTATAAAAGCAGTGTAGATGA  146

151  TTTACAATACTTTCTGATTGGGCTCTATACATTCGTAAGTCTTCTTGGCT  200
147  CTTACAGTATTTTCTGATTGGGCTCTATACATTGTAAGTCTTCTTGGCT  196

201  TTATGGGCAATCTACTTATTTTAATGGCTGTTATGAAAAAGCGCAATCAG  250
197  TTATGGGGAATCTACTTATTTTAATGGCTCTCATGAAAAAGCGTAATCAG  246
```

FIGURE 7B

```
251 AAGACTACAGTGAACTTTCTCATAGGCAACCTGGCCTTCTCCGACATCTT 300
    ------------------------------------------------
247 AAGACTACGGTAAACTTCCTCATAGGCAATCTGGCCTTTCTGATATCTT 296

301 GGTCGTCCTGTTTGCTCCCCTTTCACCCTGACCTCTGTCTGTTGGATC 350
    ------------------------------------------------
297 GGTTGTGCTGTTTGCTCACCTTTGCTCACACTGAGTCTGTCTTGCTGGATC 346

351 AGTGGATGTTTGGCAAAGCCATGTGCCATATCATGCCGTTCCTTCAATGT 400
    ------------------------------------------------
347 AGTGGATGTTTGGCAAAGTCATGTGCCATATTATGCCTTTTCTTCAATGT 396

401 GTGTCAGTTCTGGTTTCAACTCTGATTTTAATATCAATTGCCATTGTCAG 450
    ------------------------------------------------
397 GTGTCAGTTTTGGTTTCAACTTTAATTTTAATATCAATTGCCATTGTCAG 446

451 GTATCATATGATAAAGCACCCTATTTCTAACAATTTAACGGCAAACCATG 500
    ------------------------------------------------
447 GTATCATATGATAAAACATCCCATATCTAATAATTTAACAGCAAACCATG 496

501 GCTACTTCCTGATAGCTACTGTGTCTGGACACTGGGCTTTGCCATCTGTTCT 550
    ------------------------------------------------
497 GCTACTTTCTGATAGCTACTGTGTCTGGACACTAGGTTTTGCCATCTGTTCT 546
```

FIGURE 7C

```
551 CCCCTCCCAGTGTTTCACAGTCTTGTGGAACTTAAGGAGACCTTTGGCTC  600
547 CCCCTTCCAGTGTTTCACAGTCTTGTGGAACTTCAAGAAACATTTGGTTC  596

601 AGCACTGCTGAGTAGCAAATATCTCTGTGTTGAGTCATGGCCCTCTGATT  650
597 AGCATTGCTGAGCAGCAGGTATTTATGTGTTGAGTCATGGCCATCTGATT  646

651 CATACAGAATTGCTTTCACAATCTCTTTATTGCTAGTGCAGTATATCCTG  700
647 CATACAGAATTGCCTTTACTATCTCTTTATTGCTAGTTCAGTATATTCTG  696

701 CCTCTAGTATGTTTAACGGTAAGTCATACCAGCGTCTGCCGAAGCATAAG  750
697 CCCTTAGTTTCTTACTGTAAGTCATACAAGTGTCTGCAGAAGTATAAG   746

751 CTGTGGATTGTCCCACAAAGAAAACAGACTCGAAGAAAATGAGATGATCA  800
747 CTGTGGATTGTCCAACAAAGAAAACAGACTTGAAGAAAATGAGATGATCA  796

801 ACTTAACCCTACAGCCATCCAAAAAGAGAGCAGGAACCAGGCAAAACCCCC  850
797 ACTTAACTCTTCATCCATCCAAAAAGAGAGTGGGCCTCAGGTGAAACTCTCT  846
```

FIGURE 7D

```
 851 AGCACTCAAAAGTGGAGCTACTCATTCATTCAGAAAGCACAGAAGGAGTA  900
 847 GGCAGCCATAAATGGAGTTATTCATTCATCAAAAACACAGAAGAAGATA   896
 901 CAGCAAGAAGACGGCCTGTGTCTTACCCGCCCCAGCAGGACCTTCCCAGG  950
 897 TAGCAAGAAGACAGCATGTGTGTTACCTGCTCCAGAAAGACCTTCTCAAG  946
 951 GGAAGCA...CCTAGCCGTTCCAGAAAATCCAGCCTCCGTCCGTAGCCAG 1000
 947 AGAACCACTCCAGAATACTTCCAGAAAACTTTGGCTCTGTAAGAAGTCAG  996
1001 CTGTCGCCATCCAGTAAGGTCATTCCAGGGGTCCCAATCTGCTTTGAGGT 1050
 997 CTCTCTTCATCCAGTAAGTTCATACCAGGGGTCCCCACTTGCTTTGAGAT 1046
1051 GAAACCTGAAGAAGCTCAGATGCTCATGAGATGAGAGTCAAGCGTTCCA  1100
1047 AAAACCTGAAGAGAAATTCAGATGTTCATGAATTGAGAGTAAAACGTTCTG 1096
1101 TCACTAGAATAAAAAGAGATCTCGAAGTGTTTTCTACAGACTGACCATA  1150
1097 TTACAAGAATAAAAAGAGATCTCGAAGTGTTTTCTACAGACTGACCATA  1146
```

FIGURE 7E

```
1151 CTGATACTCGTGTTCGCCGTTAGCTGGATGCCACTCCACGTCTTCCACGT 1200
        ||  | ||  | || | ||||  |||||||||||  ||| ||||||||
1147 CTGATATTAGTATTTGCTGTGTTAGTTGGATGCCACTACACCTTTTCCATGT 1196

1201 GGTGACTGACTTCAATGATAACTTGATTTCCAATAGGCATTTCAAGCTGG 1250
      |||| |||| || ||||||  |||||| || ||||||||||||||||| ||
1197 GGTAACTGATTTTAATGACAATCTTATTTCAAAATAGGCATTTCAAGTTGG 1246

1251 TATACTGCATCTGTCACTTGTTAGGCATGATGTCCTGTTGTCTAAATCCG 1300
      | |||||||| ||| ||||||| ||||||||||||||  ||||||| |||
1247 TGTATTGCATTTGTCATTTGTTGGGCATGATGTCCTGTTGTCTTAATCCA 1296

1301 ATCCTATATGGTTTCCTTAATAATGGTATCAAAGCAGACTTGAGAGCCCT 1350
      |  |||||| ||| |||||||| |||  |||||  | |||||  ||| ||
1297 ATTCTATATGGGTTTCTTAATAATGGGATTAAAGCTGATTTAGTGTCCCT 1346

1351 TATCCACTGCCTACACACATGTCA 1372
      ||  |||||  |||||||||||
1347 TATACACTGTCTCTTCATATG.... 1365
```

FIGURE 7F

| FIGURE 7F |
|-----------|
| FIGURE 7G |

```
  1 MDVLFFHQDSSMEFKLEEHFNKTFVTENNTAAARNAAFPAWEDYRGSVDD          50
    ::               ::  :: :  :  :.  :: :: :: 
  1 .MSFYSKQDYNMDLELDEYYNKTLATENNTAATRNSDFPVWDDYKSSVDD          49
                                        II
 51 LQYFLIGLYTFVSLLGFMGNLLILMAVMKKRNQKTTVNFLIGNLAFSDIL         100
    LQYFLIGLYTFVSLLGFMGNLLILMALMKKRNQKTTVNFLIGNLAFSDIL
 50 LQYFLIGLYTFVSLLGFMGNLLILMALMKKRNQKTTVNFLIGNLAFSDIL          99
          I                                III
101 VVLFCSPFTLTSVLLDQWMFGKAMCHIMPFLQCVSVLVSTLILISIAIVR         150
    VVLFCSPFTLTSVLLDQWMFGKVMCHIMPFLQCVSVLVSTLILISIAIVR
100 VVLFCSPFTLTSVLLDQWMFGKVMCHIMPFLQCVSVLVSTLILISIAIVR         149
                          IV
151 YHMIKHPISNNLTANHGYFLIATVWTLGFAICSPLPVFHSLVELKETFGS         200
    YHMIKHPISNNLTANHGYFLIATVWTLGFAICSPLPVFHSLVELQETFGS
150 YHMIKHPISNNLTANHGYFLIATVWTLGFAICSPLPVFHSLVELQETFGS         199
```

FIGURE 7G

```
                                           V
201 ALLSSKYLCVESWPSDSYRIAFTISLLLVQYILPLVCLTVSHTSVCRSIS           250
    ---------------:----------------------------------
200 ALLSSRYLCVESWPSDSYRIAFTISLLLVQYILPLVCLTVSHTSVCRSIS           249
    ---:------------------------------------------:---
251 CGLSHKENRLEENEMINLTLQPSKKSRNQAKTPSTQKWSYSFIRKHRRRY           300
    ---:--------------:-----:-:-------:----:--:-------
250 CGLSNKENRLEENEMINLTLHPSKKSGPQVKLSGSHKWSYSFIKKHRRRY           299
    ----------------:-----:-:------:-:-:-:-:---:-:----
301 SKKTACVLPAPAGPSQGKHLAV.PENPASVRSQLSPSSKVIPGVPICFEV           349
    ----------------:-:-----:----------:------:---:-:-
                                                    VI
300 SKKTACVLPAPERPSQENHSRILPENFGSVRSQLSSSSKFIPGVPTCFEI           349
    ----------:--:--:-:--:-:----------:---------------
350 KPEESSDAHEMRVKRSITRIKKKRSRSVFYRLTILILVFAVSWMPLHVFHV           399
    -----:-:---:----:-----:---------------------:-:---
                          VII
350 KPEENSDVHELRVKRSVTRIKKRSRSVFYRLTILILVFAVSWMPLHLFHV           399
    --------------:--------:--:--:--------------------
400 VTDFNDNLISNRHFKLVYCICHLLGMMSCCLNPILYGFLNNGIKADLRAL           449
    -----------------:--------------------------------
400 VTDFNDNLISNRHFKLVYCICHLLGMMSCCLNPILYGFLNNGIKADLVSL           449

450 IHCLHMS  456
    -------
450 IHCLHM.  455
```

FIGURE 8A

| | FIGURE 8A |
|---|---|
| | FIGURE 8B |
| | FIGURE 8C |

FIGURE 8B

```
                                                                    V
                                                        ┌─────────────────────────────────┐
Y5h  LLS...SRYLCVESUPSD...S.YRIAFTISLLVQYILPLVCLTVSHTSV              244
Y1h  D.AYK.DKYVCFFDQFPSD...S.HRLSYTTLLVLQYFGPLCFIFICYFKI             234
Y2h  IVA....CTEKUPGEEKSIYGTVYSLSSLLILYVLPLGIISFSYTRI                 242
Y4h  ALEFLADKVVCTESUP-..LAHHRTIYTTFLLLFQYCLPLGFILVCYARI              237

Y5h  CRSISCGLSNKENRLEENEMINLTLHPSKKSGPQVKLSGSHKWSYSFIKK              294
Y1h  ..............................................YI               236
Y2h  ..........................................WSKLKN               248
Y4h  ..............................................YR               239

Y5h  HRRYSKKTACVLPAPERPSQENHSRILPENFGSVRSQLSSSSKFIPGVP              344
Y1h  RLKRRNNMDKHRDNKYRSSE...........................                 257
Y2h  HVSPGAANDHYHQRRQK-.GH..........................                 265
Y4h  RLQRQGRVFHK-GTYSLRAGH..........................                 259
                                                        VI
                                                        ┌──────────────────────────┐
Y5h  TCFEIKPEENSDVHELRVKRSVTRIKKRSRSVFYRLTILILVFAVSWMPL              394
Y1h  ............................TKRINIMLLSIVVAFAVCWLPL              279
Y2h  ..............................TTKMLVCVVVFAVSWLPL               284
Y4h  ............MKQVNVVLVVMVVAFAVLWLPL                              281
```

FIGURE 8C

```
                                           |─────────── VII ───────────|
Y5h   HLFHVVTD-FNDNLISNRHFKLVYCICHLLGMMSCCLNPILYGFLNNGIKA       444
Y1h   TIFNTVFD-WNHQIIATCNNLLCNLTAMISTCVNPIFYGFLNKNFQR K         329
Y2h   HAFQLAVDIDSQVLDLKEYKLIFTVFMIAMCSTFAMPLLYGWHMSNYRK          334
Y4h   HVFNSLEDWHHEAIPICHGNLIFLVCHLLAMASTCVNPFIYGFLNTNFKK         331

Y5h   DLVSLIH-CLHM------SRDDDYETIAMSTMHTDVSKTISLKQASPVAFKKINND-     455
Y1h   DLQFFNFCDFRSRDDDYETIAMSTMHTDVSKTISLKQASPVAFKKINND-         379
Y2h   AFLSAFR-CEQRLDAIHSEVSVTFKAKKNLEVRKNSGPNDSFTEATNV--         381
Y4h   EIKALVLTCQQSAPLEESEHLPLSTVHTEVSKGSLRLSGRSNPI-----          375

Y5h   -----       455
Y1h   DNEKI       384
Y2h   -----       365
Y4h   -----       375
```

FIGURE 13A  Silver grain density:
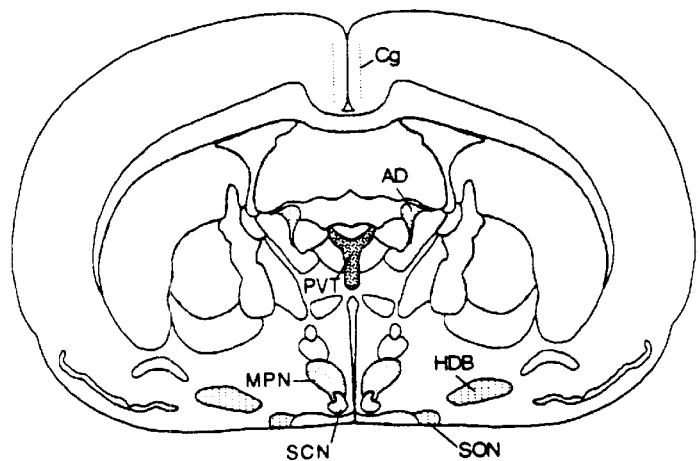
FIGURE 13B
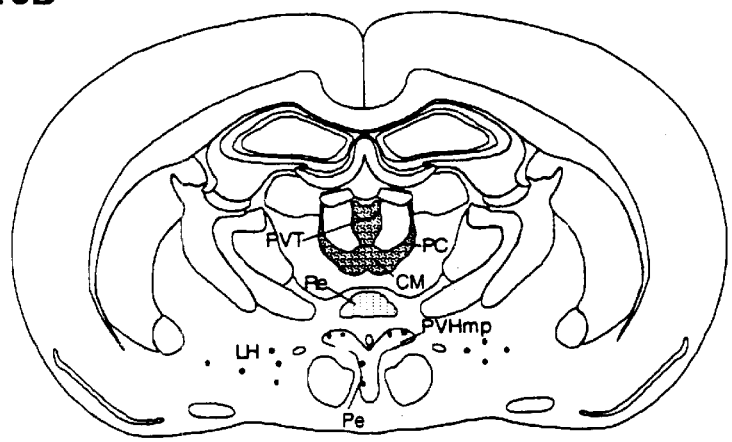
FIGURE 13C
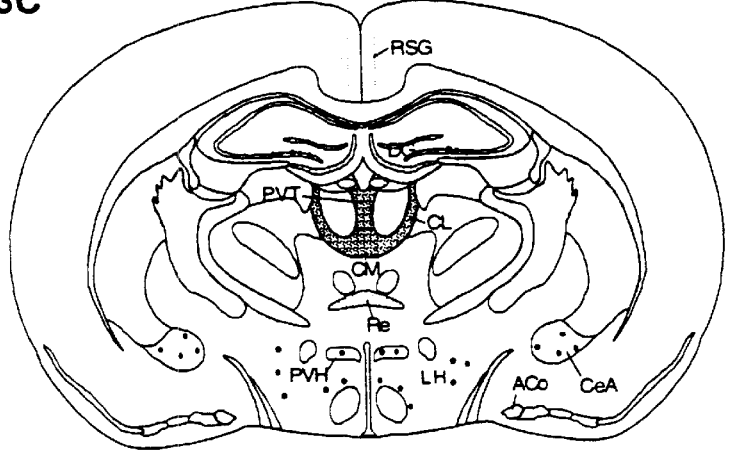

FIGURE 14

```
   1  TCATGTGTCA CATTATGCCT TTTCTTCAAT GTGTGTCAGT TCTGGTTTCA        50
  51  ACTTAATTC  TAATATCAAT TGCCATTGTC AGGTATCATA TGATCAAGCA        51
 101  TCCTATATCT AACAATTTAA CAGCAAACCA TGGCTACTTC CTGATTGCTA       150
 151  CTGTCTGGAC ACTAGGTTTT GCGATTTGTT CTCCCCTTCC AGTGTTTCAC       200
 201  AGTCTGGTGG AACTTCAGGA AACATTTGAC TCCGCATTGC TGAGCAGCAG       250
 251  GTATTTATGT GTTGAGTCGT GGCCATCTGA TTCGTACAGA ATCGCTTTTA       300
 301  CTATCTCTTT ATTGCTAGTC CAGTATATTC TTCCCTTGGT GTGTCTAACT       350
 351  GTGAGCCATA CCAGTGTCTG CAGGAGTATA AGCTGCGGGT TGTCCAACAA       400
 401  AGAAAACAAA CTGGAAGAAA ACGAGATGAT CAACTTAACT CTTCAACCAT       450
 451  TCAAAAAGAG TGGGCCTCAG GTGAAACTTT CCAGCAGCCA TAAATGGAGC       500
 501  TATTCATTCA TCAGAAAACA CAGGAGAAGG TACAGCAAGA AGACGGCGTG       550
 551  TGTCTTACCT GCTCCAGCAA GACCTCCTCA AGAGAACCAC TCAAGAATGC       600
 601  TTCCAGAAAA CTTTGGTTCT GTAAGAAGTC AGCATTCTTC ATCCAGTAAG       650
 651  TTCATACCGG GGGTCCCCAC CTGCTTTGAG GTGAAACCTG AAGAAAACTC       700
 701  GGATGTTCAT GACATGAGAG TAAACCGTTC TATCATGAGA ATCAAAAAGA       750
 751  GATCCCGAAG TGTTTTCTAT AGACTAACCA TACTGATACT AGTGTTTGCC       800
 801  GTTAGCTGGA TGCCACTACA CCTTTTTCCAT GTGGTAACTG ATTTAATGA       850
 851  CAACCTCATT TCAAACAGGC ATTTCAAATT GGTGTATTGC ATTGTCATT        900
 901  TGTTAGGCAT GATGTCCTGT TGTCTTAATC CTATTCTGTA TGGTTTTCTC       950
 951  AATAATGGGA TCAAAGCTGA TTTAATTTCC CTTATACAGT GTCTTCATAT      1000
1001  GTCATAATTA TTAATGTTTA CCAAGGAGAC AACAAATGTT GGGATCGTCT      1050
1051  AAAA
```

FIGURE 15

```
1    MCHIMPFLQC VSVLVSTLIL ISIAIVRYHM IKHPISNNLT ANHGYFLIAT    50
51   VWTLGFAICS PLPVFHSLVE LQETFDSALL SSRYLCVESW PSDSYRIAFT    100
101  ISLLLVQYIL PLVCLTVSHT SVCRSISCGL SNKENKLEEN EMINLTLQPF    150
151  KKSGPQVKLS SSHKWSYSFI RKHRRRYSKK TACVLPAPAR PPQENHSRML    200
201  PENFGSVRSQ HSSSSKFIPG VPTCFEVKPE ENSDVHDMRV NRSIMRIKKR    250
251  SRSVFYRLTI LILVFAVSWM PLHLFHVVTD FNDNLISNRH FKLVYCICHL    300
301  LGMMSCCLNP ILYGFLNNGI KADLISLIQC LHMS
```

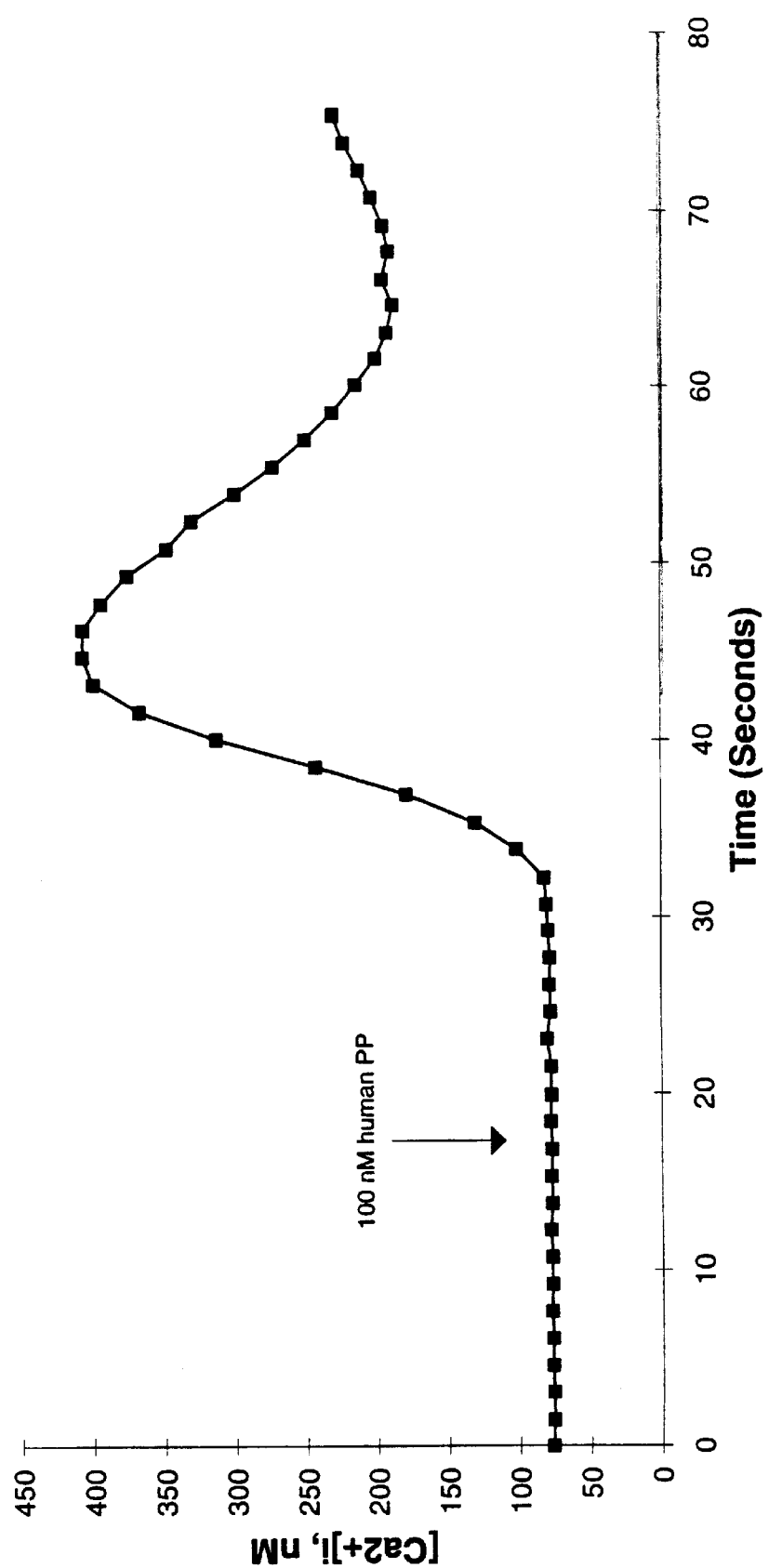

FIGURE 22A
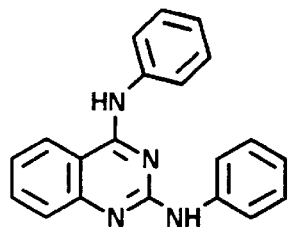
Compound 1
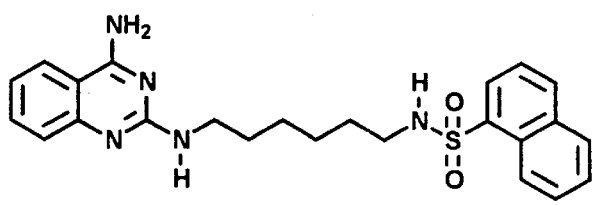
Compound 2
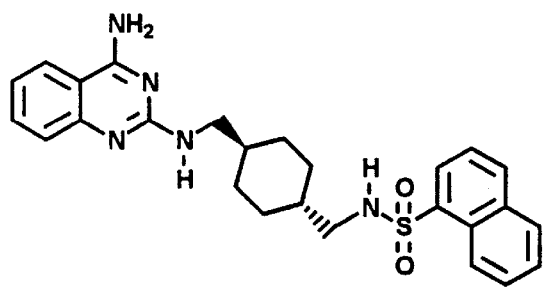
Compound 5
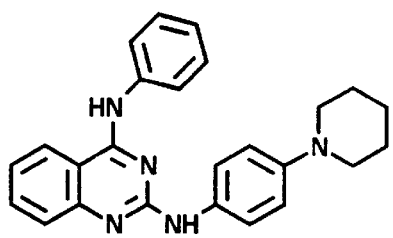
Compound 6
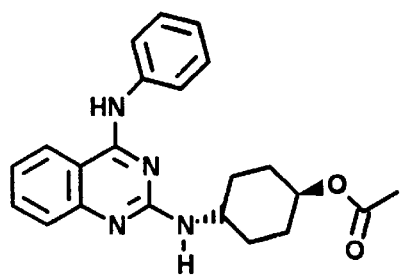
Compound 7
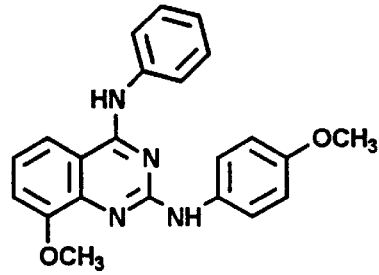
Compound 9
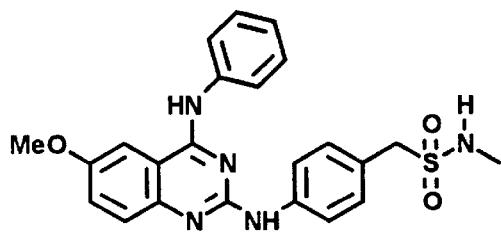
Compound 10
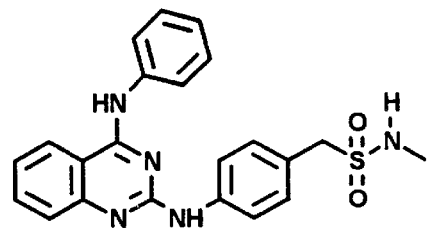
Compound 11

FIGURE 22B
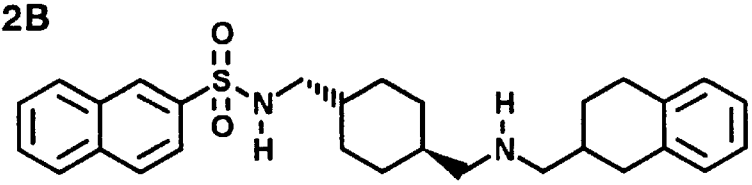
Compound 17
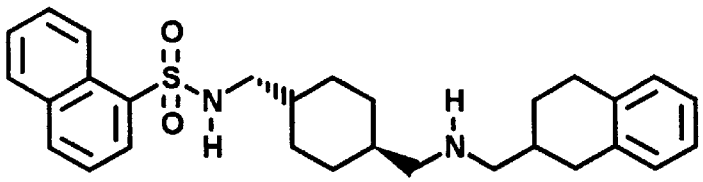
Compound 19
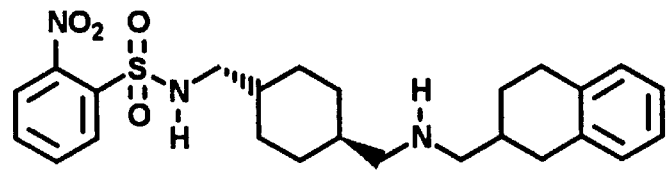
Compound 20
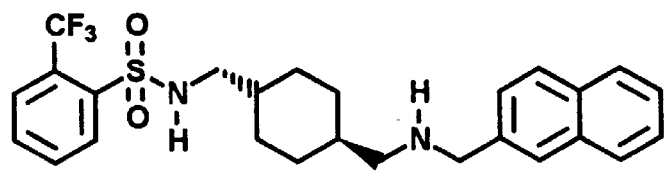
Compound 21
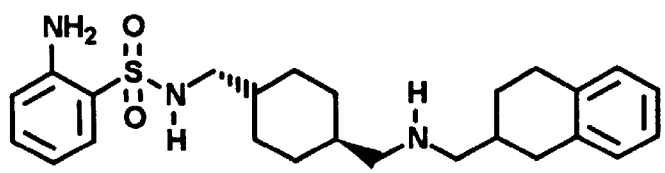
Compound 22

FIGURE 22C
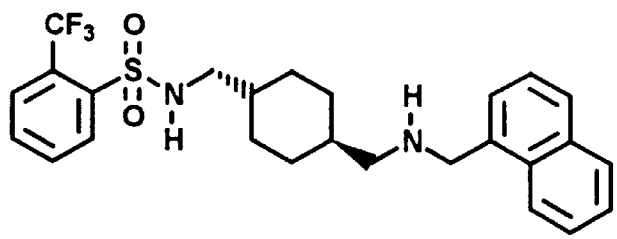
Compound 23
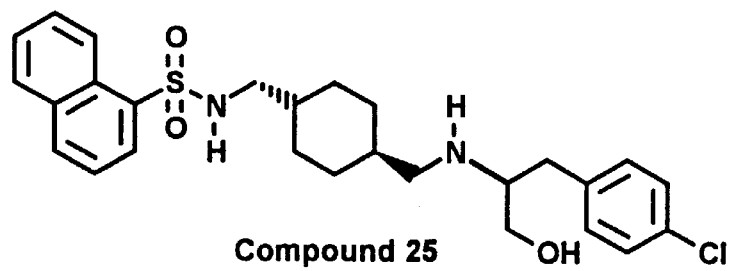
Compound 25
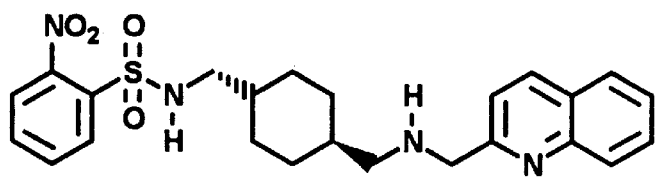
Compound 26
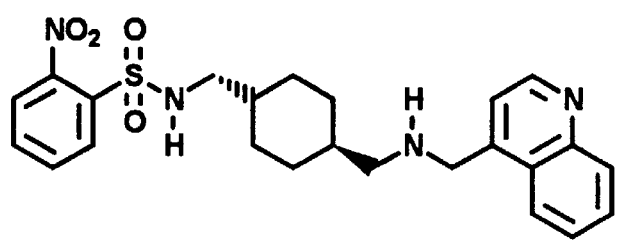
Compound 27
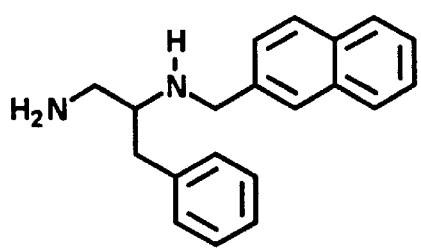
Compound 28

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1501 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
TTAGTTTTGT TCTGAGAACG TTAGAGTTAT AGTACCGTGC GATCGTTCTT CAAGCTGCTA      60

ATGGACGTCC TCTTCTTCCA CCAGGATTCT AGTATGGAGT TTAAGCTTGA GGAGCATTTT     120

AACAAGACAT TTGTCACAGA GAACAATACA GCTGCTGCTC GGAATGCAGC CTTCCCTGCC     180

TGGGAGGACT ACAGAGGCAG CGTAGACGAT TTACAATACT TTCTGATTGG GCTCTATACA     240

TTCGTAAGTC TTCTTGGCTT TATGGGCAAT CTACTTATTT TAATGGCTGT TATGAAAAAG     300

CGCAATCAGA AGACTACAGT GAACTTTCTC ATAGGCAACC TGGCCTTCTC CGACATCTTG     360

GTCGTCCTGT TTTGCTCCCC TTTCACCCTG ACCTCTGTCT TGTTGGATCA GTGGATGTTT     420

GGCAAAGCCA TGTGCCATAT CATGCCGTTC CTTCAATGTG TGTCAGTTCT GGTTTCAACT     480

CTGATTTTAA TATCAATTGC CATTGTCAGG TATCATATGA TAAAGCACCC TATTTCTAAC     540

AATTTAACGG CAAACCATGG CTACTTCCTG ATAGCTACTG TCTGGACACT GGGCTTTGCC     600

ATCTGTTCTC CCCTCCCAGT GTTTCACAGT CTTGTGGAAC TTAAGGAGAC CTTTGGCTCA     660

GCACTGCTGA GTAGCAAATA TCTCTGTGTT GAGTCATGGC CCTCTGATTC ATACAGAATT     720

GCTTTCACAA TCTCTTTATT GCTAGTGCAG TATATCCTGC CTCTAGTATG TTTAACGGTA     780

AGTCATACCA GCGTCTGCCG AAGCATAAGC TGTGGATTGT CCCACAAAGA AAACAGACTC     840

GAAGAAAATG AGATGATCAA CTTAACCCTA CAGCCATCCA AAAAGAGCAG GAACCAGGCA     900

AAAACCCCCA GCACTCAAAA GTGGAGCTAC TCATTCATCA GAAAGCACAG AAGGAGGTAC     960

AGCAAGAAGA CGGCCTGTGT CTTACCCGCC CCAGCAGGAC CTTCCAGGG GAAGCACCTA    1020

GCCGTTCCAG AAAATCCAGC CTCCGTCCGT AGCCAGCTGT CGCCATCCAG TAAGGTCATT    1080

CCAGGGGTCC CAATCTGCTT TGAGGTGAAA CCTGAAGAAA GCTCAGATGC TCATGAGATG    1140

AGAGTCAAGC GTTCCATCAC TAGAATAAAA AAGAGATCTC GAAGTGTTTT CTACAGACTG    1200

ACCATACTGA TACTCGTGTT CGCCGTTAGC TGGATGCCAC TCCACGTCTT CCACGTGGTG    1260

ACTGACTTCA ATGATAACTT GATTTCCAAT AGGCATTTCA AGCTGGTATA CTGCATCTGT    1320
```

-continued

```
CACTTGTTAG GCATGATGTC CTGTTGTCTA AATCCGATCC TATATGGTTT CCTTAATAAT     1380

GGTATCAAAG CAGACTTGAG AGCCCTTATC CACTGCCTAC ACATGTCATG ATTCTCTCTG     1440

TGCACCAAAG AGAAGAAA CGTGGTAATT GACACATAAT TTATACAGAA GTATTCTGGA       1500

T                                                                    1501
```

(2) INFORMATION FOR SEQ ID NO:2:

(i) SEQUENCE CHARACTERISTICS:
        (A) LENGTH: 456 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Val Leu Phe Phe His Gln Asp Ser Ser Met Glu Phe Lys Leu
 1               5                  10                  15

Glu Glu His Phe Asn Lys Thr Phe Val Thr Glu Asn Asn Thr Ala Ala
             20                  25                  30

Ala Arg Asn Ala Ala Phe Pro Ala Trp Glu Asp Tyr Arg Gly Ser Val
         35                  40                  45

Asp Asp Leu Gln Tyr Phe Leu Ile Gly Leu Tyr Thr Phe Val Ser Leu
     50                  55                  60

Leu Gly Phe Met Gly Asn Leu Leu Ile Leu Met Ala Val Met Lys Lys
 65                  70                  75                  80

Arg Asn Gln Lys Thr Thr Val Asn Phe Leu Ile Gly Asn Leu Ala Phe
                 85                  90                  95

Ser Asp Ile Leu Val Val Leu Phe Cys Ser Pro Phe Thr Leu Thr Ser
            100                 105                 110

Val Leu Leu Asp Gln Trp Met Phe Gly Lys Ala Met Cys His Ile Met
        115                 120                 125

Pro Phe Leu Gln Cys Val Ser Val Leu Val Ser Thr Leu Ile Leu Ile
130                 135                 140

Ser Ile Ala Ile Val Arg Tyr His Met Ile Lys His Pro Ile Ser Asn
145                 150                 155                 160

Asn Leu Thr Ala Asn His Gly Tyr Phe Leu Ile Ala Thr Val Trp Thr
                165                 170                 175

Leu Gly Phe Ala Ile Cys Ser Pro Leu Pro Val Phe His Ser Leu Val
            180                 185                 190

Glu Leu Lys Glu Thr Phe Gly Ser Ala Leu Leu Ser Ser Lys Tyr Leu
        195                 200                 205

Cys Val Glu Ser Trp Pro Ser Asp Ser Tyr Arg Ile Ala Phe Thr Ile
    210                 215                 220

Ser Leu Leu Leu Val Gln Tyr Ile Leu Pro Leu Val Cys Leu Thr Val
225                 230                 235                 240

Ser His Thr Ser Val Cys Arg Ser Ile Ser Cys Gly Leu Ser His Lys
                245                 250                 255

Glu Asn Arg Leu Glu Glu Asn Glu Met Ile Asn Leu Thr Leu Gln Pro
            260                 265                 270

Ser Lys Lys Ser Arg Asn Gln Ala Lys Thr Pro Ser Thr Gln Lys Trp
        275                 280                 285

Ser Tyr Ser Phe Ile Arg Lys His Arg Arg Arg Tyr Ser Lys Lys Thr
    290                 295                 300

Ala Cys Val Leu Pro Ala Pro Ala Gly Pro Ser Gln Gly Lys His Leu
305                 310                 315                 320
```

```
Ala Val Pro Glu Asn Pro Ala Ser Val Arg Ser Gln Leu Ser Pro Ser
                325                 330                 335

Ser Lys Val Ile Pro Gly Val Pro Ile Cys Phe Glu Val Lys Pro Glu
            340                 345                 350

Glu Ser Ser Asp Ala His Glu Met Arg Val Lys Arg Ser Ile Thr Arg
            355                 360                 365

Ile Lys Lys Arg Ser Arg Ser Val Phe Tyr Arg Leu Thr Ile Leu Ile
        370                 375                 380

Leu Val Phe Ala Val Ser Trp Met Pro Leu His Val Phe His Val Val
385                 390                 395                 400

Thr Asp Phe Asn Asp Asn Leu Ile Ser Asn Arg His Phe Lys Leu Val
                405                 410                 415

Tyr Cys Ile Cys His Leu Leu Gly Met Met Ser Cys Cys Leu Asn Pro
                420                 425                 430

Ile Leu Tyr Gly Phe Leu Asn Asn Gly Ile Lys Ala Asp Leu Arg Ala
            435                 440                 445

Leu Ile His Cys Leu His Met Ser
450                 455

(2) INFORMATION FOR SEQ ID NO:3:

(i) SEQUENCE CHARACTERISTICS:
        (A) LENGTH: 1457 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GTTTCCCTCT GAATAGATTA ATTTAAAGTA GTCATGTAAT GTTTTTTTGG TTGCTGACAA      60

ATGTCTTTTT ATTCCAAGCA GGACTATAAT ATGGATTTAG AGCTCGACGA GTATTATAAC     120

AAGACACTTG CCACAGAGAA TAATACTGCT GCCACTCGGA ATTCTGATTT CCCAGTCTGG     180

GATGACTATA AAAGCAGTGT AGATGACTTA CAGTATTTTC TGATTGGGCT CTATACATTT     240

GTAAGTCTTC TTGGCTTTAT GGGGAATCTA CTTATTTTAA TGGCTCTCAT GAAAAAGCGT     300

AATCAGAAGA CTACGGTAAA CTTCCTCATA GGCAATCTGG CCTTTTCTGA TATCTTGGTT     360

GTGCTGTTTT GCTCACCTTT CACACTGACG TCTGTCTTGC TGGATCAGTG GATGTTTGGC     420

AAAGTCATGT GCCATATTAT GCCTTTTCTT CAATGTGTGT CAGTTTTGGT TTCAACTTTA     480

ATTTTAATAT CAATTGCCAT TGTCAGGTAT CATATGATAA ACATCCCAT ATCTAATAAT     540

TTAACAGCAA ACCATGGCTA CTTTCTGATA GCTACTGTCT GGACACTAGG TTTTGCCATC     600

TGTTCTCCCC TTCCAGTGTT TCACAGTCTT GTGGAACTTC AAGAAACATT TGGTTCAGCA     660

TTGCTGAGCA GCAGGTATTT ATGTGTTGAG TCATGGCCAT CTGATTCATA CAGAATTGCC     720

TTTACTATCT CTTTATTGCT AGTTCAGTAT ATTCTGCCCT TAGTTTGTCT TACTGTAAGT     780

CATACAAGTG TCTGCAGAAG TATAAGCTGT GGATTGTCCA ACAAAGAAAA CAGACTTGAA     840

GAAAATGAGA TGATCAACTT AACTCTTCAT CCATCCAAAA AGAGTGGGCC TCAGGTGAAA     900

CTCTCTGGCA GCCATAAATG GAGTTATTCA TTCATCAAAA AACACAGAAG AAGATATAGC     960

AAGAAGACAG CATGTGTGTT ACCTGCTCCA GAAAGACCTT CTCAAGAGAA CCACTCCAGA    1020

ATACTTCCAG AAAACTTTGG CTCTGTAAGA AGTCAGCTCT CTTCATCCAG TAAGTTCATA    1080

CCAGGGGTCC CCACTTGCTT TGAGATAAAA CCTGAAGAAA ATTCAGATGT TCATGAATTG    1140

AGAGTAAAAC GTTCTGTTAC AAGAATAAAA AAGAGATCTC GAAGTGTTTT CTACAGACTG    1200
```

-continued

```
ACCATACTGA TATTAGTATT TGCTGTTAGT TGGATGCCAC TACACCTTTT CCATGTGGTA    1260

ACTGATTTTA ATGACAATCT TATTTCAAAT AGGCATTTCA AGTTGGTGTA TTGCATTTGT    1320

CATTTGTTGG GCATGATGTC CTGTTGTCTT AATCCAATTC TATATGGGTT TCTTAATAAT    1380

GGGATTAAAG CTGATTTAGT GTCCCTTATA CACTGTCTTC ATATGTAATA ATTCTCACTG    1440

TTTACCAAGG AAAGAAC                                                   1457
```

(2) INFORMATION FOR SEQ ID NO:4:

(i) SEQUENCE CHARACTERISTICS:
        (A) LENGTH: 455 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Phe Tyr Ser Lys Gln Asp Tyr Asn Met Asp Leu Glu Leu Asp
 1               5                  10                  15

Glu Tyr Tyr Asn Lys Thr Leu Ala Thr Glu Asn Asn Thr Ala Ala Thr
            20                  25                  30

Arg Asn Ser Asp Phe Pro Val Trp Asp Asp Tyr Lys Ser Ser Val Asp
        35                  40                  45

Asp Leu Gln Tyr Phe Leu Ile Gly Leu Tyr Thr Phe Val Ser Leu Leu
    50                  55                  60

Gly Phe Met Gly Asn Leu Leu Ile Leu Met Ala Leu Met Lys Lys Arg
65                  70                  75                  80

Asn Gln Lys Thr Thr Val Asn Phe Leu Ile Gly Asn Leu Ala Phe Ser
                85                  90                  95

Asp Ile Leu Val Val Leu Phe Cys Ser Pro Phe Thr Leu Thr Ser Val
            100                 105                 110

Leu Leu Asp Gln Trp Met Phe Gly Lys Val Met Cys His Ile Met Pro
        115                 120                 125

Phe Leu Gln Cys Val Ser Val Leu Val Ser Thr Leu Ile Leu Ile Ser
    130                 135                 140

Ile Ala Ile Val Arg Tyr His Met Ile Lys His Pro Ile Ser Asn Asn
145                 150                 155                 160

Leu Thr Ala Asn His Gly Tyr Phe Leu Ile Ala Thr Val Trp Thr Leu
                165                 170                 175

Gly Phe Ala Ile Cys Ser Pro Leu Pro Val Phe His Ser Leu Val Glu
            180                 185                 190

Leu Gln Glu Thr Phe Gly Ser Ala Leu Leu Ser Ser Arg Tyr Leu Cys
        195                 200                 205

Val Glu Ser Trp Pro Ser Asp Ser Tyr Arg Ile Ala Phe Thr Ile Ser
    210                 215                 220

Leu Leu Leu Val Gln Tyr Ile Leu Pro Leu Val Cys Leu Thr Val Ser
225                 230                 235                 240

His Thr Ser Val Cys Arg Ser Ile Ser Cys Gly Leu Ser Asn Lys Glu
                245                 250                 255

Asn Arg Leu Glu Glu Asn Glu Met Ile Asn Leu Thr Leu His Pro Ser
            260                 265                 270

Lys Lys Ser Gly Pro Gln Val Lys Leu Ser Gly Ser His Lys Trp Ser
        275                 280                 285

Tyr Ser Phe Ile Lys Lys His Arg Arg Arg Tyr Ser Lys Lys Thr Ala
    290                 295                 300

Cys Val Leu Pro Ala Pro Glu Arg Pro Ser Gln Glu Asn His Ser Arg
```

```
305                 310                 315                 320
Ile Leu Pro Glu Asn Phe Gly Ser Val Arg Ser Gln Leu Ser Ser Ser
                325                 330                 335

Ser Lys Phe Ile Pro Gly Val Pro Thr Cys Phe Glu Ile Lys Pro Glu
                340                 345                 350

Glu Asn Ser Asp Val His Glu Leu Arg Val Lys Arg Ser Val Thr Arg
                355                 360                 365

Ile Lys Lys Arg Ser Arg Ser Val Phe Tyr Arg Leu Thr Ile Leu Ile
                370                 375                 380

Leu Val Phe Ala Val Ser Trp Met Pro Leu His Leu Phe His Val Val
385                 390                 395                 400

Thr Asp Phe Asn Asp Asn Leu Ile Ser Asn Arg His Phe Lys Leu Val
                405                 410                 415

Tyr Cys Ile Cys His Leu Leu Gly Met Met Ser Cys Cys Leu Asn Pro
                420                 425                 430

Ile Leu Tyr Gly Phe Leu Asn Asn Gly Ile Lys Ala Asp Leu Val Ser
                435                 440                 445

Leu Ile His Cys Leu His Met
450                 455

(2) INFORMATION FOR SEQ ID NO:5:

(i) SEQUENCE CHARACTERISTICS:
        (A) LENGTH: 1054 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 3..1004

(xi) SEQUENCE DESCRIPTION: SEQ ID NO:5:

TC ATG TGT CAC ATT ATG CCT TTT CTT CAA TGT GTG TCA GTT CTG GTT      47
   Met Cys His Ile Met Pro Phe Leu Gln Cys Val Ser Val Leu Val
     1               5                  10                  15

TCA ACT TTA ATT CTA ATA TCA ATT GCC ATT GTC AGG TAT CAT ATG ATC     95
Ser Thr Leu Ile Leu Ile Ser Ile Ala Ile Val Arg Tyr His Met Ile
                20                  25                  30

AAG CAT CCT ATA TCT AAC AAT TTA ACA GCA AAC CAT GGC TAC TTC CTG    143
Lys His Pro Ile Ser Asn Asn Leu Thr Ala Asn His Gly Tyr Phe Leu
                35                  40                  45

ATT GCT ACT GTC TGG ACA CTA GGT TTT GCG ATT TGT TCT CCC CTT CCA    191
Ile Ala Thr Val Trp Thr Leu Gly Phe Ala Ile Cys Ser Pro Leu Pro
            50                  55                  60

GTG TTT CAC AGT CTG GTG GAA CTT CAG GAA ACA TTT GAC TCC GCA TTG    239
Val Phe His Ser Leu Val Glu Leu Gln Glu Thr Phe Asp Ser Ala Leu
65                  70                  75

CTG AGC AGC AGG TAT TTA TGT GTT GAG TCG TGG CCA TCT GAT TCG TAC    287
Leu Ser Ser Arg Tyr Leu Cys Val Glu Ser Trp Pro Ser Asp Ser Tyr
80                  85                  90                  95

AGA ATC GCT TTT ACT ATC TCT TTA TTG CTA GTC CAG TAT ATT CTT CCC    335
Arg Ile Ala Phe Thr Ile Ser Leu Leu Leu Val Gln Tyr Ile Leu Pro
                100                 105                 110

TTG GTG TGT CTA ACT GTG AGC CAT ACC AGT GTC TGC AGG AGT ATA AGC    383
Leu Val Cys Leu Thr Val Ser His Thr Ser Val Cys Arg Ser Ile Ser
                115                 120                 125

TGC GGG TTG TCC AAC AAA GAA AAC AAA CTG GAA GAA AAC GAG ATG ATC    431
Cys Gly Leu Ser Asn Lys Glu Asn Lys Leu Glu Glu Asn Glu Met Ile
```

```
                   130                 135                 140
AAC TTA ACT CTT CAA CCA TTC AAA AAG AGT GGG CCT CAG GTG AAA CTT    479
Asn Leu Thr Leu Gln Pro Phe Lys Lys Ser Gly Pro Gln Val Lys Leu
    145                 150                 155

TCC AGC AGC CAT AAA TGG AGC TAT TCA TTC ATC AGA AAA CAC AGG AGA    527
Ser Ser Ser His Lys Trp Ser Tyr Ser Phe Ile Arg Lys His Arg Arg
160                 165                 170                 175

AGG TAC AGC AAG AAG ACG GCG TGT GTC TTA CCT GCT CCA GCA AGA CCT    575
Arg Tyr Ser Lys Lys Thr Ala Cys Val Leu Pro Ala Pro Ala Arg Pro
                180                 185                 190

CCT CAA GAG AAC CAC TCA AGA ATG CTT CCA GAA AAC TTT GGT TCT GTA    623
Pro Gln Glu Asn His Ser Arg Met Leu Pro Glu Asn Phe Gly Ser Val
            195                 200                 205

AGA AGT CAG CAT TCT TCA TCC AGT AAG TTC ATA CCG GGG GTC CCC ACC    671
Arg Ser Gln His Ser Ser Ser Ser Lys Phe Ile Pro Gly Val Pro Thr
        210                 215                 220

TGC TTT GAG GTG AAA CCT GAA GAA AAC TCG GAT GTT CAT GAC ATG AGA    719
Cys Phe Glu Val Lys Pro Glu Glu Asn Ser Asp Val His Asp Met Arg
    225                 230                 235

GTA AAC CGT TCT ATC ATG AGA ATC AAA AAG AGA TCC CGA AGT GTT TTC    767
Val Asn Arg Ser Ile Met Arg Ile Lys Lys Arg Ser Arg Ser Val Phe
240                 245                 250                 255

TAT AGA CTA ACC ATA CTG ATA CTA GTG TTT GCC GTT AGC TGG ATG CCA    815
Tyr Arg Leu Thr Ile Leu Ile Leu Val Phe Ala Val Ser Trp Met Pro
                260                 265                 270

CTA CAC CTT TTC CAT GTG GTA ACT GAT TTT AAT GAC AAC CTC ATT TCA    863
Leu His Leu Phe His Val Val Thr Asp Phe Asn Asp Asn Leu Ile Ser
            275                 280                 285

AAC AGG CAT TTC AAA TTG GTG TAT TGC ATT TGT CAT TTG TTA GGC ATG    911
Asn Arg His Phe Lys Leu Val Tyr Cys Ile Cys His Leu Leu Gly Met
        290                 295                 300

ATG TCC TGT TGT CTT AAT CCT ATT CTG TAT GGT TTT CTC AAT AAT GGG    959
Met Ser Cys Cys Leu Asn Pro Ile Leu Tyr Gly Phe Leu Asn Asn Gly
    305                 310                 315

ATC AAA GCT GAT TTA ATT TCC CTT ATA CAG TGT CTT CAT ATG TCA        1004
Ile Lys Ala Asp Leu Ile Ser Leu Ile Gln Cys Leu His Met Ser
320                 325                 330

TAATTATTAA TGTTTACCAA GGAGACAACA AATGTTGGGA TCGTCTAAAA             1054

(2) INFORMATION FOR SEQ ID NO:6:

(i) SEQUENCE CHARACTERISTICS:
          (A) LENGTH: 334 amino acids
          (B) TYPE: amino acid
          (D) TOPOLOGY: linear (ii) MOLECULE TYPE: protein (xi) SEQUENCE DESCRIPTION: SEQ ID NO:6:

Met Cys His Ile Met Pro Phe Leu Gln Cys Val Ser Val Leu Val Ser
  1               5                  10                  15

Thr Leu Ile Leu Ile Ser Ile Ala Ile Val Arg Tyr His Met Ile Lys
                20                  25                  30

His Pro Ile Ser Asn Asn Leu Thr Ala Asn His Gly Tyr Phe Leu Ile
            35                  40                  45

Ala Thr Val Trp Thr Leu Gly Phe Ala Ile Cys Ser Pro Leu Pro Val
        50                  55                  60

Phe His Ser Leu Val Glu Leu Gln Glu Thr Phe Asp Ser Ala Leu Leu
65                  70                  75                  80

Ser Ser Arg Tyr Leu Cys Val Glu Ser Trp Pro Ser Asp Ser Tyr Arg
```

```
                     85                  90                  95
Ile Ala Phe Thr Ile Ser Leu Leu Val Gln Tyr Ile Leu Pro Leu
                100                 105                 110

Val Cys Leu Thr Val Ser His Thr Ser Val Cys Arg Ser Ile Ser Cys
            115                 120                 125

Gly Leu Ser Asn Lys Glu Asn Lys Leu Glu Glu Asn Glu Met Ile Asn
        130                 135                 140

Leu Thr Leu Gln Pro Phe Lys Lys Ser Gly Pro Gln Val Lys Leu Ser
145                 150                 155                 160

Ser Ser His Lys Trp Ser Tyr Ser Phe Ile Arg Lys His Arg Arg Arg
                165                 170                 175

Tyr Ser Lys Lys Thr Ala Cys Val Leu Pro Ala Pro Ala Arg Pro Pro
                180                 185                 190

Gln Glu Asn His Ser Arg Met Leu Pro Glu Asn Phe Gly Ser Val Arg
                195                 200                 205

Ser Gln His Ser Ser Ser Lys Phe Ile Pro Gly Val Pro Thr Cys
        210                 215                 220

Phe Glu Val Lys Pro Glu Glu Asn Ser Asp Val His Asp Met Arg Val
225                 230                 235                 240

Asn Arg Ser Ile Met Arg Ile Lys Lys Arg Ser Arg Ser Val Phe Tyr
                245                 250                 255

Arg Leu Thr Ile Leu Ile Leu Val Phe Ala Val Ser Trp Met Pro Leu
                260                 265                 270

His Leu Phe His Val Val Thr Asp Phe Asn Asp Asn Leu Ile Ser Asn
                275                 280                 285

Arg His Phe Lys Leu Val Tyr Cys Ile Cys His Leu Leu Gly Met Met
        290                 295                 300

Ser Cys Cys Leu Asn Pro Ile Leu Tyr Gly Phe Leu Asn Asn Gly Ile
305                 310                 315                 320

Lys Ala Asp Leu Ile Ser Leu Ile Gln Cys Leu His Met Ser
                325                 330
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TGGATCAGTG GATGTTTGGC AAAG        24

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GTCTGTAGAA AACACTTCGA GATCTCTT        28

(2) INFORMATION FOR SEQ ID NO:9:

```
         (i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:9:

CTTCCAGTGT TTCACAGTCT GGTGG                                              25

(2) INFORMATION FOR SEQ ID NO:10:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:10:

CTGAGCAGCA GGTATTTATG TGTTG                                              25

(2) INFORMATION FOR SEQ ID NO:11:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:11:

CTGGATGAAG AATGCTGACT TCTTAGAG                                           28

(2) INFORMATION FOR SEQ ID NO:12:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:12:

TTCTTGAGTG GTTCTCTTGA GGAGG                                              25
```

DNA ENCODING A HYPOTHALAMIC ATYPICAL NEUROPEPTIDE Y/PEPTIDE YY RECEPTOR (Y5)

This application is a continuation-in-part of U.S. Ser. No. 08/349,025, filed Dec. 2, 1994, now U.S. Pat. No. 5,602,024 the contents of which are hereby incorporated by reference into the subject application.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the sequence listing and the claims.

Neuropeptide Y (NPY) is a member of the pancreatic polypeptide family with widespread distribution throughout the mammalian nervous system. NPY and its relatives (peptide YY or PYY, and pancreatic polypeptide or PP) elicit a broad range of physiological effects through activation of at least five G protein-coupled receptor subtypes known as Y1, Y2, Y3, Y4 (or PP), and the "atypical Y1". The role of NPY as the most powerful stimulant of feeding behavior yet described is thought to occur primarily through activation of the hypothalamic "atypical Y1" receptor. This receptor is unique in that its classification was based solely on feeding behavior data, rather than radioligand binding data, unlike the Y1, Y2, Y3, and Y4 (or PP) receptors, each of which were described previously in both radioligand binding and functional assays. Applicants now report the use of a $^{125}$I-PYY-based expression cloning technique to isolate a rat hypothalamic cDNA encoding an "atypical Y1" receptor referred to herein as the Y5 subtype. Applicants also report the isolation and characterization of a Y5 homolog from human hippocampus. Protein sequence analysis reveals that the Y5 receptor belongs to the G protein-coupled receptor superfamily. Both the human and rat homolog display $\leq 42\%$ identity in transmembrane domains with the previously cloned "Y-type" receptors. Rat brain localization studies using in situ hybridization techniques verified the existence of Y5 receptor mRNA in rat hypothalamus. Pharmacological evaluation revealed the following similarities between the Y5 and the "atypical Y1" receptor. 1) Peptides bound to the Y5 receptor with a rank order of potency identical to that described for the feeding response: NPY$\geq$NPY$_{2-36}$=PYY=[Leu$^{31}$, Pro$^{34}$]NPY>>NPY$_{13-36}$. 2) The Y5 receptor was negatively coupled to cAMP accumulation, as had been proposed for the "atypical Y1" receptor. 3) Peptides activated the Y5 receptor with a rank order of potency identical to that described for the feeding response. 4) The reported feeding "modulator" [D-Trp$^{32}$]NPY bound selectively to the Y5 receptor and subsequently activated the receptor. 5) Both the Y5 and the "atypical Y1" receptors were sensitive to deletions or modifications in the midregion of NPY and related peptide ligands. These data support the identity of the Y5 receptor as the previously described "atypical Y1", and furthermore indicate a role for the Y5 receptor as a potential target in the treatment of obesity, metabolism, and appetite disorders.

The peptide neurotransmitter neuropeptide Y (NPY) is a 36 amino acid member of the pancreatic polypeptide family with widespread distribution throughout the mammalian nervous system. NPY is considered to be the most powerful stimulant of feeding behavior yet described (Clark et al., 1984; Levine and Morley, 1984; Stanley and Leibowitz, 1984). Direct injection into the hypothalamus of satiated rats, for example, can increase food intake up to 10-fold over a 4-hour period (Stanley et al., 1992). The role of NPY in normal and abnormal eating behavior, and the ability to interfere with NPY-dependent pathways as a means to appetite and weight control, are areas of great interest in pharmacological and pharmaceutical research (Sahu and Kalra, 1993; Dryden et al., 1994). Any credible means of studying or controlling NPY-dependent feeding behavior, however, must necessarily be highly specific as NPY can act through at least 5 pharmacologically defined receptor subtypes to elicit a wide variety of physiological functions (Dumont et al., 1992). It is therefore vital that knowledge of the molecular biology and structural diversity of the individual receptor subtypes be understood as part of a rational drug design approach to develop subtype selective compounds. A brief review of NPY receptor pharmacology is summarized below and also in Table 1.

TABLE 1: Pharmacologically defined receptors for NPY and related pancreatic polypeptides.

Rank orders of affinity for key peptides (NPY, PYY, PP, [Leu$^{31}$, Pro$^{34}$]NPY, NPY$_{2-36}$, and NPY$_{13-36}$) are based on previously reported binding and functional data (Schwartz et al., 1990; Wahlestedt et al., 1991; Dumont et al., 1992; Wahlestedt and Reis, 1993). Data for the Y2 receptor were disclosed in U.S. patent application Ser. No. 08/192,288 filed on Feb. 3, 1994, now U.S. Pat. No. 5,545,549, the foregoing contents of which are hereby incorporated by reference. Data for the Y4 receptor were disclosed in U.S. patent application Ser. No. 08/176,412 filed on Dec. 28 1993, now U.S. Pat. No. 5,516,653, the contents of which are hereby incorporated by reference. Missing peptides in the series reflect a lack of published information.

TABLE 1

| Recep-tor | Affinity (pK$_i$ or pEC$_{50}$) | | | | |
|---|---|---|---|---|---|
| | 11 to 10 | 10 to 9 | 9 to 8 | 8 to 7 | 7 to 6  >6 |
| Y1 | NPY<br>PYY<br>[Leu$^{31}$, Pro$^{34}$]<br>NPY | | NPY$_{2-36}$ | NPY$_{13-36}$ | PP |
| Y2 | | PYY<br>NPY<br>NPY$_{2-36}$ | NPY$_{13-36}$ | | [Leu$^{31}$, Pro$^{34}$]<br>NPY<br>PP |
| Y3 | | NPY | [Pro$^{34}$] | NPY$_{13-36}$PP | PYY |
| Y4 | PP | PYY<br>[Leu$^{31}$, Pro$^{34}$]<br>NPY | NPY<br>NPY$_{2-36}$ | NPY$_{13-36}$ | |
| atypical Y1 (feed-ing) | | PYY<br>NPY<br>NPY$_{2-36}$<br>[Leu$^{31}$, Pro$^{34}$]<br>NPY | | NPY$_{13-36}$ | |

NPY Receptor Pharmacology

NPY receptor pharmacology has historically been based on structure/activity relationships within the pancreatic polypeptide family. The entire family includes the namesake pancreatic polypeptide (pp), synthesized primarily by endocrine cells in the pancreas; peptide YY (PYY), synthesized primarily by endocrine cells in the gut; and NPY, synthesized primarily in neurons (Michel, 1991; Dumont et al., 1992; Wahlestedt and Reis, 1993). All pancreatic polypeptide family members share a compact structure involving a "PP-fold" and a conserved C-terminal hexapeptide ending in Tyr$^{36}$ (or Y$^{36}$ in the single letter code). The striking conservation of Y$^{36}$ has prompted the reference to the pancreatic polypeptides' receptors as "Y-type" receptors (Wahlestedt et al., 1987), all of which are proposed to function as seven transmembrane-spanning G protein-coupled receptors (Dumont et al., 1992).

The Y1 receptor recognizes NPY≧PYY>>PP (Grundemar et al., 1992). The receptor requires both the N- and the C-terminal regions of the peptides for optimal recognition. Exchange of Gln$^{34}$ in NPY or PYY with the analogous residue from PP (Pro$^{34}$), however, is well-tolerated. The Y1 receptor has been cloned from a variety of species including human, rat and mouse (Larhammar et al, 1992; Herzog et al, 1992; Eva et al, 1990; Eva et al, 1992). The Y2 receptor recognizes PYY~NPY>>PP and is relatively tolerant of N-terminal deletion (Grundemar et al., 1992). The receptor has a strict requirement for structure in the C-terminus (Arg$^{33}$-Gln$^{34}$-Arg$^{35}$-Tyr$^{36}$-NH$_2$); exchange of Gln$^{34}$ with Pro$^{34}$, as in PP, is not well tolerated. The Y2 receptor has recently been cloned (disclosed in U.S. patent application Ser. No. 08/192,288, filed Feb. 3, 1994). The Y3 receptor is characterized by a strong preference for NPY over PYY and PP (Wahlestedt et al., 1991). [Pro$^{34}$]NPY is reasonably well tolerated even though PP, which also contains Pro$^{34}$, does not bind well to the Y3 receptor. The Y3 receptor (Y3) has not yet been cloned. The Y4 receptor (disclosed in U.S. patent application Ser. No. 08/176,412, filed Dec. 28, 1993, now U.S. Pat. No. 5,516,653) binds PP>PYY>NPY. Like the Y1, the Y4 requires both the N- and the C-terminal regions of the peptides for optimal recognition (U.S. Ser. No. 08/176,412, now U.S. Pat. No. 5,516,653). The "atypical Y1" or "feeding" receptor was defined exclusively by injection of several pancreatic polypeptide analogs into the paraventricular nucleus of the rat hypothalamus which stimulated feeding behavior with the following rank order: NPY$_{2-36}$≧NPY~PYY~[Leu$^{31}$,Pro$^{34}$]NPY>NPY$_{13-36}$ (Kalra et al., 1991; Stanley et al., 1992). The profile is similar to that of a Y1-like receptor except for the anomalous ability of NPY$_{2-36}$ to stimulate food intake with potency equivalent or better than that of NPY. A subsequent report in *J. Med. Chem.* by Balasubramaniam et al. (1994) showed that feeding can be regulated by [D-Trp$^{32}$]NPY. While this peptide was presented as an NPY antagonist, the published data at least in part support a stimulatory effect of [D-Trp$^{32}$]NPY on feeding. [D-Trp$^{32}$]NPY thereby represents another diagnostic tool for receptor identification. In contrast to other NPY receptor subtypes, the "feeding" receptor has never been characterized for peptide binding affinity in radioligand binding assays and the fact that a single receptor could be responsible for the feeding response has been impossible to validate in the absence of an isolated receptor protein; the possibility exists, for example, that the feeding response could be a composite profile of Y1 and Y2 subtypes.

Applicants now report the isolation by expression cloning of a novel Y-type receptor from a rat hypothalamic cDNA library, along with its pharmacological characterization, in situ localization, and human homologues. The data provided link this newly-cloned receptor subtype, from now on referred to as the Y5 subtype, to the "atypical Y1" feeding response. This discovery therefore provides a novel approach, through the use of heterologous expression systems, to develop a subtype selective antagonist for obesity and other indications.

Applicants further report the isolation of a canine Y5 receptor.

In addition, applicants report the discovery of chemical compounds which bind selectively to the Y5 receptor of the present invention and which act as antagonists of the Y5 receptor.

The treatment of disorders or diseases associated with the inhibition of the Y5 receptor subtype, especially diseases caused by eating disorders like obesity, bulimia nervosa, diabetes, dislipidimia, may be effected by administration of compounds which bind selectively to the Y5 receptor and inhibit the activation of the Y5 receptor. Furthermore, any disease states in which the Y5 receptor subtype is involved, for example, memory loss, epileptic seizures, migraine, sleep disturbance, and pain, may also be treated using compounds which bind selectively to the Y5 receptor.

SUMMARY OF THE INVENTION

This invention provides a method of modifying feeding behavior of a subject which comprises administering to the subject an amount of a compound which is a Y5 receptor agonist or antagonist effective to increase or decrease consumption of food by the subject so as to thereby modify feeding behavior of the subject.

This invention provides a method of treating a feeding disorder in a subject which comprises administering to the subject an amount of a non-peptidyl compound which is a Y5 receptor antagonist effective to inhibit the activity of the subject's Y5 receptor, wherein the binding of the compound to the human receptor is characterized by a K$_i$ less than 100 nanomolar when measured in the presence of $^{125}$I-PYY.

This invention provides a method of treating a feeding disorder in a subject which comprises administering to the subject an amount of a peptidyl compound which is a Y5 receptor antagonist effective to inhibit the activity of the subject's Y5 receptor, wherein the compound's binding to the human Y5 receptor is characterized by a K$_i$ less than 10 nanomolar when measured in the presence of $^{125}$I-PYY.

This invention provides a method of treating a feeding disorder in a subject which comprises administering to the subject an amount of a non-peptidyl compound which is a Y5 receptor agonist effective to increase the activity of the subject's Y5 receptor, wherein (a) the binding of the compound to the human Y5 receptor is characterized by a K$_i$ less than 100 nanomolar when measured in the presence of $^{125}$I-PYY; and (b) the binding of the compound to any other human Y-type receptor is characterized by a K$_i$ greater than 1000 nanomolar when measured in the presence of $^{125}$I-PYY.

This invention provides a method of treating a feeding disorder in a subject which comprises administering to the subject an amount of a non-peptidyl compound which is a Y5 receptor agonist effective to increase the activity of the subject's Y5 receptor, wherein (a) the binding of the compound to the human Y5 receptor is characterized by a K$_i$ less than 1 nanomolar when measured in the presence of $^{125}$I-PYY; and (b) the compound's binding to any other human Y-type receptor is characterized by a K$_i$ greater than 100 nanomolar when measured in the presence of $^{125}$I-PYY.

This invention provides a method of treating a feeding disorder in a subject which comprises administering to the subject an amount of a peptidyl compound which is a Y5 receptor agonist effective to increase the activity of the subject's Y5 receptor, wherein (a) the binding of the compound to the human Y5 receptor is characterized by a K$_i$ less than 1 nanomolar when measured in the presence of $^{125}$I-PYY; and (b) the binding of the compound to any other human Y-type receptor is characterized by a K$_i$ greater than 25 nanomolar when measured in the presence of $^{125}$I-PYY.

This invention provides a method of treating a feeding disorder in a subject which comprises administering to the subject an amount of a peptidyl compound which is a Y5 receptor agonist effective to increase the activity of the subject's Y5 receptor, wherein (a) the binding of the compound to the human Y5 receptor is characterized by a $K_i$ less than 0.1 nanomolar when measured in the presence of $^{125}$I-PYY; and (b) the binding of the compound to any other human Y-type receptor is characterized by a $K_i$ greater than 1 nanomolar when measured in the presence of $^{125}$I-PYY.

This invention provides a method of treating a feeding disorder in a subject which comprises administering to the subject an amount of a peptidyl compound which is a Y5 receptor agonist effective to increase the activity of the subject's Y5 receptor, wherein (a) the binding of the compound to the human Y5 receptor is characterized by a $K_i$ less than 0.01 nanomolar when measured in the presence of $^{125}$I-PYY; and (b) the binding of the compound to any other human Y-type receptor is characterized by a $K_i$ greater than 1 nanomolar when measured in the presence of $^{125}$I-PYY.

This invention provides an isolated nucleic acid encoding a Y5 receptor. This invention also provides an isolated Y5 receptor protein. This invention provides a vector comprising the above-described nucleic acid.

This invention provides a plasmid which comprises the regulatory elements necessary for expression of DNA in a mammalian cell operatively linked to the DNA encoding the human Y5 receptor as to permit expression thereof designated pcEXV-hY5 (ATCC Accession No. 75943).

This invention provides a plasmid which comprises the regulatory elements necessary for expression of DNA in a mammalian cell operatively linked to the DNA encoding the rat Y5 receptor as to permit expression thereof designated pcEXV-rY5 (ATCC Accession No. 75944).

This invention provides a mammalian cell comprising the above-described plasmid or vector.

This invention provides a nucleic acid probe comprising a nucleic acid of at least 15 nucleotides capable of specifically hybridizing with a unique sequence included within the sequence of a nucleic acid encoding a Y5 receptor.

This invention provides an antisense oligonucleotide having a sequence capable of specifically hybridizing to mRNA encoding a Y5 receptor so as to prevent translation of the mRNA.

This invention provides an antibody directed to a Y5 receptor.

This invention provides a pharmaceutical composition comprising an amount of the oligonucleotide effective to reduce activity of a human Y5 receptor by passing through a cell membrane and binding specifically with mRNA encoding a human Y5 receptor in the cell so as to prevent its translation and a pharmaceutically acceptable carrier capable of passing through a cell membrane.

This invention provides a pharmaceutical composition comprising an amount of an antagonist effective to reduce the activity of a human Y5 receptor and a pharmaceutically acceptable carrier.

This invention provides a pharmaceutical composition comprising an amount of an agonist effective to increase activity of a Y5 receptor and a pharmaceutically acceptable carrier.

This invention provides the above-described pharmaceutical composition which comprises an amount of the antibody effective to block binding of a ligand to the Y5 receptor and a pharmaceutically acceptable carrier.

This invention provides a transgenic nonhuman mammal expressing DNA encoding a human Y5 receptor.

This invention also provides a method for determining whether a ligand can specifically bind to a Y5 receptor which comprises contacting a cell transfected with and expressing DNA encoding the Y5 receptor with the ligand under conditions permitting binding of ligands to such receptor, detecting the presence of any such ligand specifically bound to the Y5 receptor, and thereby determining whether the ligand specifically binds to the Y5 receptor.

This invention provides a method for determining whether a ligand can specifically bind to a Y5 receptor which comprises preparing a cell extract from cells transfected with and expressing DNA encoding the Y5 receptor, isolating a membrane fraction from the cell extract, contacting the membrane fraction with the ligand under conditions permitting binding of ligands to such receptor, detecting the presence of the ligand specifically bound to the Y5 receptor, and thereby determining whether the ligand specifically binds to the Y5 receptor.

This invention provides a method for determining whether a ligand is a Y5 receptor agonist which comprises contacting a cell transfected with and expressing nucleic acid encoding a human Y5 receptor with the ligand under conditions permitting activation of the Y5 receptor, detecting an increase in Y5 receptor activity, and thereby determining whether the ligand is a human Y5 receptor agonist.

This invention provides a method for determining whether a ligand is a Y5 receptor antagonist which comprises contacting a cell transfected with and expressing DNA encoding a Y5 receptor with the ligand in the presence of a known Y5 receptor agonist, such as PYY or NPY, under conditions permitting the activation of the Y5 receptor, detecting a decrease in Y5 receptor activity, and thereby determining whether the ligand is a Y5 receptor antagonist.

This invention provides a method of screening a plurality of chemical compounds not known to bind to a Y5 receptor to identify a compound which specifically binds to the Y5 receptor, which comprises (a) contacting a cell transfected with and expressing DNA encoding the Y5 receptor with a compound known to bind specifically to the Y5 receptor; (b) contacting the preparation of step (a) with the plurality of compounds not known to bind specifically to the Y5 receptor, under conditions permitting binding of compounds known to bind the Y5 receptor; (c) determining whether the binding of the compound known to bind to the Y5 receptor is reduced in the presence of the compounds, relative to the binding of the compound in the absence of the plurality of compounds; and if so (d) separately determining the binding to the Y5 receptor of each compound included in the plurality of compounds, so as to thereby identify the compound which specifically binds to the Y5 receptor.

This invention provides a method of screening a plurality of chemical compounds not known to bind to a Y5 receptor to identify a compound which specifically binds to the Y5 receptor, which comprises (a) preparing a cell extract from cells transfected with and expressing DNA encoding the Y5 receptor, isolating a membrane fraction from the cell extract, contacting the membrane fraction with a compound known to bind specifically to the Y5 receptor; (b) contacting preparation of step (a) with the plurality of compounds not known to bind specifically to the Y5 receptor, under conditions permitting binding of compounds known to bind the Y5 receptor; (c) determining whether the binding of the compound known to bind to the Y5 receptor is reduced in the presence of the compounds, relative to the binding of the compound in the absence of the plurality of compounds; and if so (d) separately determining the binding to the Y5 receptor of each compound included in the plurality of compounds, so as to thereby identify the compound which specifically binds to the Y5 receptor.

This invention provides a method of screening a plurality of chemical compounds not known to activate a Y5 receptor to identify a compound which activates the Y5 receptor which comprises (a) contacting a cell transfected with and expressing the Y5 receptor with the plurality of compounds not known to bind specifically to the Y5 receptor, under conditions permitting activation of the Y5 receptor; (b) determining whether the activity of the Y5 receptor is increased in the presence of the compounds; and if so (c) separately determining whether the activation of the Y5 receptor is increased by each compound included in the plurality of compounds, so as to thereby identify the compound which activates the Y5 receptor.

This invention provides a method of screening a plurality of chemical compounds not known to activate a Y5 receptor to identify a compound which activates the Y5 receptor which comprises (a) preparing a cell extract from cells transfected with and expressing DNA encoding the Y5 receptor, isolating a membrane fraction from the cell extract, contacting the membrane fraction with the plurality of compounds not known to bind specifically to the Y5 receptor, under conditions permitting activation of the Y5 receptor; (b) determining whether the activity of the Y5 receptor is increased in the presence of the compounds; and if so (c) separately determining whether the activation of the Y5 receptor is increased by each compound included in the plurality of compounds, so as to thereby identify the compound which activates the Y5 receptor.

This invention provides a method of screening a plurality of chemical compounds not known to inhibit the activation of a Y5 receptor to identify a compound which inhibits the activation of the Y5 receptor, which comprises (a) contacting a cell transfected with and expressing the Y5 receptor with the plurality of compounds in the presence of a known Y5 receptor agonist, under conditions permitting activation of the Y5 receptor; (b) determining whether the activation of the Y5 receptor is reduced in the presence of the plurality of compounds, relative to the activation of the Y5 receptor in the absence of the plurality of compounds; and if so (c) separately determining the inhibition of activation of the Y5 receptor for each compound included in the plurality of compounds, so as to thereby identify the compound which inhibits the activation of the Y5 receptor.

This invention provides a method of screening a plurality of chemical compounds not known to inhibit the activation of a Y5 receptor to identify a compound which inhibits the activation of the Y5 receptor, which comprises (a) preparing a cell extract from cells transfected with and expressing DNA encoding the Y5 receptor, isolating a membrane fraction from the cell extract, contacting the membrane fraction with the plurality of compounds in the presence of a known Y5 receptor agonist, under conditions permitting activation of the Y5 receptor; (b) determining whether the activation of the Y5 receptor is reduced in the presence of the plurality of compounds, relative to the activation of the Y5 receptor in the absence of the plurality of compounds; and if so (c) separately determining the inhibition of activation of the Y5 receptor for each compound included in the plurality of compounds, so as to thereby identify the compound which inhibits the activation of the Y5 receptor.

This invention provides a method of screening drugs to identify drugs which specifically bind to a Y5 receptor on the surface of a cell which comprises contacting a cell transfected with and expressing DNA encoding a Y5 receptor with a plurality of drugs under conditions permitting binding of drugs to the Y5 receptor, determining those drugs which specifically bind to the transfected cell, and thereby identifying drugs which specifically bind to the Y5 receptor.

This invention provides a method of screening drugs to identify drugs which act as agonists of a Y5 receptor which comprises contacting a cell transfected with and expressing DNA encoding a Y5 receptor with a plurality of drugs under conditions permitting the activation of a functional Y5 receptor response, determining those drugs which activate such receptor in the cell, and thereby identify drugs which act as Y5 receptor agonists.

This invention provides a method of screening drugs to identify drugs which act as Y5 receptor antagonists which comprises contacting cells transfected with and expressing DNA encoding a Y5 receptor with a plurality of drugs in the presence of a known Y5 receptor agonist, such as PYY or NPY, under conditions permitting the activation of a functional Y5 receptor response, determining those drugs which inhibit the activation of the receptor in the mammalian cell, and thereby identifying drugs which act as Y5 receptor antagonists.

This invention provides a method of treating an abnormality in a subject, wherein the abnormality is alleviated by the inhibition of a Y5 receptor which comprises administering to a subject an effective amount of Y5 receptor antagonist.

This invention provides a method of treating an abnormality in a subject wherein the abnormality is alleviated by the activation of a Y5 receptor which comprises administering to a subject an effective amount of a Y5 receptor agonist.

This invention provides a method for diagnosing a predisposition to a disorder associated with the activity of a specific human Y5 receptor allele which comprises: a. obtaining DNA of subjects suffering from the disorder; performing a restriction digest of the DNA with a panel of restriction enzymes; c. electrophoretic-ally separating the resulting DNA fragments on a sizing gel; d. contacting the resulting gel with a nucleic acid probe capable of specifically hybridizing to DNA encoding a human Y5 receptor and labelled with a detectable marker; e. detecting labelled bands which have hybridized to the DNA encoding a human Y5 receptor labelled with a detectable marker to create a unique band pattern specific to the DNA of subjects suffering from the disorder; f. preparing DNA obtained for diagnosis by steps a–e; and g. comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method of preparing the isolated Y5 receptor which comprises: a. inserting nucleic acid encoding Y5 receptor in a suitable vector which comprises the regulatory elements necessary of expression of the nucleic acid operatively linked to the nucleic acid encoding a Y5 receptor; b. inserting the resulting vector in a suitable host cell so as to obtain a cell which produces the Y5 receptor; c. recovering the receptor produced by the resulting cell; and d. purifying the receptor so recovered.

BRIEF DESCRIPTION OF THE FIGURES

FIG. 3 Nucleotide sequence of the rat hypothalamic Y5 cDNA clone (Seq. I.D. No 1). Initiation and stop codons are underlined. Only partial 5' and 3' untranslated sequences are shown.

FIG. 4 Corresponding amino acid sequence of the rat hypothalamic Y5 cDNA clone (Seq. I.D. No. 2).

FIG. 5 Nucleotide sequence of the human hippocampal Y5 cDNA clone (Seq. I.D. No. 3). Initiation and stop codons are underlined. Only partial 5' and 3' untranslated sequences are shown.

FIG. 6 Corresponding amino acid sequence of the human hippocampal Y5 cDNA clone(Seq. I.D. No. 4).

FIGS. 7A–7E. Comparison of coding nucleotide sequences between rat hypothalamic Y5 (top row) and human hippocampal Y5 (bottom row) cDNA clones (84.1% nucleotide identity).

FIGS. 7F–7G. Comparison of deduced amino acid sequences between rat hypothalamic Y5 (top row) and human hippocampal Y5 (bottom row) cDNA clones (87.2% overall and 98.8% transmembrane domain identities).

FIGS. 8A–8C Comparison of the human Y5 receptor deduced amino acid sequence with those of the human Y1, Y2, Y4 sequences. Solid bars, the seven putative membrane-spanning domains (TM I-VII). Shading, identities between receptor sequences.

FIGS. 13A–13H Schematic diagrams of coronal sections through the rat brain, illustrating the distribution of NPY Y5 receptor mRNA, as visualized microscopically in sections dipped in liquid emulsion. The sections are arranged from rostral (A) to caudal (H). Differences in silver grain density over individual neurons in a given area are indicated by the hatching gradient. The full definitions for the abbreviations are as follows:

Aco=anterior cortical amygdaloid nucleus;
AD=anterodorsal thalamic nucleus;
APT=anterior pretectal nucleus;
Arc=arcuate hypothalamic nucleus;
BLA=basolateral amygdaloid nucleus anterior;
CA3=field CA3 of Ammon's horn, hippocampus;
CeA=central amygdaloid nucleus;
Cg=cingulate cortex;
CL=centrolateral thalamic nucleus;
CM=central medial thalamic nucleus
DG=dentate gyrus, hippocampus;
DMH=dorsomedial hypothalamic nucleus;
DR=dorsal raphe;
GiA=gigantocellular reticular nucleus, alpha;
HDB=nucleus horizontal limb diagonal band;
InG=intermediate gray layer superior colliculus;
LC=locus coeruleus;
LH=lateral hypothalamic area;
MePV=medial amygdaloid nucleus, posteroventral;
MVe=medial vestibular nucleus;
MHb=medial habenular nucleus;
MPN=medial preoptic nucleus;
PAG=periaqueductal gray;
PaS=parasubiculum;
PC=paracentral thalamic nucleus;
PCRtA=parvocellular reticular nucleus, alpha;
Pe=periventricular hypothalamic nucleus;
PrS=presubiculum;
PN=pontine nuclei;
PVH=paraventricular hypothalamic nucleus;
PVHmp=paraventricular hypothalamic nucleus, medial parvicellular part
PVT=paraventricular thalamic nucleus;
Re=reunions thalamic nucleus;

RLi=rostral linear nucleus raphe;

RSG=retrosplenial cortex;

SCN=suprachiasmatic nucleus;

SNc=substantia nigra, pars compacta; and

SON=supraoptic nucleus.

FIG. 14 Partial Nucleotide sequence of the canine Y5 cDNA clone beginning immediately upstream of TM III to the stop codon (underlined). (Seq. I.D. No 5). Only partial untranslated sequences are shown.

FIG. 15 Corresponding amino acid sequence of the canine Y5 cDNA clone (Seq. I.D. No. 6).

Figure 16A:
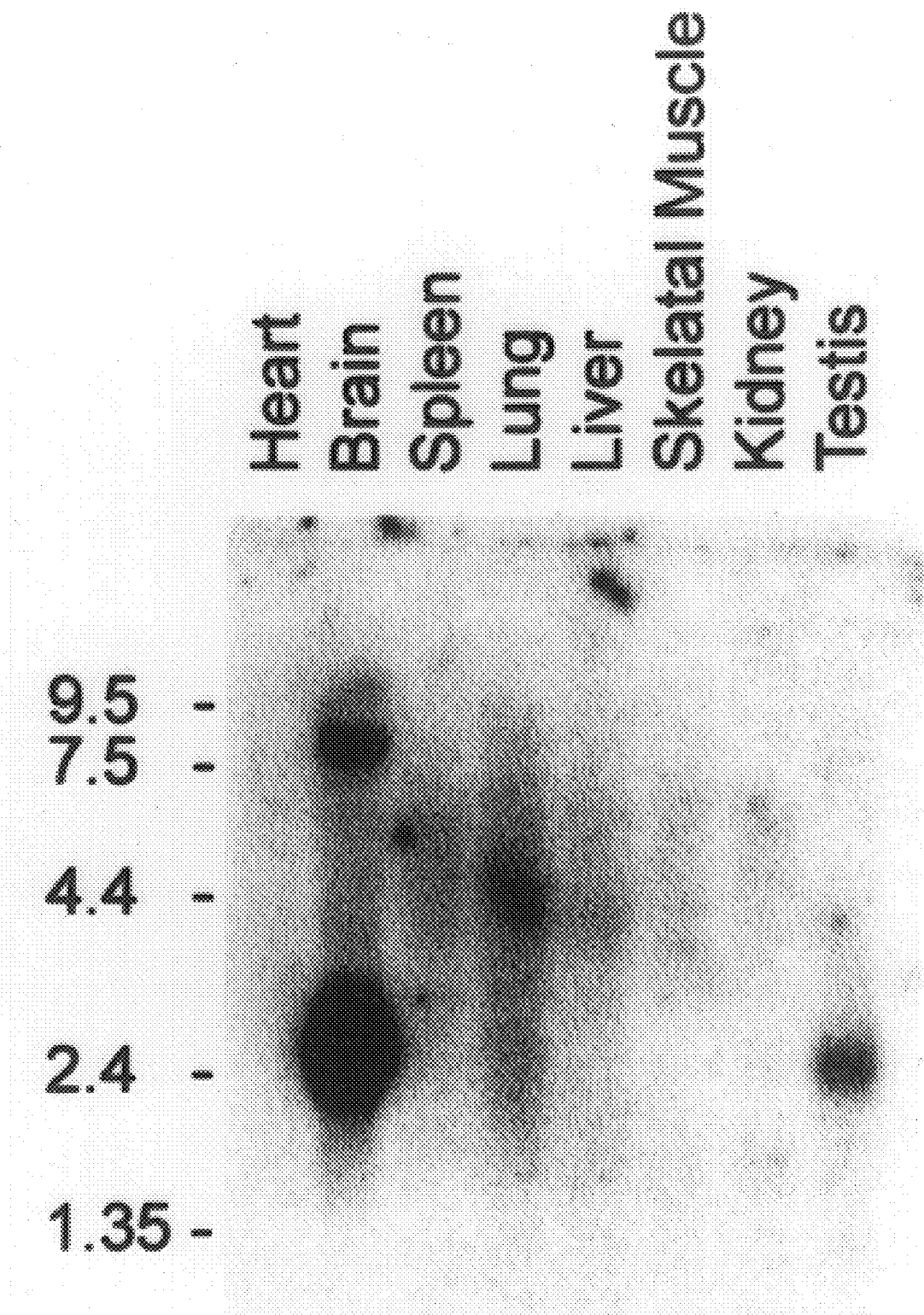
Figure 16B:
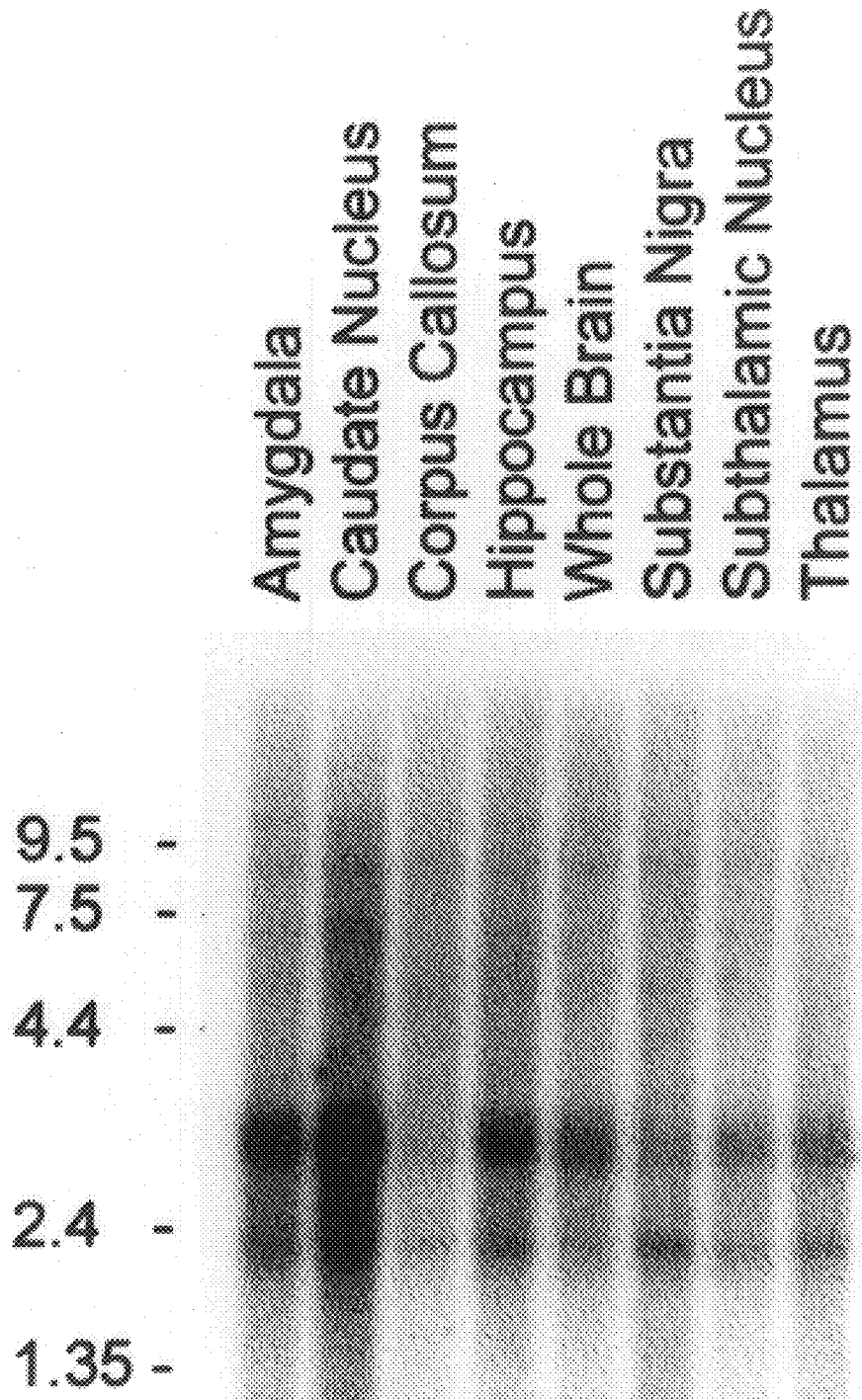
Figure 16C:
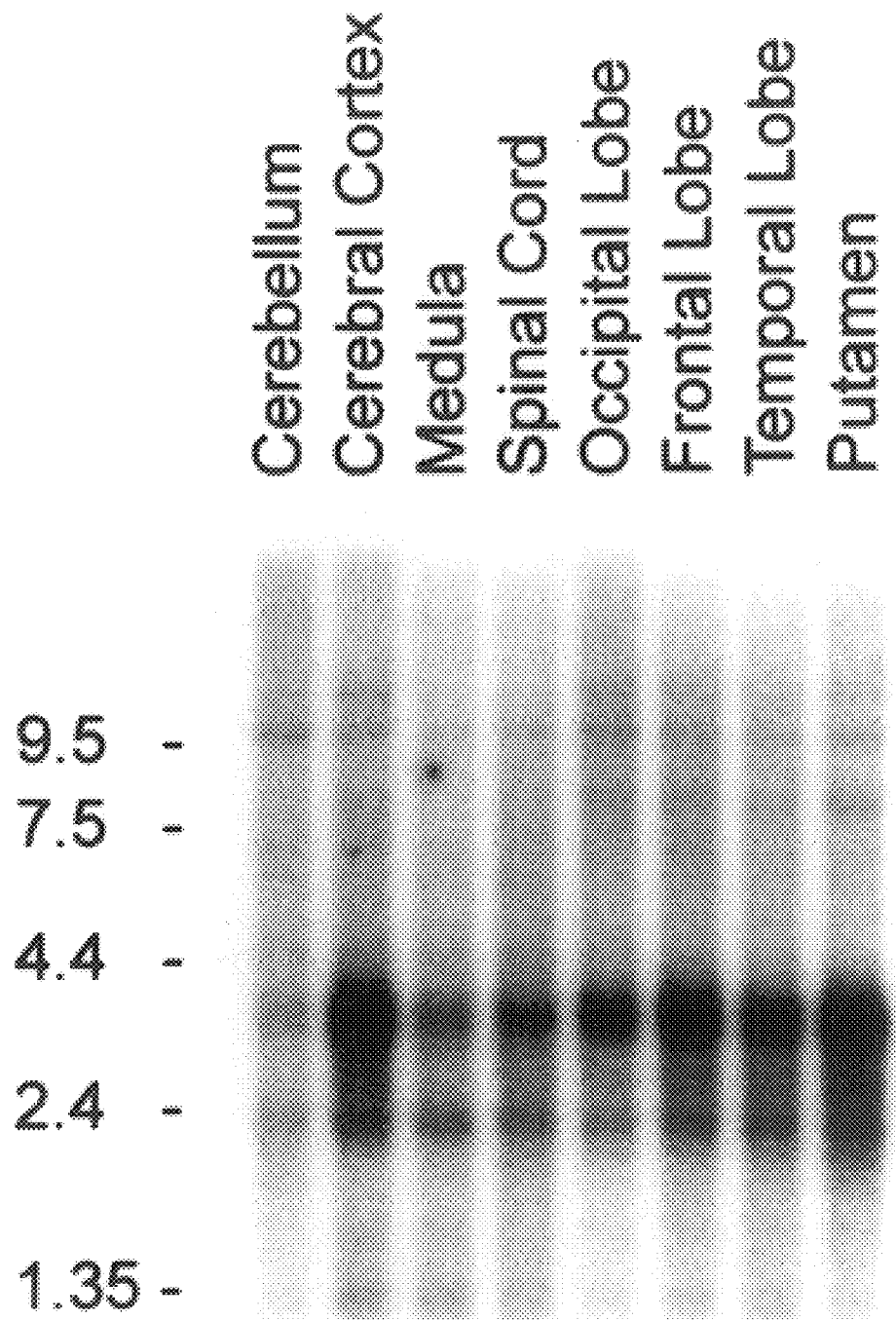

FIGS. 16A–16C A. Northern blot analysis of various rat tissues. B. Northern blot analysis of various human brain areas: amygdala, caudate nucleus, corpus callosum, hippocampus, whole brain, substantia nigra, subthalamic nucleus, and thalamus. C. Northern blot analysis of various additional human brain areas: cerebellum, cerebral cortex, medulla, spinal cord, occipital lobe, frontal lobe, temporal lobe, and putamen. Hybridization was done under conditions of high stringency, as described in Experimental Details.

Figure 17A:
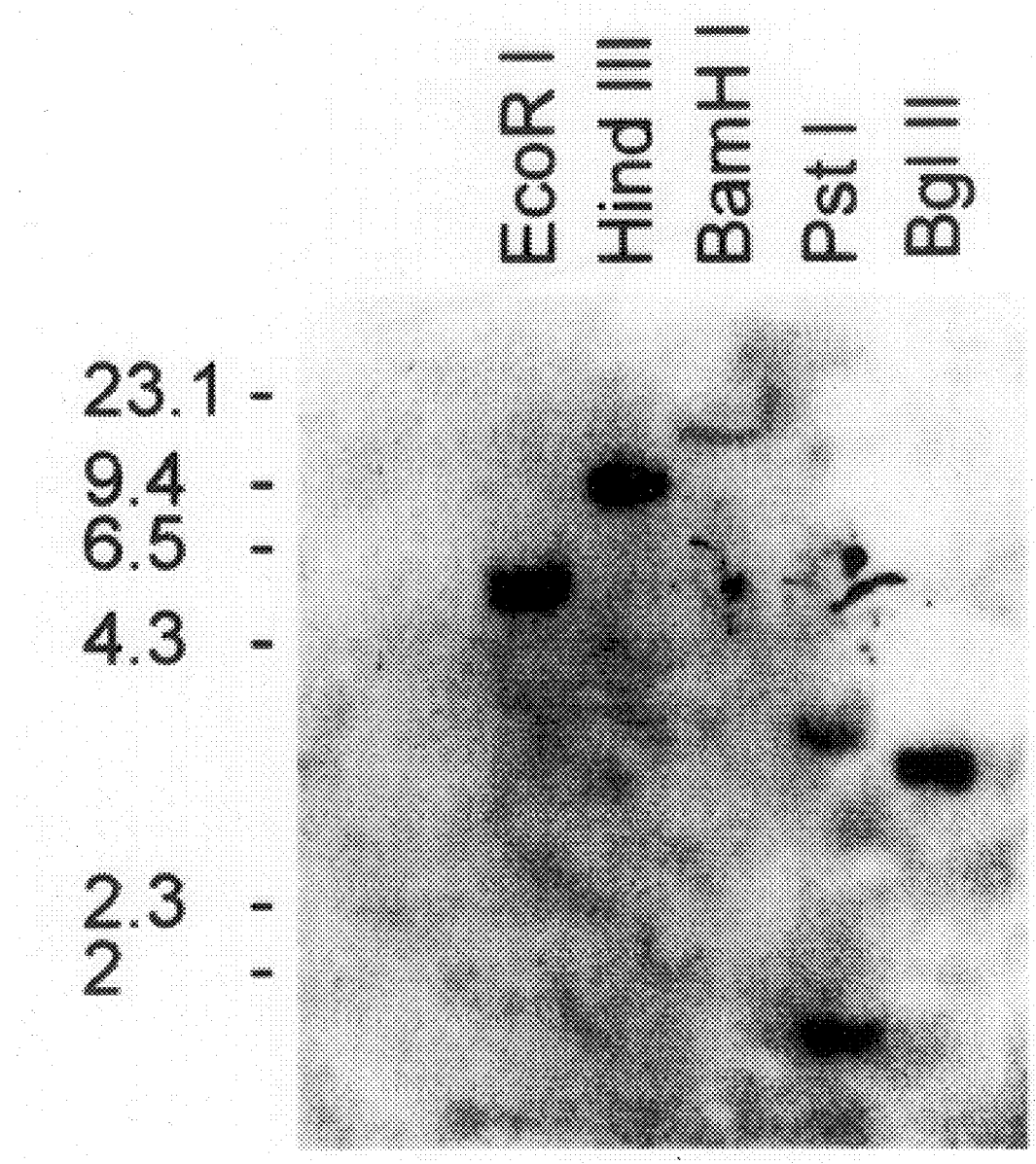
Figure 17B:
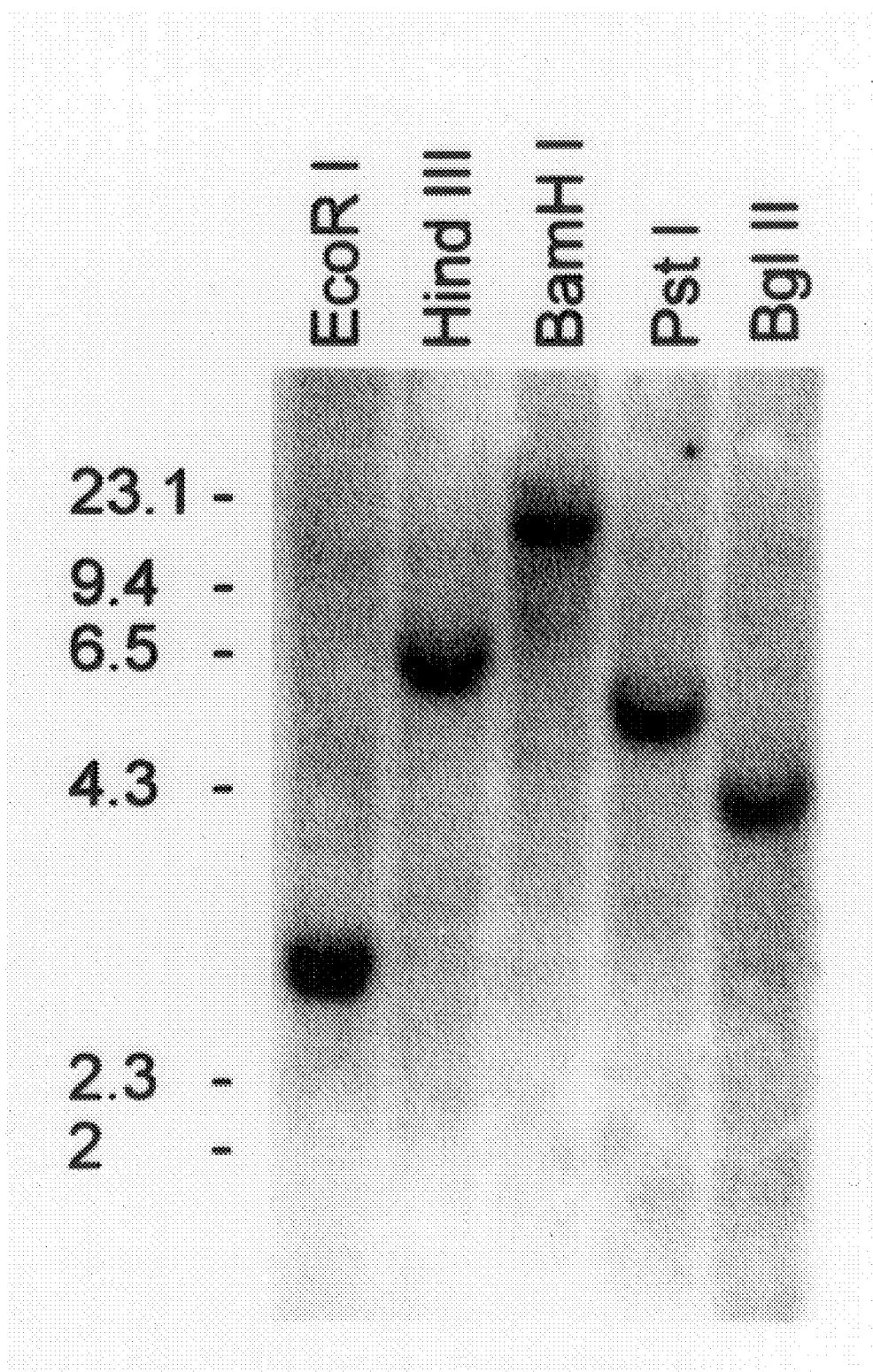

FIGS. 17A–17B Southern blot analysis of human(A) or rat(B) genomic DNA encoding the Y5 receptor subtype. Hybridization was done under conditions of high stringency, as described in Experimental Details.

Figure 18:
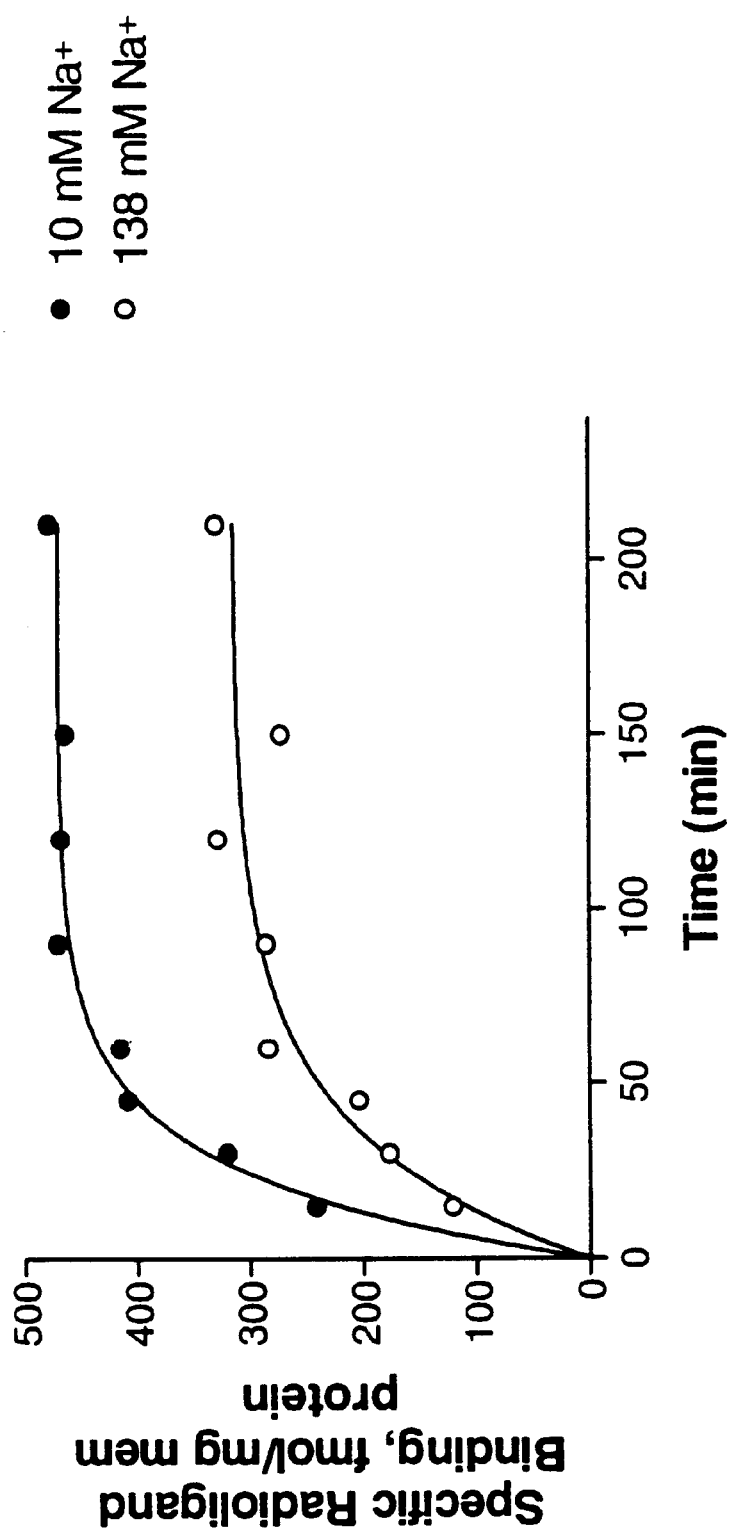

FIG. 18 Time course for equilibrium binding of $^{125}$I-Leu$^{31}$, Pro$^{34}$-PYY to the rat Y5 receptor. Membranes were incubated with 0.08 nM radioligand at room temperature for the length of time indicated in binding buffer containing either 10 mM Na+ or 138 mM Na+.

Figure 19:
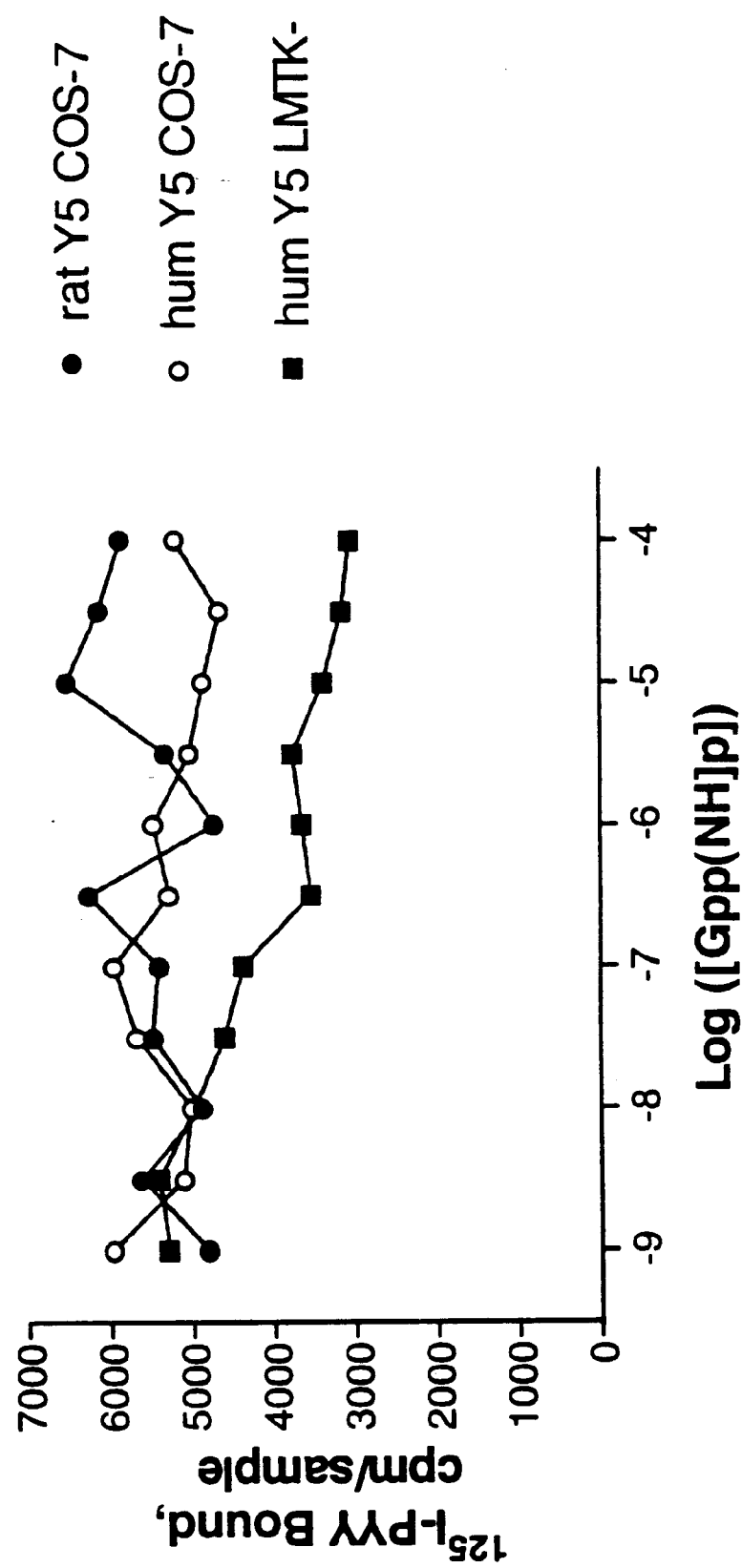

FIG. 19 Guanine Nucleotide Modulation of Y5 Peptide Binding. Human or rat Y5 receptors transiently expressed in COS-7 cell membranes, or human Y5 receptors stably expressed in LM(tk–) cell membranes, were incubated with 0.08 nM $^{125}$I-PYY and increasing concentrations of Gpp (NH)p as indicated under standard binding assay conditions. Radioligand binding is reported as cpm, efficiency=0.8. For the human Y5 in LM(tk–) (0.007 mg membrane protein/sample), the maximum Δ cpm=–2343. Given a specific activity of 2200 Ci/mmol, the change in radioligand binding is therefore calculated to be –0.6 fmol/0.007 mg protein=–85 fmol/mg membrane protein.

Figure 20:
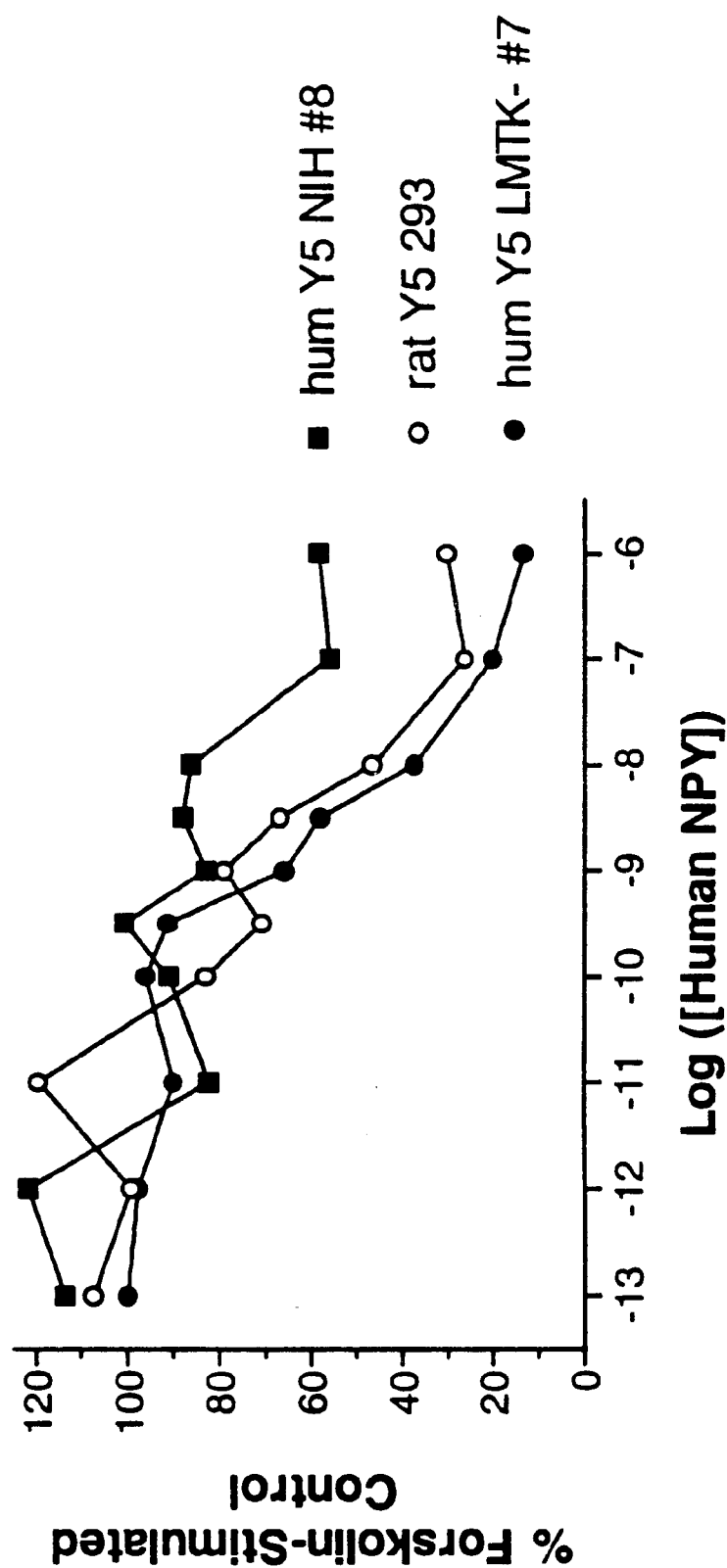

FIG. 20 NPY-Dependent Inhibition of Forskolin Stimulated cAMP Accumulation by Cloned Y5 Receptors. Intact cells stably transfected with human or rat Y5 receptors were incubated with forskolin plus a range of human NPY concentrations as indicated. A representative experiment is shown for each receptor system (n≧2).

FIGS. 21A–21D Calcium Mobilization: Fura-2 Assay. Cloned human Y-type receptors in the host cells indicated were screened for intracellular calcium mobilization in response to NPY and related peptides. Representative calcium transients are shown for each receptor system.

A. Human Y1 receptor

B. Human Y2 receptor

C. Human Y4 receptor

D. Human Y5 receptor

FIGS. 22A–22C Structures of Y5-selective compounds. The structures of the compounds evaluated at the human Y-type receptors are given.

DETAILED DESCRIPTION OF THE INVENTION

Throughout this application, the following standard abbreviations are used to indicate specific nucleotide bases:

C=cytosine A=adenine

T=thymine G=guanine

Furthermore, the term "agonist" is used throughout this application to indicate any peptide or non-peptidyl compound which increases the activity of any of the receptors of the subject invention. The term "antagonist" is used throughout this application to indicate any peptide or non-peptidyl compound which decreases the activity of any of the receptors of the subject invention.

The activity of a G-protein coupled receptor such as a Y5 receptor may be measured using any of a variety of appropriate functional assays in which activation of the receptor in question results in an observable change in the level of some second messenger system, including but not limited to adenylate cyclase, calcium mobilization, inositol phospholipid hydrolysis or guanylyl cyclase.

This invention provides a method of modifying feeding behavior of a subject which comprises administering to the subject an amount of a compound which is a Y5 receptor agonist or antagonist effective to increase or decrease the consumption of food by the subject so as to thereby modify feeding behavior of the subject. In one embodiment, the compound is a Y5 receptor antagonist and the amount is effective to decrease the consumption of food by the subject. In a further embodiment, the compound is administered in combination with food. In another embodiment the compound is a Y5 receptor agonist and the amount is effective to increase the consumption of food by the subject. In a further embodiment the compound is administered in combination with food. The subject may be a vertebrate, a mammal, a human or a canine subject.

This invention provides a method of treating a feeding disorder in a subject which comprises administering to the subject an amount of a non-peptidyl compound which is a Y5 receptor antagonist effective to inhibit the activity of the subject's Y5 receptor, wherein the binding of the compound to the human Y5 receptor is characterized by a $K_i$ less than 100 nanomolar when measured in the presence of $^{125}$I-PYY. In one embodiment the compound has a $K_i$ less than 50 nanomolar. In another embodiment, the compound has a $K_i$ less than 10 nanomolar. In a further embodiment, the binding of the compound to any other human Y-type receptor is characterized by a $K_i$ greater than 10 nanomolar when measured in the presence of $^{125}$I-PYY. In another embodiment, the binding of the compound to any other human Y-type receptor is characterized by a $K_i$ greater than 50 nanomolar. In another embodiment, the binding of the compound is characterized by a $K_i$ greater than 100 nanomolar. In one embodiment, the compound binds to the human Y5 receptor with an affinity greater than ten-fold higher than the affinity with which the compound binds to any other human Y-type receptor. In a further embodiment the compound binds to the human Y5 receptor with an affinity greater than ten-fold higher than the affinity with which the compound binds to each of the human Y1, human Y2 and human Y4 receptors. The feeding disorder may be obesity or bulimia. The subject may be a vertebrate, a mammal, a human or a canine subject.

This invention provides a method of treating a feeding disorder in a subject which comprises administering to the subject an amount of a peptidyl compound which is a Y5 receptor antagonist affective to inhibit the activity of the subject's Y5 receptor, wherein the compound's binding to the human Y5 receptor is characterized by a $K_i$ less than 10 nanomolar when measured in the presence of $^{125}$I-PYY. In one embodiment, the compound's binding is characterized by a $K_i$ less than 1 nanomolar. In another embodiment, the compound's binding to any other human Y-type receptor is characterized by a $K_i$ greater than 10 nanomolar when measured in the presence of $^{125}$I-PYY. In another embodiment the compound's binding to each of the human Y1, human Y2, and human Y4 receptors is characterized by a $K_i$ greater than 10 nanomolar when measured in the presence of $^{125}$I-PYY. In a further embodiment, the compound's binding to any other human Y-type receptor is characterized by a $K_i$ greater than 50 nanomolar. In another embodiment the compound's binding to any other human Y-type receptor is characterized by a $K_i$ greater than 100 nanomolar. In one embodiment, the compound binds to the human Y5 receptor with an affinity greater than ten-fold higher than the affinity with which the compound binds to any other human Y-type receptor. In another embodiment, the compound binds to the human Y5 receptor with an affinity greater than ten-fold higher than the affinity with which the compound binds to each of the human Y1, human Y2, and human Y4 receptors. The feeding disorder may be obesity or bulimia. The subject may be a vertebrate, a mammal, a human, or a canine subject.

This invention provides a method of treating a feeding disorder in a subject which comprises administering to the subject an amount of a non-peptidyl compound which is a Y5 receptor agonist affective to increase the activity of the subject's Y5 receptor, wherein (a) the binding of the compound to the human Y5 receptor is characterized by a $K_i$ less than 100 nanomolar when measured in the presence of $^{125}$I-PYY; and (b) the binding of the compound to any other human Y-type receptor is characterized by a $K_i$ greater than 1000 nanomolar when measured in the presence of $^{125}$I-PYY. In one embodiment, the binding of the compound to the human Y5 receptor is characterized by a $K_i$ less than 10 nanomolar.

This invention provides a method of treating a feeding disorder in a subject which comprises administering to the subject an amount of a non-peptidyl compound which is a Y5 receptor agonist effective to increase the activity of the subject's Y5 receptor, wherein (a) the binding of the compound to the human Y5 receptor is characterized by a $K_i$ less than 1 nanomolar when measured in the presence in $^{125}$I-PYY; and (b) the compound's binding to any other human Y-type receptor is characterized by a $K_i$ greater than 100 nanomolar when measured in the presence of $^{125}$I-PYY. In one embodiment, the compound binds to the human Y5 receptor with an affinity greater than ten-fold higher than the affinity with which the compound binds to any other human Y-type receptor. In another embodiment, the compound binds to the human Y5 receptor with an affinity greater than ten-fold higher than the affinity with which the compound binds to each of the human Y1, human Y2, and human Y4 receptors. The feeding disorder may be anorexia. The subject may be a vertebrate, a mammal, a human, or a canine subject.

This invention provides a method of treating a feeding disorder in a subject which comprises administering to the subject an amount of a peptidyl compound which is a Y5 receptor agonist effective to increase the activity of the subject's Y5 receptor, wherein (a) the binding of the compound to the human Y5 receptor is characterized by a $K_i$ less than 1 nanomolar when measured in the presence of $^{125}$I-PYY; and (b) the binding of the compound to any other human Y-type receptor is characterized by a $K_i$ greater than 25 nanomolar when measured in the presence of $^{125}$I-PYY.

This invention provides a method of treating a feeding disorder in a subject which comprises administering to the subject an amount of a peptidyl compound which is a Y5 receptor agonist effective to increase the activity of the subject's Y5 receptor, wherein (a) the binding of the compound to the human Y5 receptor is characterized by a $K_i$ less than 0.1 nanomolar when measured in the presence of $^{125}$I-PYY; and (b) the binding of the compound to any other human Y-type receptor is characterized by a $K_i$ greater than 1 nanomolar when measured in the presence of $^{125}$I-PYY. In one embodiment, the binding of the agonist to any other human Y-type receptor is characterized by a $K_i$ greater than 10 nanomolar.

This invention provides a method of treating a feeding disorder in a subject which comprises administering to the subject an amount of a peptidyl compound which is a Y5 receptor agonist effective to increase the activity of the subject's Y5 receptor, wherein (a) the binding of the compound to the human Y5 receptor is characterized by a $K_i$ less than 0.01 nanomolar when measured in the presence of $^{125}$I-PYY; and (b) the bonding of the compound to any other human Y-type receptor is characterized by a $K_i$ greater than 1 nanomolar when measured in the presence of $^{125}$I-PYY. In one embodiment, the compound binds to the human Y5 receptor with an affinity greater than ten-fold higher than the affinity with which the compound binds to any other human Y-type receptor. In another embodiment, the compound binds to the human Y5 receptor with an affinity greater than ten-fold higher than the affinity with which the compound binds to each of the human Y1, human Y2, and human Y4 receptors. In one embodiment, the feeding disorder is anorexia. The subject may be a vertebrate, a mammal, a human, or a canine subject.

This invention provides an isolated nucleic acid encoding a Y5 receptor. In an embodiment, the Y5 receptor is a vertebrate or a mammalian Y5 receptor. In one embodiment, the Y5 receptor is a human Y5 receptor. In an embodiment, the isolated nucleic acid encodes a receptor being characterized by an amino acid sequence in the transmembrane region, which amino acid sequence has 60% homology or higher to the amino acid sequence in the transmembrane region of the human Y5 receptor shown in FIG. 6. In another embodiment, the Y5 receptor has substantially the same amino acid sequence as described in FIG. 4. In another embodiment, the Y5 receptor has substantially the same amino acid sequence as described in FIG. 6.

Figure 4:
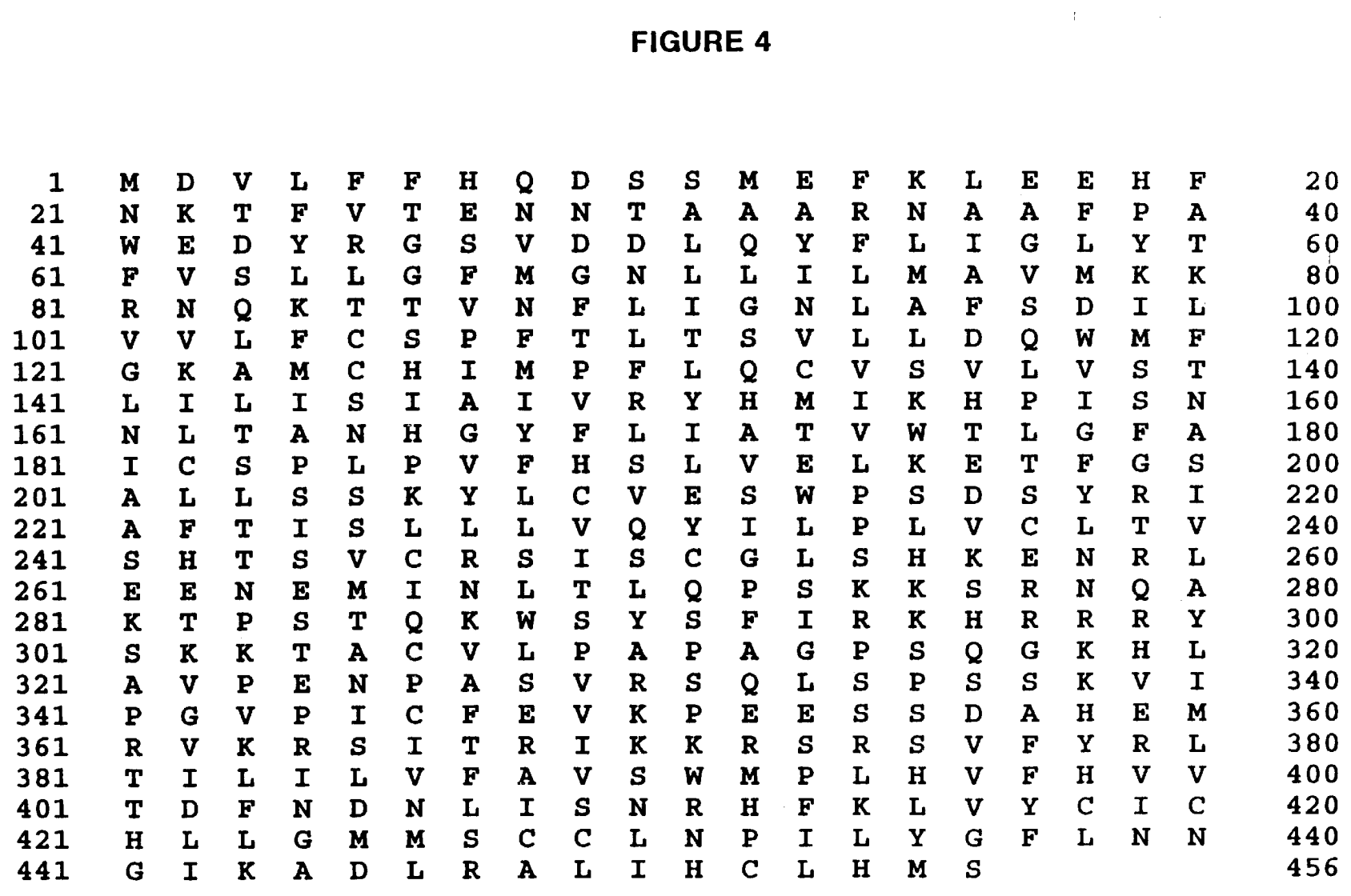

This invention provides the above-described isolated nucleic acid, wherein the nucleic acid is a DNA. In an embodiment, the DNA is a cDNA. In another embodiment, the DNA is a genomic DNA. In still another embodiment, the nucleic acid is RNA. In a separate embodiment, the nucleic acid encodes a human Y5 receptor. In an embodiment, the human Y5 receptor has the amino acid sequence as described in FIG. 6. In another embodiment, the nucleic acid encodes a rat Y5 receptor. In an embodiment, the rat Y5 receptor has the amino acid sequence as shown in FIG. 4. In another embodiment, the nucleic acid encodes a canine Y5 receptor. In an embodiment, the canine Y5 receptor has the amino acid sequence shown in FIG. 15.

Figure 6:
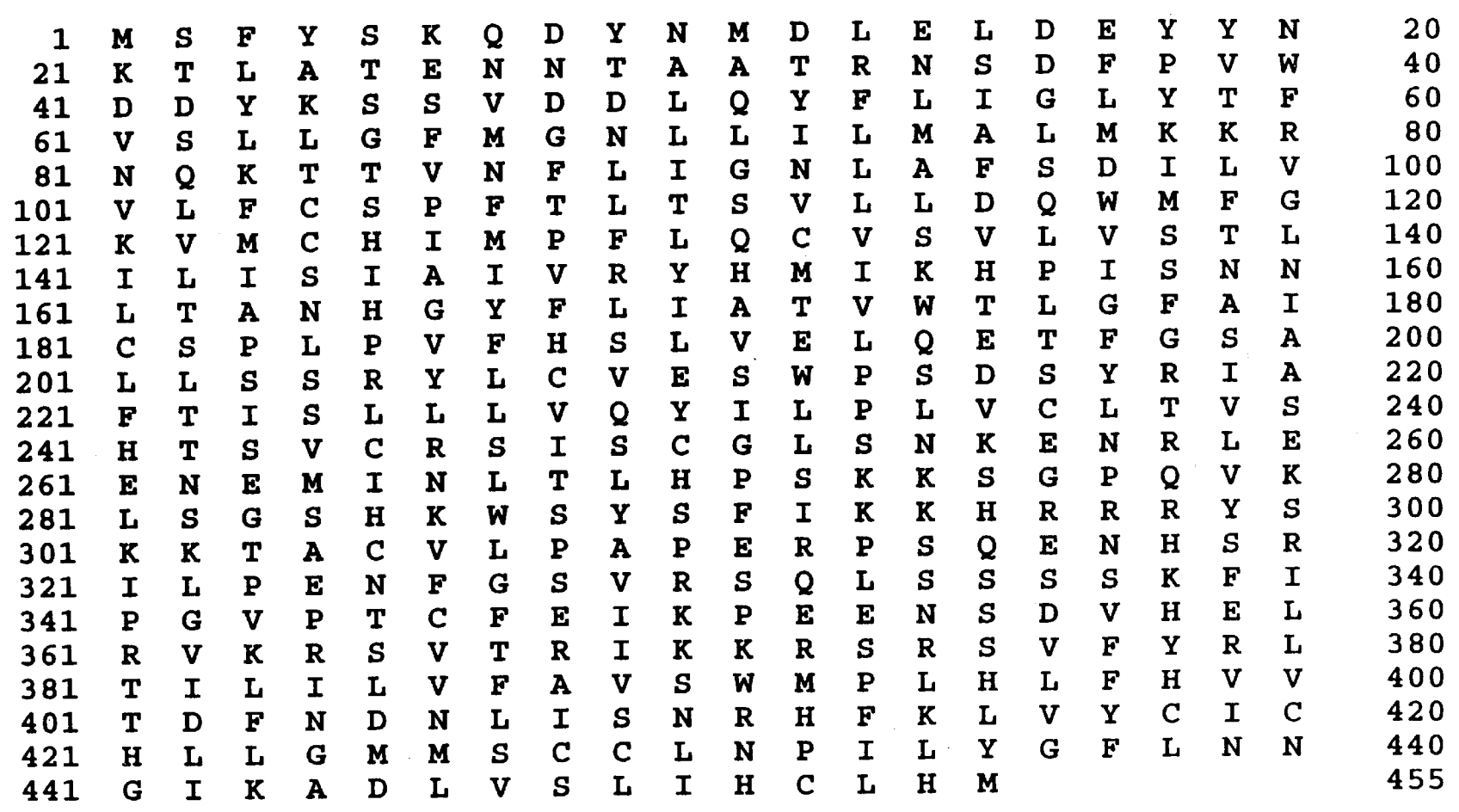

This invention further provides DNA which is degenerate with any of the DNA shown in FIGS. 3, 5 and 14, wherein the DNA encodes Y5 receptors having the amino acid sequences shown in FIGS. 4, 6, and 15, respectively.

This invention also encompasses DNAs and cDNAs which encode amino acid sequences which differ from those of Y5 receptor, but which should not produce phenotypic changes. Alternatively, this invention also encompasses DNAs and cDNAs which hybridize to the DNA and cDNA of the subject invention. Hybridization methods are well known to those of skill in the art.

The DNA of the subject invention also include DNA coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These nucleic acids include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The nucleic acids described and claimed herein are useful for the information which they provide concerning the amino acid sequence of the polypeptide and as products for the large scale synthesis of the polypeptide by a variety of recombinant techniques. The nucleic acid is useful for generating new cloning and expression vectors, transformed and transfected prokaryotic and eukaryotic host cells, and new and useful methods for cultured growth of such host cells capable of expression of the polypeptide and related products.

In a separate embodiment, the nucleic acid encodes a rat Y5 receptor. In another embodiment, the rat Y5 receptor has the amino acid sequence shown in FIG. 4.

This invention also provides an isolated Y5 receptor protein. In one embodiment, the Y5 receptor protein is a human Y5 receptor protein. In another embodiment, the human Y5 receptor protein has the amino acid sequence as shown in FIG. 6. In a further embodiment, the Y5 receptor protein is a rat Y5 receptor protein. In another embodiment, the rat Y5 receptor protein has the amino acid sequence as shown in FIG. 4. In another embodiment, the Y5 receptor protein is a canine Y5 receptor protein. In a further embodiment, the canine Y5 receptor protein has the amino acid sequence as shown in FIG. 15.

This invention provides a vector comprising the above-described nucleic acid.

Vectors which comprise the isolated nucleic acid described hereinabove also are provided. Suitable vectors comprise, but are not limited to, a plasmid or a virus. These vectors may be transformed into a suitable host cell to form a host cell vector system for the production of a polypeptide having the biological activity of a Y5 receptor.

This invention provides the above-described vector adapted for expression in a bacterial cell which further comprises the regulatory elements necessary for expression of the nucleic acid in the bacterial cell operatively linked to the nucleic acid encoding the Y5 receptor as to permit expression thereof.

This invention provides the above-described vector adapted for expression in a yeast cell which comprises the regulatory elements necessary for expression of the nucleic acid in the yeast cell operatively linked to the nucleic acid encoding the Y5 receptor as to permit expression thereof.

This invention provides the above-described vector adapted for expression in an insect cell which comprises the regulatory elements necessary for expression of the nucleic acid in the insect cell operatively linked to the nucleic acid encoding the Y5 receptor as to permit expression thereof.

In an embodiment, the vector is adapted for expression in a mammalian cell which comprises the regulatory elements necessary for expression of the DNA in the mammalian cell operatively linked to the DNA encoding the mammalian Y5 receptor as to permit expression thereof.

In an embodiment, the vector is adapted for expression in a mammalian cell which comprises the regulatory elements necessary for expression of the DNA in the mammalian cell operatively linked to the DNA encoding the canine Y5 receptor as to permit expression thereof.

In a further embodiment, the vector is adapted for expression in a mammalian cell which comprises the regulatory elements necessary for expression of the DNA in the mammalian cell operatively linked to the DNA encoding the human Y5 receptor as to permit expression thereof.

In a still further embodiment, the plasmid is adapted for expression in a mammalian cell which comprises the regulatory elements necessary for expression of the DNA in the mammalian cell operatively linked to the DNA encoding the rat Y5 receptor as to permit expression thereof.

In a still further embodiment, the plasmid is adapted for expression in a mammalian cell which comprises the regulatory elements necessary for expression of the DNA in the mammalian cell operatively linked to the DNA encoding the canine Y5 receptor as to permit expression thereof.

This invention provides the above-described plasmid adapted for expression in a mammalian cell which comprises the regulatory elements necessary for expression of DNA in a mammalian cell operatively linked to the DNA encoding the mammalian Y5 receptor as to permit expression thereof.

This invention provides a plasmid which comprises the regulatory elements necessary for expression of DNA in a mammalian cell operatively linked to the DNA encoding the human Y5 receptor as to permit expression thereof designated pcEXV-hY5 (ATCC Accession No. 75943).

This plasmid (pcEXV-hY5) was deposited on Nov. 4, 1994 with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 75943.

This invention provides a plasmid which comprises the regulatory elements necessary for expression of DNA in a mammalian cell operatively linked to the DNA encoding the rat Y5 receptor as to permit expression thereof designated pcEXV-rY5 (ATCC Accession No. 75944).

This plasmid (pcEXV-rY5) was deposited on Nov. 4, 1994 with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. CRL 75944.

This invention provides a plasmid designated Y5-bd-5 (ATCC Accession No. 97355). This invention also provides a plasmid designated Y5-bd-8 (ATCC Accession No. 97354). These plasmids were deposited on Dec. 1, 1995 with the American Type Culture Collection (ATCC), 10801 University Boulevard, Manassas, Va. 20110-2209, U.S.A. under the provisions of the Budapest Treaty for the International Recognition of the Deposit of Microorganisms for the Purposes of Patent Procedure and were accorded ATCC Accession Nos. 97355 and 97354, respectively.

This invention provides a baculovirus designated hY5-BB3 (ATCC Accession No. VR-2520). This baculovirus was deposited on Nov. 15, 1995 with the American Type Culture Collection (ATCC), 10801 University Boulevard, Manassas, Va. 20110-2209, U.S.A. under the provisions of the Budapest Treaty for the International Recognition of the Deposit of Microorganisms for the Purposes of Patent Procedure and was accorded ATCC Accession No.

This invention provides a mammalian cell comprising the above-described plasmid or vector. In an embodiment, the mammalian cell is a COS-7 cell.

In another embodiment, the mammalian cell is a 293 human embryonic kidney cell designated 293-rY5-14 (ATCC Accession No. CRL 11757).

This cell (293-rY5-14) was deposited on Nov. 4, 1994 with the American Type Culture Collection (ATCC), 10801 University Boulevard, Manassas, Va. 20110-2209, U.S.A. under the provisions of the Budapest Treaty for the International Recognition of the Deposit of Microorganisms for the Purposes of Patent Procedure and was accorded ATCC Accession No. CRL 11757.

In a further embodiment, the mammalian cell is a mouse fibroblast (tk−) cell, containing the plasmid pcEXV-hY5 and designated L-hY5-7 (ATCC Accession No. CRL-11995). In another embodiment, the mammalian cell is a mouse embryonic NIH-3T3 cell containing the plasmid pcEXV-hY5 and designated N-hY5-8 (ATCC Accession No. CRL-11994). These cells were deposited on Nov. 15, 1995 with the American Type Culture Collection (ATCC) 10801 University Boulevard, Manassas, Va., 20110-2209, U.S.A. under the provisions ot the Budapest Treaty for the International Recgonition of the Deposit of Microorganisms for the Purposes of Patent Procedure, and were accorded ATCC Accession Nos. CRL-11995 and CRL-11994, respectively.

This invention provides a nucleic acid probe comprising a nucleic acid molecule of at least 15 nucleotides capable of specifically hybridizing with a unique sequence included within the sequence of a nucleic acid molecule encoding a Y5 receptor. In an embodiment, the nucleic acid is DNA.

This nucleic acid produced can either be DNA or RNA. As used herein, the phrase "specifically hybridizing" means the ability of a nucleic acid to recognize a nucleic acid sequence complementary to its own and to form double-helical segments through hydrogen bonding between complementary base pairs.

This nucleic acid of at least 15 nucleotides capable of specifically hybridizing with a sequence of a nucleic acid encoding the human Y5 receptors can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes the Y5 receptor into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the DNA which encodes the Y5 receptor downstream of a bacteriophage promoter such as T3, T7 or SP6. Large amounts of RNA probe may be produced by incubating the labeled nucleotides with the linearized fragment where it contains an upstream promoter in the presence of the appropriate RNA polymerase.

This invention also provides a nucleic acid of at least 15 nucleotides capable of specifically hybridizing with a sequence of a nucleic acid which is complementary to the mammalian nucleic acid encoding a Y5 receptor. This nucleic acid may either be a DNA or RNA molecule.

This invention provides an antisense oligonucleotide having a sequence capable of specifically hybridizing to mRNA encoding a Y5 receptor so as to prevent translation of the mRNA.

This invention provides an antisense oligonucleotide having a sequence capable of specifically hybridizing to the genomic DNA of a Y5 receptor.

This invention provides an antisense oligonucleotide of a Y5 receptor comprising chemical analogues of nucleotides.

This invention provides an antibody directed to a Y5 receptor. This invention also provides an antibody directed to a human Y5 receptor.

This invention provides a monoclonal antibody directed to an epitope of a human Y5 receptor present on the surface of a Y5 receptor expressing cell.

This invention provides a pharmaceutical composition comprising an amount of the oligonucleotide effective to reduce activity of a human Y5 receptor by passing through a cell membrane and binding specifically with mRNA encoding a human Y5 receptor in the cell so as to prevent its translation and a pharmaceutically acceptable carrier capable of passing through a cell membrane. In an embodiment, the oligonucleotide is coupled to a substance which inactivates mRNA. In another embodiment, the substance which inactivates mRNA is a ribozyme.

This invention provides the above-described pharmaceutical composition, wherein the pharmaceutically acceptable carrier capable of passing through a cell membrane comprises a structure which binds to a receptor specific for a selected cell type and is thereby taken up by cells of the selected cell type.

This invention provides a pharmaceutical composition comprising an amount of an antagonist effective to reduce the activity of a human Y5 receptor and a pharmaceutically acceptable carrier.

This invention provides a pharmaceutical composition comprising an amount of an agonist effective to increase activity of a Y5 receptor and a pharmaceutically acceptable carrier.

This invention provides the above-described pharmaceutical composition which comprises an amount of the antibody effective to block binding of a ligand to the Y5 receptor and a pharmaceutically acceptable carrier.

As used herein, "pharmaceutically acceptable carriers" means any of the standard pharmaceutically acceptable carriers. Examples include, but are not limited to, phosphate buffered saline, physiological saline, water and emulsions, such as oil/water emulsions.

This invention provides a transgenic nonhuman mammal expressing DNA encoding a human Y5 receptor.

This invention provides a transgenic nonhuman mammal comprising a homologous recombination knockout of the native Y5 receptor.

This invention provides a transgenic nonhuman mammal whose genome comprises antisense DNA complementary to DNA encoding a human Y5 receptor so placed as to be transcribed into antisense mRNA which is complementary to mRNA encoding a Y5 receptor and which hybridizes to mRNA encoding a Y5 receptor thereby reducing its translation.

This invention provides the above-described transgenic nonhuman mammal, wherein the DNA encoding a human Y5 receptor additionally comprises an inducible promoter.

This invention provides the transgenic nonhuman mammal, wherein the DNA encoding a human Y5 receptor additionally comprises tissue specific regulatory elements.

In an embodiment, the transgenic nonhuman mammal is a mouse.

Animal model systems which elucidate the physiological and behavioral roles of Y5 receptor are produced by creating transgenic animals in which the activity of the Y5 receptor is either increased or decreased, or the amino acid sequence of the expressed Y5 receptor is altered, by a variety of techniques. Examples of these techniques include, but are not limited to: 1) Insertion of normal or mutant versions of DNA encoding a Y5 receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these Y5 receptor sequences. The technique of homologous recombination is well known in the art. It replaces the native gene with the inserted gene and so is useful for producing an animal that cannot express native Y5 receptors but does express, for example, an inserted mutant Y5 receptor, which has replaced the native Y5 receptor in the animal's genome by recombination, resulting in underexpression of the transporter. Microinjection adds genes to the genome, but does not remove them, and so is useful for producing an animal which expresses its own and added Y5 receptors, resulting in overexpression of the Y5 receptors.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a Y5 receptor is purified from a vector by methods well known in the art. Inducible promoters may be fused with the coding region of the DNA to provide an experimental means to regulate expression of the transgene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

This invention also provides a method for determining whether a ligand can specifically bind to a Y5 receptor which comprises contacting a cell transfected with and expressing DNA encoding the Y5 receptor with the ligand under conditions permitting binding of ligands to such receptor, detecting the presence of any such ligand specifically bound to the Y5 receptor, and thereby determining whether the ligand specifically binds to the Y5 receptor.

This invention provides a method for determining whether a ligand can specifically bind to a human Y5 receptor which comprises contacting a cell transfected with and expressing DNA encoding the human Y5 receptor with the ligand under conditions permitting binding of ligands to such receptor, detecting the presence of any such ligand specifically bound to the human Y5 receptor, and thereby determining whether the ligand specifically binds to the human Y5 receptor.

This invention provides a method for determining whether a ligand can specifically bind to a human Y5 receptor which comprises contacting a cell transfected with and expressing DNA encoding the human Y5 receptor with the ligand under conditions permitting binding of ligands to such receptor, detecting the presence of any such ligand specifically bound to the human Y5 receptor, and thereby determining whether the ligand specifically binds to the human Y5 receptor, such human Y5 receptor having substantially the same amino acid sequence shown in FIG. 6.

This invention provides a method for determining whether a ligand can specifically bind to a Y5 receptor which comprises contacting a cell transfected with and expressing DNA encoding the Y5 receptor with the ligand under conditions permitting binding of ligands to such receptor, detecting the presence of any such ligand specifically bound to the Y5 receptor, and thereby determining whether the ligand specifically binds to the Y5 receptor, such Y5 receptor being characterized by an amino acid sequence in the transmembrane region having 60% homology or higher to the amino acid sequence in the transmembrane region of the Y5 receptor shown in FIG. 6.

This invention provides a method for determining whether a ligand can specifically bind to a Y5 receptor which comprises preparing a cell extract from cells transfected with and expressing DNA encoding the Y5 receptor, isolating a membrane fraction from the cell extract, contacting the membrane fraction with the ligand under conditions permitting binding of ligands to such receptor, detecting the presence of the ligand specifically bound to the Y5 receptor, and thereby determining whether the ligand specifically binds to the Y5 receptor.

This invention provides a method for determining whether a ligand can specifically bind to a human Y5 receptor which comprises preparing a cell extract from cells transfected with and expressing DNA encoding the human Y5 receptor, isolating a membrane fraction from the cell extract, contacting the membrane fraction with the ligand under conditions permitting binding of ligands to the human Y5 receptor, detecting the presence of the ligand specifically bound to the human Y5 receptor, and thereby determining whether the ligand can specifically bind to the human Y5 receptor.

This invention provides a method for determining whether a ligand can specifically bind to a human Y5 receptor which comprises preparing a cell extract from cells transfected with and expressing DNA encoding the human Y5 receptor, isolating a membrane fraction from the cell extract, contacting the membrane fraction with the ligand under conditions permitting binding of ligands to the human Y5 receptor, detecting the presence of the ligand specifically bound to the human Y5 receptor, and thereby determining whether the ligand can specifically bind to the human Y5 receptor, such human Y5 receptor having substantially the same amino acid sequence shown in FIG. 6.

This invention provides a method for determining whether a ligand can specifically bind to a Y5 receptor which comprises preparing a cell extract from cells transfected with and expressing DNA encoding the Y5 receptor, isolating a membrane fraction from the cell extract, contacting the membrane fraction with the ligand under conditions permitting binding of ligands to the Y5 receptor, detecting the presence of the ligand specifically bound to the Y5 receptor, and thereby determining whether the ligand can specifically bind to the Y5 receptor, such Y5 receptor being characterized by an amino acid sequence in the transmembrane region having 60% homology or higher to the amino acid sequence in the transmembrane region of the Y5 receptor shown in FIG. 6.

In one embodiment, the Y5 receptor is a human Y5 receptor. In another embodiment, the Y5 receptor is a rat Y5 receptor. In another embodiment, the Y5 receptor is a canine Y5 receptor.

This invention provides a method for determining whether a ligand is a Y5 receptor agonist which comprises contacting a cell transfected with and expressing a Y5 receptor with the ligand under conditions permitting activation of a functional Y5 receptor response, detecting a functional increase in Y5 receptor activity, and thereby determining whether the ligand is a Y5 receptor agonist.

This invention provides a method for determining whether a ligand is a Y5 receptor agonist which comprises contacting a cell transfected with and expressing a Y5 receptor with the ligand under conditions permitting activation of the Y5 receptor, detecting an increase in Y5 receptor activity, and thereby determining whether the ligand is a Y5 receptor agonist.

This invention provides a method for determining whether a ligand is a Y5 receptor agonist which comprises preparing a cell extract from cells transfected with and expresssing DNA encoding the Y5 receptor, isolating a membrane fraction from the cell extract, contacting the membrane fraction with the ligand under conditions permitting activation of a Y5 receptor, and detecting an increase in Y5 receptor activity, so as to thereby determine whether the ligand is a Y5 receptor agonist.

In one embodiment of the above-described methods, the Y5 receptor is a human Y5 receptor. In another embodiment, the Y5 receptor is a rat Y5 receptor. In a further embodiment, the Y5 receptor is a canine Y5 receptor.

This invention provides a method for determining whether a ligand is a Y5 receptor antagonist which comprises contacting a cell transfected with and expressing DNA encoding a Y5 receptor with the ligand in the presence of a known Y5 receptor agonist, such as PYY or NPY, under conditions permitting the activation of a functional Y5 receptor response, detecting a decrease in Y5 receptor activity, and thereby determining whether the ligand is a Y5 receptor antagonist.

This invention provides a method for determining whether a ligand is a Y5 receptor antagonist which comprises contacting a cell transfected with and expressing DNA encoding a Y5 receptor with the ligand in the presence of a known Y5 receptor agonist, such as PYY or NPY, under conditions permitting the activation of the Y5 receptor, detecting a decrease in Y5 receptor activity, and thereby determining whether the ligand is a Y5 receptor antagonist.

This invention provides a method for determining whether a ligand is a Y5 receptor antagonist which comprises preparing a cell extract from cells transfected with and expressing DNA ecoding a Y5 receptor, isolating a membrane fraction from the cell extract, contacting the membrane fraction with the ligand in the presence of a known Y5 receptor agonist, such as PYY or NPY, under conditions permitting the activation of the Y5 receptor, detecting a decrease in Y5 receptor activity, and thereby determining whether the ligand is a Y5 receptor antagonist.

In one embodiment of the above-described methods, the Y5 receptor is a human Y5 receptor. In another embodiment, the Y5 receptor is a rat Y5 receptor. In a further embodiment, the Y5 receptor is a canine Y5 receptor.

In an embodiment of the above-described methods, the cell is non-neuronal in origin. In a further embodiment, the non-neuronal cell is a COS-7 cell, 293 human embryonic kidney cell, NIH-3T3 cell or LM(tk–) cell.

In one embodiment of the above-described methods, the ligand is not previously known.

This invention provides a Y5 receptor agonist detected by the above-described method. This invention provides a Y5 receptor antagonist detected by the above-described method.

This invention provides a method of screening a plurality of chemical compounds not known to bind to a Y5 receptor to identify a compound which specifically binds to the Y5 receptor which comprises (a) contacting a cell transfected with and expressing DNA encoding the Y5 receptor with a compound known to bind specifically to the Y5 receptor; (b) contacting the preparation of step (a) with the plurality of compounds not known to bind specifically to the Y5 receptor, under conditions permitting binding of compounds known to bind to the Y5 receptor; (c) determining whether the binding of the compound known to bind to the Y5 receptor is reduced in the presence of the compounds, relative to the binding of the compound in the absence of the plurality of compounds; and if so (d) separately determining the binding to the Y5 receptor of each compound included in the plurality of compounds, so as to thereby identify the compound which specifically binds to the Y5 receptor.

This invention provides a method of screening a plurality of compounds not known to bind to a Y5 receptor to identify a compound which specifically binds to the Y5 receptor, which comprises (a) preparing a cell extract from cells transfected with and expressing DNA ecoding the Y5 receptor, isolating a membrane fraction from the cell extract, contacting the membrane fraction with a compound known to bind specifically to the Y5 receptor; (b) contacting the preparation of step (a) with the plurality of compounds not known to bind specifically to the Y5 receptor, under conditions permitting binding of compounds known to bind the Y5 receptor; (c) determining whether the binding of the compound known to bind to the Y5 receptor is reduced in the presence of the compounds, relative to the binding of the compound in the absence of the plurality of compounds; and if so (d) separately determining the binding to the Y5 receptor of each compound included in the plurality of compounds, so as to thereby identify the compound which specifically binds to the Y5 receptor.

This invention provides a method of screening a plurality of chemical compounds not known to activate a Y5 receptor to identify a compound which activates the Y5 receptor which comprises (a) contacting a cell transfected with and expressing the Y5 receptor with the plurality of compounds not known to bind specifically to the Y5 receptor, under conditions permitting activation of the Y5 receptor; (b) determining whether the activity of the Y5 receptor is increased in the presence of the compounds; and if so (c) separately determining whether the activation of the Y5 receptor is increased by each compound included in the plurality of compounds, so as to thereby identify the compound which activates the Y5 receptor.

This invention provides a method of screening a plurality of chemical compounds not known to activate a Y5 receptor to identify a compound which activates the Y5 receptor which comprises (a) preparing a cell extract from cells transfected with and expressing DNA encoding the Y5 receptor, isolating a membrane fraction from the cell extract, contacting the membrane fraction with the plurality of compounds not known to bind specifically to the Y5 receptor, under conditions permitting activation of the Y5 receptor; (b) determining whether the activity of the Y5 receptor is increased in the presence of the compounds; and if so (c) separately determining whether the activation of the Y5 receptor is increased by each compound included in the plurality of compounds, so as to thereby identify the compound which activates the Y5 receptor.

This invention provides a method of screening a plurality of chemical compounds not known to inhibit the activation of a Y5 receptor to identify a compound which inhibits the activation of the Y5 receptor, which comprises (a) contacting a cell transfected with and expressing the Y5 receptor with the plurality of compounds in the presence of a known Y5 receptor agonist, under conditions permitting activation of the Y5 receptor; (b) determining whether the activation of the Y5 receptor is reduced in the presence of the plurality of compounds, relative to the activation of the Y5 receptor in the absence of the plurality of compounds; and if so (c) separately determining the inhibition of activation of the Y5 receptor for each compound included in the plurality of compounds, so as to thereby identify the compound which inhibits the activation of the Y5 receptor.

A method of screening a plurality of chemical compounds not known to inhibit the activation of a Y5 receptor to identify a compound which inhibits the activation of the Y5 receptor, which comprises (a) preparing a cell extract from cells transfected with and expressing DNA encoding the Y5 receptor, isolating a membrane fraction from the cell extract, contacting the membrane fraction with the plurality of compounds in the presence of a known Y5 receptor agonist, under conditions permitting activation of the Y5 receptor; (c) separately determining the inhibition of activation of the Y5 receptor for each compound included in the plurality of compounds, so as to thereby identify the compound which inhibits the activation of the Y5 receptor.

In one embodiment of the above-described methods the Y5 receptor is a human Y5 receptor. In another embodiment, the Y5 receptor is a rat Y5 receptor. In a further embodiment, the Y5 receptor is a canine Y5 receptor. In another embodiment, the cell is a mammalian cell. In a further embodiment, the mammalian cell is non-neuronal in origin. The cell may be a COS-7 cell, a 293 human embryonic kidney cell, a LM(tk-) cell, or an NIH-3T3 cell.

This invention provides a method of screening-drugs to identify drugs which specifically bind to a Y5 receptor on the surface of a cell which comprises contacting a cell transfected with and expressing DNA encoding a Y5 receptor with a plurality of drugs under conditions permitting binding of drugs to the Y5 receptor, determining those drugs which specifically bind to the transfected cell, and thereby identifying drugs which specifically bind to the Y5 receptor.

This invention provides a method of screening drugs to identify drugs which act as agonists of a Y5 receptor which comprises contacting a cell transfected with and expressing DNA encoding a Y5 receptor with a plurality of drugs under conditions permitting the activation of a functional Y5 receptor response, determining those drugs which activate such receptor in the cell, and thereby identify drugs which act as Y5 receptor agonists.

This invention provides a method of screening drugs to identify drugs which act as agonists of a human Y5 receptor which comprises contacting a cell transfected with and expressing DNA encoding a human Y5 receptor with a plurality of drugs under conditions permitting the activation of a functional human Y5 receptor response, determining those drugs which activate such receptor in the cell, and thereby identify drugs which act as human Y5 receptor agonists.

This invention provides a method of screening drugs to identify drugs which act as Y5 receptor antagonists which comprises contacting cells transfected with and expressing DNA encoding a Y5 receptor with a plurality of drugs in the presence of a known Y5 receptor agonist, such as PYY or NPY, under conditions permitting the activation of a functional Y5 receptor response, determining those drugs which inhibit the activation of the receptor in the mammalian cell, and thereby identifying drugs which act as Y5 receptor antagonists.

This invention provides a method of screening drugs to identify drugs which act as human Y5 receptor antagonists which comprises contacting cells transfected with and expressing DNA encoding a human Y5 receptor with a plurality of drugs in the presence of a known human Y5 receptor agonist, such as PYY or NPY, under conditions permitting the activation of a functional human Y5 receptor response, determining those drugs which inhibit the activation of the receptor in the mammalian cell, and thereby identifying drugs which act as human Y5 receptor antagonists. In an embodiment, the cell is non-neuronal in origin. In a further embodiment, the cell is a Cos-7 cell, a 293 human embryonic kidney cell, an LM(tk-) cell or an NIH-3T3 cell.

This invention provides a pharmaceutical composition comprising a drug identified by the above-described methods and a pharmaceutically acceptable carrier.

This invention provides a method of detecting expression of Y5 receptor by detecting the presence of mRNA coding for the Y5 receptor which comprises obtaining total mRNA from the cell and contacting the mRNA so obtained with the above-described nucleic acid probe under hybridizing conditions, detecting the presence of mRNA hybridized to the probe, and thereby detecting the expression of the Y5 receptor by the cell.

This invention provides a method of treating an abnormality in a subject, wherein the abnormality is alleviated by the inhibition of a Y5 receptor which comprises administering to a subject an effective amount of the above-described pharmaceutical composition effective to inhibit the Y5 receptor by the subject.

This invention provides a method of treating an abnormality in a subject wherein the abnormality is alleviated by the activation of a Y5 receptor which comprises administering to a subject an effective amount of the above-described pharmaceutical composition effective to activate the Y5 receptor in the subject.

This invention provides a method of treating an abnormality in a subject, wherein the abnormality is alleviated by the inhibition of a Y5 receptor which comprises administering to a subject an effective amount of Y5 receptor antagonist.

In one embodiment of the above-described methods, the abnormality is obesity. In another embodiment, the abnormality is bulimia.

This invention provides a method of treating an abnormality in a subject wherein the abnormality is alleviated by the activation of a Y5 receptor which comprises administering to a subject an effective amount of a Y5 receptor agonist. In a further embodiment, the abnormal condition is anorexia. In a separate embodiment, the abnormal condition is a sexual/reproductive disorder. In another embodiment, the abnormal condition is depression. In another embodiment, the abnormal condition is anxiety.

In an embodiment, the abnormal condition is gastric ulcer. In a further embodiment, the abnormal condition is memory loss. In a further embodiment, the abnormal condition is migraine. In a further embodiment, the abnormal condition is pain. In a further embodiment, the abnormal condition is epileptic seizure. In a further embodiment, the abnormal condition is hypertension. In a further embodiment, the abnormal condition is cerebral hemorrhage. In a further embodiment, the abnormal condition is shock. In a further embodiment, the abnormal condition is congestive heart failure. In a further embodiment, the abnormal condition is sleep disturbance. In a further embodiment, the abnormal condition is nasal congestion. In a further embodiment, the abnormal condition is diarrhea.

This invention provides a method of treating obesity in a subject which comprises administering to the subject an effective amount of a Y5 receptor antagonist.

This invention provides a method of treating anorexia in a subject which comprises administering to the subject an effective amount of a Y5 receptor agonist.

This invention provides a method of treating bulimia nervosa in a subject which comprises administering to the subject an effective amount of a Y5 receptor antagonist.

This invention provides a method of inducing a subject to eat which comprises administering to the subject an effective amount of a Y5 receptor agonist. In one embodiment, the subject is a vertebrate. In another embodiment, the subject is a human. In another embodiment, the subject is a rat. In another embodiment, the subject is a canine subject.

This invention provides a method of increasing the consumption of a food product by a subject which comprises a composition of the food product and an effective amount of a Y5 receptor agonist. In one embodiment, the subject is a vertebrate. In another embodiment, the subject is a human, a rat or a canine subject.

This invention provides a method of treating abnormalities which are alleviated by reduction of activity of a human Y5 receptor which comprises administering to a subject an amount of the above-described pharmaceutical composition effective to reduce the activity of human Y5 receptor and thereby alleviate abnormalities resulting from overactivity of a human Y5 receptor.

This invention provides a method of treating an abnormal condition related to an excess of Y5 receptor activity which comprises administering to a subject an amount of the pharmaceutical composition effective to block binding of a ligand to the Y5 receptor and thereby alleviate the abnormal condition.

This invention provides a method of detecting the presence of a human Y5 receptor on the surface of a cell which comprises contacting the cell with the antibody capable of binding to the human Y5 receptor under conditions permitting binding of the antibody to the receptor, detecting the presence of the antibody bound to the cell, and thereby detecting the presence of a human Y5 receptor on the surface of the cell.

This invention provides a method of determining the physiological effects of varying levels of activity of a human Y5 receptors which comprises producing a transgenic nonhuman mammal whose levels of human Y5 receptor activity are varied by use of an inducible promoter which regulates human Y5 receptor expression.

This invention provides a method of determining the physiological effects of varying levels of activity of a human Y5 receptors which comprises producing a panel of transgenic nonhuman mammals each expressing a different amount of human Y5 receptor.

This invention provides a method for identifying a substance capable of alleviating the abnormalities resulting from overactivity of a human Y5 receptor comprising administering a substance to the above-described transgenic nonhuman mammals, and determining whether the substance alleviates the physical and behavioral abnormalities displayed by the transgenic nonhuman mammal as a result of overactivity of a human Y5 receptor.

This invention provides a method for treating the abnormalities resulting from overactivity of a human Y5 receptor which comprises administering to a subject an amount of the above-described pharmaceutical composition effective to alleviate the abnormalities resulting from overactivity of a human Y5 receptor.

This invention provides a method for identifying a substance capable of alleviating the abnormalities resulting from underactivity of a human Y5 receptor comprising administering the substance to the above-described transgenic nonhuman mammals and determining whether the substance alleviates the physical and behavioral abnormalities displayed by the transgenic nonhuman mammal as a result of underactivity of a human Y5 receptor.

This invention provides a method for treating the abnormalities resulting from underactivity of a human Y5 receptor which comprises administering to a subject an amount of the above-described pharmaceutical composition effective to alleviate the abnormalities resulting from underactivity of a human Y5 receptor.

This invention provides a method for diagnosing a predisposition to a disorder associated with the activity of a specific human Y5 receptor allele which comprises: a. obtaining DNA of subjects suffering from the disorder; performing a restriction digest of the DNA with a panel of restriction enzymes; c. electrophoretic-ally separating the resulting DNA fragments on a sizing gel; d. contacting the resulting gel with a nucleic acid probe capable of specifically hybridizing to DNA encoding a human Y5 receptor and labelled with a detectable marker; e. detecting labelled bands which have hybridized to the DNA encoding a human Y5 receptor labelled with a detectable marker to create a unique band pattern specific to the DNA of subjects suffering from the disorder; f. preparing DNA obtained for diagnosis by steps a–e; and g. comparing the unique band pattern specific to the DNA of subjects suffering from the disorder from step e and the DNA obtained for diagnosis from step f to determine whether the patterns are the same or different and to diagnose thereby predisposition to the disorder if the patterns are the same. In an embodiment, a disorder associated with the activity of a specific human Y5 receptor allele is diagnosed.

This invention provides a method of preparing an isolated Y5 receptor which comprises: a. inducing cells to express the Y5 receptor; b. recovering the receptor from the resulting cells; and c. purifying the receptor so recovered.

This invention provides a method of preparing the isolated Y5 receptor which comprises: a. inserting nucleic acid encoding Y5 receptor in a suitable vector adapted for expression in a bacterial, yeast insect or mammalian cell operatively linked to the nucleic acid encoding the Y5 receptor as to permit expression thereof; b. inserting the resulting vector in a suitable host cell so as to obtain a cell which produces the Y5 receptor; c. recovering the receptor produced by the resulting cell; and d. purifying the receptor so recovered.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

MATERIALS AND METHODS cDNA Cloning

Total RNA was prepared by a modification of the guanidine thiocyanate method (Kingston, 1987), from 5 grams of rat hypothalamus (Rockland, Gilbertsville, Pa.). Poly $A^+$RNA was purified with a FastTrack kit (Invitrogen Corp., San Diego, Calif.). Double stranded (ds) cDNA was synthesized from 7 μg of poly $A^+$ RNA according to Gubler and Hoffman (Gubler and Hoffman, 1983), except that ligase was omitted in the second strand cDNA synthesis. The resulting DS cDNA was ligated to BstxI/EcoRI adaptors (Invitrogen Corp.), the excess of adaptors was removed by chromatography on Sephacryl 500 HR (Pharmacia®-LKB) and the ds-cDNA size selected on a Gen-Pak Fax HPLC column (Millipore Corp., Milford, Mass.). High molecular weight fractions were ligated in pEXJ.BS (A cDNA cloning expression vector derived from pcEXV-3; Okayama and Berg, 1983; Miller and Germain, 1986) cut by BstxI as described by Aruffo and Seed (Aruffo and Seed, 1987). The ligated DNA was electroporated in $E.\ coli$ MC 1061 F$^+$ (Gene Pulser, Biorad). A total of $3.4 \times 10^6$ independent clones with an insert mean size of 2.7 kb could be generated. The library was plated on Petri dishes (Ampicillin selection) in pools of 6.9 to $8.2 \times 10^3$ independent clones. After 18 hours amplification, the bacteria from each pool were scraped, resuspended in 4 mL of LB media and 1.5 mL processed for plasmid purification with a QIAprep-8 plasmid kit (Qiagen Inc, Chatsworth, Calif.). 1 ml aliquots of each bacterial pool were stored at $-85°$ C. in 20% glycerol.

Isolation of a cDNA clone encoding an atypical rat hypothalamic NPY5 receptor

DNA from pools of ≈7500 independent clones was transfected into COS-7 cells by a modification of the DEAE-dextran procedure (Warden and Thorne, 1968). COS-7 cells were grown in Dulbecco's modified Eagle medium (DMEM) supplemented with 10% fetal calf serum, 100 U/ml of penicillin, 100 $\mu$g/ml of streptomycin, 2 mM L-glutamine (DMEM-C) at 37° C. in 5% $CO_2$. The cells were seeded one day before transfection at a density of 30,000 cells/cm$^2$ on Lab-Tek chamber slides (1 chamber, Permanox slide from Nunc Inc., Naperville, Ill.). On the next day, cells were washed twice with PBS, 735 $\mu$l of transfection cocktail was added containing 1/10 of the DNA from each pool and DEAE-dextran (500 $\mu$g/ml) in Opti-MEM I serum free media (Gibco BRL LifeTechnologies Inc. Grand Island, N.Y.). After a 30 min. incubation at 37° C., 3 ml of chloroquine (80 $\mu$M in DMEM-C) was added and the cells incubated a further 2.5 hours at 37° C. The media was aspirated from each chamber and 2 ml of 10% DMSO in DMEM-C added. After 2.5 minutes incubation at room temperature, the media was aspirated, each chamber washed once with 2 ml PBS, the cells incubated 48 hours in DMEM-C and the binding assay was performed on the slides. After one wash with PBS, positive pools were identified by incubating the cells with 1 nM ($3 \times 10^6$ cpm per slide) of porcine [$^{125}$I]-PYY (NEN; SA=2200Ci/mmole) in 20 mM Hepes-NaOH pH 7.4, CaCl2 1.26 mM, MgSO4 0.81 mM, $KH_2PO_4$ 0.44 mM, KCL 5.4, NaCl 10 mM, 0.1% BSA, 0.1 bacitracin for 1 hour at room temperature. After six washes (three seconds each) in binding buffer without ligand, the monolayers were fixed in 2.5% glutaraldehyde in PBS for five minutes, washed twice for two minutes in PBS, dehydrated in ethanol baths for two minutes each (70, 80, 95, 100%) and air dried. The slides were then dipped in 100% photoemulsion (Kodak type NTB2) at 42° C. and exposed in the dark for 48 hours at 4° C. in light proof boxes containing drierite. Slides were developed for three minutes in Kodak D19 developer (32 g/l of water), rinsed in water, fixed in Kodak fixer for 5 minutes, rinsed in water, air dried and mounted with Aqua-Mount (Lerner Laboratories, Pittsburgh, Pa.). Slides were screened at 25x total magnification. A single clone, CG-18, was isolated by SIB selection as described (Mc Cormick, 1987). DS-DNA was sequenced with a Sequenase kit (US Biochemical, Cleveland, Ohio) according to the manufacturer. Nucleotide and peptide sequence analysis were performed with GCG programs (Genetics Computer group, Madison, Wis.).

Isolation of the human Y5 homolog

Using rat oligonucleotide primers in TM 3 (sense primer; position 484–509 in FIG. 1A) and in TM 6 (antisense primer; position 1219–1243 in FIG. 3A), applicants screened a human hippocampal cDNA library using the polymerase chain reaction. 1 $\mu$l ($4 \times 10^6$ bacteria) of each of 450 amplified pools containing each ≈5000 independent clones and representing a total of $2.2 \times 10^6$ was subjected directly to 40 cycles of PCR and the resulting products analyzed by agarose gel electrophoresis. One of three positive pools was analyzed further and by sib selection a single cDNA clone was isolated and characterized. This cDNA turned out to be full length and in the correct orientation for expression. DS-DNA was sequenced with a sequenase kit (US Biochemical, Cleveland, Ohio) according to the manufacturer.

Isolation of the canine Y5 homolog

An alignment of the coding nucleotide sequences of the rat and human Y5 receptors was used to synthesize a pair of PCR primers. A region upstream of TM III which is 100% conserved between rat and human was chosen to synthesize the forward primer CH 156:

5'-TGGATCAGTGGATGTTTGGCAAAG-3' (Seq. I.D. No. 7).

A region at the carboxy end of the 5–6 loop, immediately upstream of TM6, which is also 100% conserved between rat and human sequences was chosen to synthesize the reverse primer CH153:

5'-GTCTGTAGAAAACACTTCGAGATCTCTT-3'(Seq. I.D. No. 8).

The primers CH156-CH153 were used to amplify 10 ng of poly (A+) RNA from rat brain that was reverse transcribed using the SSII reverse transcriptase (GibcoBRL, Gaithersburg, Md.). PCR was performed on single-stranded cDNA with Taq Polymerase (Perkin Elmer-Roche Molecular Systems, Branchburg, N.J.)under the following conditions: 94° C. for 1 min, 60° C. for 1 min and 72° C. for 1 min for 40 cycles. The resulting 798 bp PCR DNA fragment was subcloned in pCR Script (Stratagene, La Jolla, Calif.) and sequenced using a sequenase kit (USB, Cleveland, Ohio) and is designated Y5-bd-5.

3' and 5' RACE

The missing 3' and 5' ends of the beagle dog Y5 receptor sequences were isolated by 3' and 5' RACE using a Marathon cDNA amplification kit (Clontech, Palo Alto, Calif.). From the sequence of the beagle dog PCR DNA fragment described above, the following PCR primers were synthesized:

(3' RACE)
CH 204:

5'-CTTCCAGTGTTTCACAGTCTGGTGG-3' (Seq. I.D. No. 9);

CH 218 (nested primer):

5'-CTGAGCAGCAGGTATTTATGTGTTG-3' (Seq. I.D. No. 10);

(5' RACE)
CH 219:

5'-CTGGATGAAGAATGCTGACTTCTTACAG-(Seq. I.D. No. 11):

CH 245 (nested primer):

5'-TTCTTGAGTGGTTCTCTTGAGGAGG-3' (Seq. I.D. No. 12).

The 3' and 5' RACE reactions were carried out on beagle dog thalamic cDNA according to the kit specifications, with the primers described above. The resulting PCR DNA products (smear of 0.7 to 10 kb) were purified from an agarose gel and reamplified using the nested primers described above. The resulting discrete DNA bands were again purified from an agarose gel and subcloned in pCR Script (Stratagene, La Jolla, Calif.).

The nucleotide sequence corresponding to the 3' end of the cDNA was determined and the plasmid designated Y5-bd-8. The nucleotide sequence corresponding to the 5' end will be determined in the near future. Those nucleotide sequences will then be used to synthesize exact primers against the initiation and stop codon regions and those exact primers will then be used to amplify canine thalamic cDNA to generate a PCR product corresponding to the full length coding region of the canine Y5 receptor, using the Expand High Fidelity polymerase (Boehringer Mannheim Corporation, Indianapolis, Ind.). The resulting PCR DNA product will be subcloned in the expression vector pEXJ and the entire coding region of the canine Y5 nucleotide sequence will be determined using a Sequenase Kit (USB, Cleveland, Ohio).

Northern Blots

Human brain multiple tissue northern blots (MTN blots II and III, Clontech, Palo Alto, Calif.) carrying mRNA purified from various human brain areas was hybridized at high stringency according to the manufacturer specifications. The probe was a 0.8 kb DNA PCR fragment corresponding to the TM III - carboxy end of the 5–6 loop in the coding region of the human Y5 receptor subtype.

A rat multiple tissue northern blot (rat MTN blot, Clontech, Palo Alto, Calif.) carrying mRNA purified from various rat tissues was hybridized at high stringency according to the manufacturer specifications. The probe was a 0.8 kb DNA PCR fragment corresponding to the TM III - carboxy end of the 5–6 loop in the coding region of the rat Y5 receptor subtype.

Southern Blot

Southern blots (Geno-Blot, clontech, Palo Alto, Calif.) containing human or rat genomic DNA cut with five different enzymes (8 µg DNA per lane) was hybridized at high stringency according to the manufacturer specifications. The probe was a 0.8 kb DNA PCR fragment corresponding to the TM III - carboxy end of the 5–6 loop in the coding region of the human and rat Y5 receptor subtypes.

Production of Recombinant Baculovirus

A BamHI site directly 5' to the starting methionine of human Y5 was genetically engineered by replacing the beginning ≈100 base pairs of hY5 (i.e. from the starting methionine to an internal EcoRI site) with two overlapping synthetically-derived oligonucleotides (≈100 bases each), containing a 5' BamHI site and a 3' EcoRI site. This permitted the isolation of an ≈1.5 kb Bam HI/Hind III fragment containing the coding region of hY5. This fragment was subcloned into pBlueBacIII™ into the Bam HI/Hind III sites found in the polylinker (construct called pBB/hY5). To generate baculovirus, 0.5 µg of viral DNA (BaculoGold™) and 3 µg of pBB/hY5 were co-transfected into 2×10$^6$ Spodoptera frugiperda insect Sf9 cells by calcium phosphate co-precipitation method, as outlined in by Pharmingen (in "Baculovirus Expression Vector System: Procedures and Methods Manual"). The cells were incubated for 5 days at 27° C. The supernatant of the co-transfection plate was collected by centrifugation and the recombinant virus (hYSBB3) was plaque purified. The procedure to infect cells with virus, to prepare stocks of virus and to titer the virus stocks were as described in Pharmingen's manual.

Cell Culture

COS-7 cells were grown on 150 mm plates in D-MEM with supplements (Dulbecco's Modified Eagle Medium with 10% bovine calf serum, 4 mM glutamine, 100 units/ml penicillin/100 µg/ml streptomycin) at 37° C., 5% $CO_2$. Stock plates of COS-7 cells were trypsinized and split 1:6 every 3–4 days. Human embryonic kidney 293 cells were grown on 150 mm plates in D-MEM with supplements (minimal essential medium) with Hanks' salts and supplements (Dulbecco's Modified Eagle Medium with 10% bovine calf serum, 4 mM glutamine, 100 units/ml penicillin/100 µg/ml streptomycin) at 37° C., 5% $CO_2$. Stock plates of 293 cells were trypsinized and split 1:6 every 3–4 days. Mouse fibroblast LM(tk–) cells were grown on 150 mm plates in D-MEM with supplements (Dulbecco's Modified Eagle Medium with 10% bovine calf serum, 4 mM glutamine, 100 units/mL penicillin/100 µg/mL streptomycin) at 37° C., 5% $CO_2$. Stock plates of LM(tk–) cells were trypsinized and split 1:10 every 3–4 days.

LM(tk–) cells stably transfected with the human Y5 receptor were routinely converted from an adherent monolayer to a viable suspension. Adherent cells were harvested with trypsin at the point of confluence, resuspended in a minimal volume of complete DMEM for a cell count, and further diluted to a concentration of 10$^6$ cells/ml in suspension media (10% bovine calf serum, 10% 10× Medium 199 (Gibco), 9 mM $NaHCO_3$, 25 mM glucose, 2 mM L-glutamine, 100 units/ml penicillin/100 µg/ml streptomycin, and 0.05% methyl cellulose). The cell suspension was maintained in a shaking incubator at 37° C., 5% $CO_2$ for 24 hours. Membranes harvested from cells grown in this manner may be stored as large, uniform batches in liquid nitrogen. Alternatively, cells may be returned to adherent cell culture in complete DMEM by distribution into 96-well microtiter plates coated with poly-D-lysine (0.01 mg/ml) followed by incubation at 37° C., 5% $CO_2$ for 24 hours. Cells prepared in this manner yielded a robust and reliable NPY-dependent response in cAMP radio-immunoassays as further described hereinbelow.

Mouse embryonic fibroblast NIH-3T3 cells were grown on 150 mm plates in Dulbecco's Modified Eagle Medium (DMEM) with supplements (10% bovine calf serum, 4 mM glutamine, 100 units/ml penicillin/100 µg/ml streptomycin) at 37° C., 5% CO2. Stock plates of NIH-3T3 cells were trypsinized and split 1:15 every 3–4 days.

Sf9 and Sf21 cells were grown in monolayers on 150 mm tissue culture dishes in TMN-FH media supplemented with 10% fetal calf serum, at 27° C., no $CO_2$. High Five insect cells were grown on 150 mm tissue culture dishes in ExCell 400™ medium supplemented with L-Glutamine, also at 27° C., no $CO_2$.

Transient Transfection

All receptor subtypes studied (human and rat Y1, human and rat Y2, human and rat Y4, human and rat Y5) were transiently transfected into COS-7 cells by the DEAE-dextran method, using 1 µg of DNA /10$^6$ cells (Cullen, 1987). The Y1 receptor was prepared using to known methods (Larhammar, et al., 1992).

Stable Transfection

Human Y1, human Y2, and rat Y5 receptors were co-transfected with a G-418 resistant gene into the human embryonic kidney 293 cell line by a calcium phosphate transfection method (Cullen, 1987). Stably transfected cells were selected with G-418. Human Y4 and human Y5 receptors were similarly transfected into mouse fibroblast LM(tk–) cells and NIH-3T3 cells.

Expression of other G-protein coupled receptors $\alpha_1$ Human Adrenergic Receptors: To determine the binding of compounds to human $\alpha_1$ receptors, LM(tk−) cell lines stably transfected with the genes encoding the $\alpha_{1a}$, $\alpha_{1b}$, and $\alpha_{1d}$ receptors were used. The nomenclature describing the $\alpha_1$ receptors was changed recently, such that the receptor formerly designated $\alpha_{1a}$ is now designated $\alpha_{1d}$, and the receptor formerly designated $\alpha_{1c}$ is now designated $\alpha_{1a}$ (ref). The cell lines expressing these receptors were deposited with the ATCC before the nomenclature change and reflect the subtype designations formerly assigned to these receptors. Thus, the cell line expressing the receptor described herein as the $\alpha_{1a}$ receptor was deposited with the ATCC on Sep. 25, 1992, under ATCC Accession No. CRL 11140 with the designation L-$\alpha_{1c}$. The cell line expressing receptor described herein as the $\alpha_{1d}$ receptor was deposited with the ATCC on Sep. 25, 1992, under ATCC Accession No. CRL 11138 with the designation L-$\alpha_{1A}$. The cell line expressing the $\alpha_{1b}$ receptor is designated L-$\alpha_{1B}$, and was deposited on Sep. 25, 1992, under ATCC Accession No. CRL 11139.

$\alpha_2$ Human Adrenergic Receptors: To determine the binding of compounds to human $\alpha_2$ receptors, LM (tk−) cell lines stably transfected with the genes encoding the $\alpha_{2A}$, $\alpha_{2B}$, and $\alpha_{2C}$ receptors were used. The cell line expressing the $\alpha_{2A}$ receptor is designated L-$\alpha_{2A}$, and was deposited on Nov. 6, 1992, under ATCC Accession No. CRL 11180. The cell line expressing the $\alpha_{2B}$ receptor is designated L-NGC-$\alpha_{2B}$, and was deposited on Oct. 25, 1989, under ATCC Accession No. CRL 10275. The cell line expressing the $\alpha_{2C}$ receptor is designated L-$\alpha_{2C}$, and was deposited on Nov. 6, 1992, under ATCC Accession No. CRL-11181. Cell lysates were prepared as described below (see Radioligand Binding to Membrane Suspensions), and suspended in 25 mM glycylglycine buffer (pH 7.6 at room temperature). Equilibrium competition binding assay were performed using [$^3$H] rauwolscine (0.5 nM), and nonspecific binding was determined by incubation with 10 μM phentolamine. The bound radioligand was separated by filtration through GF/B filters using a cell harvester.

Human Histamine $H_1$ Receptor: The coding sequence of the human histamine $H_1$ receptor, homologous to the bovine $H_1$ receptor, was obtained from a human hippocampal cDNA library, and was cloned into the eukaryotic expression vector pcEXV-3. The plasmid DNA for the $H_1$ receptor is designated pcEXV-H1, and was deposited on Nov. 6, 1992, under ATCC Accession No. 75346. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 4° C., and the supernatant was centrifuged at 30,000× g for 20 min. at 4° C. The pellet was suspended in 37.8 mM NaHPO$_4$, 12.2 mM KH$_2$PO$_4$, pH 7.5. The binding of the histamine $H_1$ antagonist [$^3$H]mepyramine (1 nM, specific activity: 24.8 Ci/mM) was done in a final volume of 0.25 mL and incubated at room temperature for 60 min. Nonspecific binding was determined in the presence of 10 μM mepyramine. The bound radioligand was separated by filtration through GF/B filters using a cell harvester.

Human Histamine $H_2$ Receptor: The coding sequence of the human $H_2$ receptor was obtained from a human placenta genomic library, and cloned into the cloning site of PCEXV-3 eukaryotic expression vector. The plasmid DNA for the $H_2$ receptor is designated pcEXV-H2, and was deposited on Nov. 6, 1992 under ATCC Accession No. 75345. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 4° C., and the supernatant was centrifuged at 30,000× g for 20 min at 4° C. The pellet was suspended in 37.8 mM NaHPO$_4$, 12.2 mM K$_2$PO$_4$, pH 7.5. The binding of the histamine $H_2$ antagonist [$^3$H]tiotidine (5 nM, specific activity: 70 Ci/mM) was done in a final volume of 0.25 ml and incubated at room temperature for 60 min. Nonspecific binding was determined in the presence of 10 μM histamine. The bound radioligand was separated by filtration through GF/B filters using a cell harvester.

Human Serotonin Receptors:

$5HT_{1D\alpha}$, $5HT_{1D\beta}$, $5HT_{1E}$, $5HT_{1F}$ Receptors: LM(tk−) clonal cell lines stably transfected with the genes encoding each of these 5HT receptor subtypes were prepared as described above. The cell line for the $5HT_{1D\alpha}$ receptor, designated as Ltk-8-30-84, was deposited on Apr. 17, 1990, and accorded ATCC Accession No. CRL 10421. The cell for the $5HT_{1D\beta}$ receptor, designated as Ltk-11, was deposited on Apr. 17, 1990, and accorded ATCC Accession No. CRL 10422. The cell line for the $5HT_{1E}$ receptor, designated 5 HT$_{1E}$-7, was deposited on Nov. 6, 1991, and accorded ATCC Accession No. CRL 10913. The cell line for the $5HT_{1F}$ receptor, designated L-5-HT$_{1F}$, was deposited on Dec. 27, 1991, and accorded ATCC Accession No. ATCC 10957. Membrane preparations comprising these receptors were prepared as described below, and suspended in 50 mM Tris-HCl buffer (pH 7.4 at 37° C.) containing 10 mM MgCl$_2$, 0.2 mM EDTA, 10 μM pargyline, and 0.1% ascorbate. The binding of compounds was determined in competition binding assays by incubation for 30 minutes at 37° C. in the presence of 5 nM [$^3$H] serotonin. Nonspecific binding was determined in the presence of 10 μM serotonin. The bound radioligand was separated by filtration through GF/B filters using a cell harvester.

Human $5HT_2$ Receptor: The coding sequence of the human $5HT_2$ receptor was obtained from a human brain cortex cDNA library, and cloned into the cloning site of pcEXV-3 eukaryotic expression vector. This construct was transfected into COS-7 cells by the DEAE-dextran method. Cells were harvested after 72 hours and lysed by sonication in 5 mM Tris-HCl, 5 mM EDTA, pH 7.5. This cell line was deposited with the ATCC on Oct. 31, 1989, designated as L-NGC-5HT$_2$, and was accorded ATCC Accession No. CRL 10287. The cell lysates were centrifuged at 1000 rpm for 5 minutes at 4° C., and the supernatant was centrifuged at 30,000× g for 20 minutes at 4° C. The pellet was suspended in 50 mM Tris-HCl buffer (pH 7.7 at room temperature) containing 10 mM MgSO$_4$, 0.5 mM EDTA, and 0.1% ascorbate. The potency of alpha-1 antagonists at $5HT_2$ receptors was determined in equilibrium competition binding assays using [3H]ketanserin (1 nM). Nonspecific binding was defined by the addition of 10 μM mianserin. The bound radioligand was separated by filtration through GF/B filters using a cell harvester.

Human 5-HT$_7$ Receptor: A LM(tk−) clonal cell line stably transfected with the gene encoding the 5HT$_7$ receptor subtype was prepared as described above. The cell line for the 5HT$_7$ receptor, designated as L-5HT$_{4B}$, was deposited on Oct. 20, 1992, and accorded ATCC Accession No. CRL 11166.

Human Dopamine $D_3$ Receptor: The binding of compounds to the human $D_3$ receptor was determined using membrane preparations from COS-7 cells transfected with the gene encoding the human $D_3$ receptor. The human dopamine. D3 receptor was prepared using known methods. Sokoloff, P. et al., Nature, 347, 146 (1990), and deposited with the European Molecular Biological Laboratory (EMBL) Genbank as X53944). Cells were harvested after 72 hours and lysed by sonication in 5 mM Tris-HCl, 5 mM EDTA, pH 7.5. The cell lysates were centrifuged at 1000 rpm for 5 minutes at 4° C., and the supernatant was centrifuged at 30,000× g for 20 minutes at 4° C. The pellet was suspended in 50 mM Tris-HCl (pH 7.4) containing 1 mM EDTA, 5 mM KCl, 1.5 mM $CaCl_2$, 4 mM $MgCl_2$, and 0.1% ascorbic acid. The cell lysates were incubated with [$^3$H]spiperone (2 nM), using 10 μM (+)Butaclamol to determine nonspecific binding.

Membrane Harvest

Membranes were harvested from COS-7 cells 48 hours after transient transfection. Adherent cells were washed twice in ice-cold phosphate buffered saline (138 mM NaCl, 8.1 mM $Na_2HPO_4$, 2.5 mM KCl, 1.2 mM $KH_2PO_4$, 0.9 mM $CaCl_2$, 0.5 mM $MgCl_2$, pH 7.4) and lysed by sonication in ice-cold sonication buffer (20 mM Tris-HCl, 5 mM EDTA, pH 7.7). Large particles and debris were cleared by low speed centrifugation (200× g, 5 min, 4° C.). Membranes were collected from the supernatant fraction by centrifugation (32,000× g, 18 min, 4° C.), washed with ice-cold hypotonic buffer, and collected again by centrifugation (32,000× g, 18 min, 4° C.). The final membrane pellet was resuspended by sonication into a small volume of ice-cold binding buffer (~1 ml for every 5 plates: 10 mM NaCl, 20 mM HEPES, 0.22 mM $KH_2PO_4$, 1.26 mM $CaCl_2$, 0.81 mM $MgSO_4$, pH 7.4). Protein concentration was measured by the Bradford method (Bradford, 1976) using Bio-Rad Reagent, with bovine serum albumin as a standard. Membranes were held on ice for up to one hour and used fresh, or flash-frozen and stored in liquid nitrogen.

Membranes were prepared similarly from 293, LM(tk-), and NIH-3T3 cells. To prepare membranes from baculovirus infected cells, 2×10$^7$ Sf21 cells were grown in 150 mm tissue culture dishes and infected with a high-titer stock of hY5BB3. Cells were incubated for 2–4 days at 27° C., no $CO_2$ before harvesting and membrane preparation as described above.

Membranes were prepared similarly from dissected rat hypothalamus. Frozen hypothalami were homogenized for 20 seconds in ice-cold sonication buffer with the narrow probe of a Virtishear homogenizer at 1000 rpm (Virtis, Gardiner, N.Y.). Large particles and debris were cleared by centrifugation (200× g, 5 min, 4° C.) and the supernatant fraction was reserved on ice. Membranes were further extracted from the pellet by repeating the homogenization and centrifugation procedure two more times. The supernatant fractions were pooled and subjected to high speed centrifugation (100,000× g, 20 min. 4° C.). The final membrane pellet was resuspended by gentle homogenization into a small volume of ice-cold binding buffer (1 mL/ gram wet weight tissue) and held on ice for up to one hour, or flash-frozen and stored in liquid nitrogen.

Radioligand Binding to Membrane Suspensions

Membrane suspensions were diluted in binding buffer supplemented with 0.1 bovine serum albumin to yield an optimal membrane protein concentration so that $^{125}$I-PYY (or alternative radioligand such as $^{125}$I-NPY, $^{125}$I-$PYY_{3-36}$, or $^{125}$I-[Leu$^{31}$Pro$^{34}$]PYY) bound by membranes in the assay was less than 10% of $^{125}$I-PYY (or alternative radioligand) delivered to the sample (100,000 dpm/sample=0.08 nM for competition binding assays). $^{125}$I-PYY (or alternative radioligand) and peptide competitors were also diluted to desired concentrations in supplemented binding buffer. Individual samples were then prepared in 96-well polypropylene microtiter plates by mixing $^{125}$I-PYY (25 μL) (or alternative radioligand), competing peptides or supplemented binding buffer (25 μl), and finally, membrane suspensions (200 μl). Samples were incubated in a 30° C. water bath with constant shaking for 120 min. Incubations were terminated by filtration over Whatman GF/C filters (pre-coated with 1% polyethyleneimine and air-dried before use), followed by washing with 5 mL of ice-cold binding buffer. Filter-trapped membranes were impregnated with MultiLex solid scintillant (Wallac, Turku, Finland) and counted for $^{125}$I in a Wallac BetaPlate Reader. Non-specific binding was defined by 300 nM human NPY for all receptors except the Y4 subtypes; 100 nM human PP was used for the human Y4 and 100 nM rat PP for the rat Y4. Specific binding in time course and competition studies was typically 80%; most nonspecific binding was associated with the filter. Binding data were analyzed using nonlinear regression and statistical techniques available in the GraphPAD Prism package (San Diego, Calif.).

Functional Assay: Radioimmunoassay of cAMP

Stably transfected cells were seeded into 96-well microtiter plates and cultured until confluent. To reduce the potential for receptor desensitization, the serum component of the media was reduced to 1.5% for 4 to 16 hours before the assay. Cells were washed in Hank's buffered saline, or HBS (150 mM NaCl, 20 mM HEPES, 1 mM $CaCl_2$, 5 mM KCl, 1 mM $MgCl_2$, and 10 mM glucose) supplemented with 0.1% bovine serum albumin plus 5 mM theophylline and pre-equilibrated in the same solution for 20 min at 37° C. in 5% $CO_2$. Cells were then incubated 5 min with 10 μM forskolin and various concentrations of receptor-selective ligands. The assay was terminated by the removal of HBS and acidification of the cells with 100 mM HCl. Intracellular cAMP was extracted and quantified with a modified version of a magnetic bead-based radioimmunoassay (Advanced Magnetics, Cambridge, Mass.). The final antigen/antibody complex was separated from free $^{125}$I-cAMP by vacuum filtration through a PVDF filter in a microtiter plate (Millipore, Bedford, Mass.). Filters were punched and counted for $^{125}$I in a Packard gamma counter. Binding data were analyzed using nonlinear regression and statistical techniques available in the GraphPAD Prism package (San Diego, Calif.).

Functional Assay: Intracellular calcium mobilization

The intracellular free calcium concentration was measured by microspectroflourometry using the fluorescent indicator dye Fura-2/AM (ref). Stably transfected cells were seeded onto a 35 mm culture dish containing a glass coverslip insert. Cells were washed with HBS and loaded with 100 μl of Fura-2/AM (10 μM) for 20 to 40 min. After washing with HBS to remove the Fura-2/AM solution, cells were equilibrated in HBS for 10 to 20 min. Cells were then visualized under the 40× objective of a Leitz Fluovert FS microscope and fluorescence emission was determined at 510 nM with excitation wave lengths alternating between 340 nM and 380 nM. Raw fluorescence data were converted to calcium concentrations using standard calcium concentration curves and software analysis techniques.

Tissue Preparation for neuroanatomical studies

Male Sprague-Dawley rats (Charles Rivers) were decapitated and the brains rapidly removed and frozen in isopentane. Coronal sections were cut at 11 μm on a cryostat and thaw-mounted onto poly-L-lysine coated slides and stored at −80° C. until use. Prior to hybridization, tissues were fixed in 4% paraformaldehyde, treated with 5 mM dithiothreitol, acetylated in 0.1 M triethanolamine containing 0.25% acetic anhydride, delipidated with chloroform, and dehydrated in graded ethanols.

Probes

The oligonucleotide probes employed to characterize the distribution of the rat NPY Y5 mRNA were complementary to nucleotides 1121 to 1165 in the 5,6-loop of the rat Y5 mRNA (FIG. 3A) 45mer antisense and sense oligonucleotide probes were synthesized on a Millipore Expedite 8909 Nucleic Acid Synthesis System. The probes were then lyophilized, reconstituted in sterile water, and purified on a 12% polyacrylamide denaturing gel. The purified probes were again reconstituted to a concentration of 100 ng/μl, and stored at −20° C.

In Situ Hybridization

Probes were 3'-end labeled with $^{35}$-dATP (1200 Ci/mmol, New England Nuclear, Boston, Mass.) to a specific activity of $10^9$ dpm/μg using terminal deoxynucleotidyl transferase (Pharmacia). The radiolabeled probes were purified on Biospin 6 chromatography columns (Bio-Rad; Richmond, Calif.), and diluted in hybridization buffer to a concentration of $1.5 \times 10^4$ cpm/μl. The hybridization buffer consisted of 50% formamide, 4× sodium citrate buffer (1× SSC=0.15 M NaCl and 0.015 M sodium citrate), 1× Denhardt's solution (0.2% polyvinylpyrrolidine, 0.2% Ficoll, 0.2% bovine serum albumin), 50 mM dithiothreitol, 0.5 mg/ml salmon sperm DNA, 0.5 mg/ml yeast tRNA, and 10% dextran sulfate. One hundred μl of the diluted radiolabeled probe was applied to each section, which was then covered with a Parafilm coverslip. Hybridization was carried out overnight in humid chambers at 40 to 55° C. The following day the sections were washed in two changes of 2× SSC for one hour at room temperature, in 2× SSC for 30 min at 50–60° C., and finally in 0.1× SSC for 30 min at room temperature. Tissues were dehydrated in graded ethanols and exposed to Kodak XAR-5 film for 3 days to 3 weeks at −20° C., then dipped in Kodak NTB3 autoradiography emulsion diluted 1:1 with 0.2% glycerol water. After exposure at 4° C. for 2 to 8 weeks, the slides were developed in Kodak D-19 developer, fixed, and counterstained with cresyl violet.

Hybridization controls

Controls for probe/hybridization specificity included hybridization with the radiolabeled sense probe, and the use of transfected cell lines. Briefly, COS-7 cells were transfected (see above) with receptor cDNAs for the rat Y1, Y2 (disclosed in U.S. patent application Ser. No. 08/192,288, filed Feb. 3, 1994), Y4 (disclosed in U.S. patent application Ser. No. 08/176,412, filed Dec. 28, 1993), or Y5. As described above, the transfected cells were treated and hybridized with the radiolabeled Y5 antisense and sense oligonucleotide probes, washed, and exposed to film for 1–7 days.

Analysis of hybridization signals

Sections through the rat brain were analyzed for hybridization signals in the following manner. "Hybridization signal" as used in the present context indicates the relative number of silver grains observed over neurons in a selected area of the rat brain. Two independent observers rated the intensity of the hybridization signal in a given brain area as nonexistent, low, moderate, or high. These were then converted to a subjective numerical scale as 0, +1, +2, or +3 (see Table 10), and mapped on to schematic diagrams of coronal sections through the rat brain (see FIG. 11).

Chemical synthetic methods

Compounds evaluated in the in vitro Y5 receptor binding and functional assays, and in vivo feeding assays of the present invention were synthesized according to the methods described below. It is generally preferred that the respective product of each process step, as described hereinbelow, is separated and/or isolated prior to its use as starting material for subsequent steps. Separation and isolation can be effect by any suitable purification procedure such as, for example, evaporation, crystallization, column chromatography, thin layer chromatography, distillation, etc. While preferred reactants have been identified herein, it is further contemplated that the present invention would include chemical equivalents to each reactant specifically enumerated in this disclosure.

Temperatures are given in degrees Centigrade (°C). The structure of final products, intermediates and starting materials is confirmed by standard analytical methods, e.g., microanalysis and spectroscopic characteristics (e.g. MS, IR, NMR). Unless otherwise specified, chromatography is carried out using silica gel. Flash chromatography refers to medium pressure column chromatography according to Still et al., J. Org. Chem. 43, 2928 (1978).

Synthesis of Compounds 1, 2, 5. 6, 7, 9, 10, and 11

For Compounds 1, 2, 5, 6, 7, 9, 10, and 11, thin layer chromatography was performed using the following solvent system:

| A1: | dichloromethane/methanol | 9:1 |
|---|---|---|
| A2: | dichloromethane/methanol | 19:1 |
| A3: | dichloromethane/methanol/ammonium hydroxide | 90:10:1 |
| B1: | toluene/ethylacetate | 1:1 |
| B2: | toluene/ethylacetate | 10:1 |
| C1: | hexanes/ethylacetate | 4:1 |
| C2: | hexanes/ethylacetate | 3:1 |
| C3: | hexanes/ethylacetate | 2:1 |

Compound 1: 2,4-Diphenylamino-quinazoline hydrochloride

2-Chloro-4-phenylamino-quinazoline (7.671 g) and aniline (3.627 g) are heated for 3 min to produce a melt which is dissolved in methanol. The product is obtained as its hydrochloride salt upon addition of a slight excess of 4N HCl in dioxane. Recrystallization from isopropanol yields 2,4-diphenylamino-quinazoline hydrochloride, m.p. 319–320° C., FAB-MS (Fast Atom Bombardment Mass Spectroscopy): $(M+H)^+=313$. Analytical data: $C_{20}H_{16}N_4$+HCl+0.5 $H_2O$, m.p. 319–320° C.

The starting material can be prepared as follows:

a) 2-Chloro-4-phenylamino-quinazoline

A solution of 2,4-dichloro-quinazoline (15 g), N,N-diisopropyl-ethylamine (24.9 ml) and aniline (7.5 ml) in isopropanol (75 ml) is heated to reflux for 45 min. The cold reaction mixture is filtered and the filtrate is concentrated in vacuo. The residue is crystallized from diethylether- toluene (1:1) to give 2-chloro-4-phenylamino-quinazoline, m.p. 194–196° C.

b) 2,4-Dichloro-quinazoline

N,N-Dimethylaniline (114.0 g) is added slowly to a solution of 1H,3H-quinazolin-2,4-dione (146.0 g) in phosphorousoxychloride (535.4 ml) while this mixture is heated up to 140° C. After completion of the addition reflux is continued for 20 h. The reaction mixture is filtered and evaporated to give a residue which is added to ice and water. The product is extracted with dichloromethane and crystallized from diethylether and petroleum diethylether to yield 2,4-dichloro-quinazoline, m.p. 115–116° C.

Compound 2: Naphthalene-1-sulfonic acid [6-(4-aminoquinazolin-2-ylamino)-hexyl]-amide A solution of naphthalene-1-sulfonic acid (6-aminohexyl)-amide (0.450 g) and 2-chloro-quinazolin-4-ylamine (see: U.S. Pat. No. 3,956,495) (0.264 g) in 20 ml of isopentylalcohol is heated up to 120° C. for 15 h. Concentration of the reaction mixture followed by chromatography on silica gel (B1) yields naphthalene-1-sulfonic acid [6-(4- amino-quinazolin-2-ylamino)-hexyl]amide as a white powder, melting at 98–101° C. Rf(B1) 0.28, FAB-MS: (M+H)⁺=450. Ananlytical $C_{26}H_{29}N_5O_2S+HCl+H_2O+0.6$ 1,4 dioxane. m.p. 98–101° C.

Compound 5: trans-Naphthalene-1-sulfonic acid {4-[(4-amino-quinazolin-2-ylamino)-methyl]-cyclohexylmethyl}amide hydrochloride A suspension of 2-chloro-quinazolin-4-ylamine (7.02 g) and trans-naphthalene-1-sulfonic acid (4-aminomethylcyclohexylmethyl)-amide (13 g) in 250 ml of isopentyl-alcohol is heated up to 120° C. for 15 h. The resulting solution is concentrated and chromatographed (silica gel, B2) to give the product as a foam. This material is taken up in dichloromethane (250 ml) and treated at 0° C. with a 4 N HCl solution in dioxane (10 ml). Concentration in vacuo provides a foam which is triturated in boiling cyclohexane to yield after filtration trans-naphthalene-1-sulfonic acid {4-[(4-amino-quinazolin-2-ylamino)methyl]-cyclohexylmethyl}-amide hydrochloride melting at 155–164° C. Rf(B2) 0.23, FAB-MS: (M+H)⁺=476. m.p. 155–164° C.

The starting material is prepared as follows:

a) trans-(4-Hydroxymethyl-cyclohexylmethyl)-carbamic acid tert-butyl ester

A solution of trans-4-(tert-butoxycarbonylamino-methyl) cyclohexanecarboxylic acid (obtained according to: EP 0614 911 A1) (34.5 g) and triethylamine (28 ml) in dichloromethane (700 ml) is cooled to –70° C. and treated with methylchloroformate (12.9 ml). The reaction mixture is stirred 0.5 h at –70° C. The temperature is allowed to increase to 0° C. and the solution is stirred another 0.5 h until completion of the reaction. The reaction mixture is taken up in ice-cold dichloromethane, washed with an ice-cold 0.5 N HCl solution, a saturated aqueous sodium carbonate solution and water. The organics are dried over sodium sulfate and concentrated to 41.3 g of mixtanhydride as an oil. This material is taken up in THF and treated at –70° C. with sodium borohydride (5.90 g), followed by absolute methanol (10 ml). The reaction mixture is stirred 15 h at 0° C. and 1 h at ambient temperature to drive the reaction to completion. A 0.5 N HCl solution is then carefully added at 0° C., followed by ethyl acetate. The organics are washed with a saturated aqueous sodium carbonate solution, water, dried over sodium sulfate and concentrated. Chromatography on silica gel (A1) yields trans-(4-hydroxymethyl-cyclohexylmethyl)carbamic acid tert-butyl ester as a white powder, melting at 88–89° C. Rf(A1) 0.24.

b) trans-(4-Azidomethyl-cyclohexylmethyl)-carbamic acid tert-butyl ester trans-(4-Hydroxymethyl-cyclohexylmethyl)-carbamic acid tert-butyl ester (24 g) in pyridine (200 ml) at 0° C. is treated with a solution of para-toluenesulfonylchloride (24.44 g) in pyridine (50 ml). The reaction mixture is stirred at 0° C. until completion and concentrated in vacuo. The residue is taken up in ethyl acetate, washed with water and dried over sodium sulfate. Concentration of the solution yields the tosylate, used without further purification. This material is treated with sodium azide (19.23 g) in N,N-dimethylformamide (800 ml) at 50° C. After completion of the reaction, the solution is concentrated and the resulting paste is taken up in dichloromethane, washed with water and concentrated. Chromatography of the crude material on silica gel (A2 then A3) provides trans-(4-azidomethyl-cyclohexylmethyl) carbamic acid tert-butyl ester as an oil. Rf(A3) 0.33; IR (dichloromethane) λ max 2099 cm⁻¹.

c) trans-(4-Aminomethyl-cyclohexylmethyl)-carbamic acid tert-butyl ester trans-(4-Azidomethyl-cyclohexylmethyl)-carbamic acid tert-butyl ester (24 g) in ethyl acetate (1 liter) is hydrogenated over platinumoxide (2.4 g) at ambient temperature under atmospheric pressure of hydrogen. The catalyst is filtered-off and the filtrate concentrated to yield trans-(4-aminomethyl-cyclohexylmethyl)-carbamic acid tert-butyl ester as an oil. Rf(C2) 0.41.

d) trans-{4-[(Naphthalene-1-sulfonylamino)-methyl] cyclohexylmethyl}-carbamic acid tert-butyl ester A solution of trans-(4-aminomethyl-cyclohexylmethyl) carbamic acid tert-butyl ester (17 g) and ethyldiisopropylamine (14.41 ml) in N,N-dimethylformamide (350 ml) is cooled to 0° C. and treated with a solution of naphthalene-1-sulfonylchloride (15.9 g) in N,N-dimethylformamide (100 ml). The reaction is stirred at ambient temperature for 2 h, concentrated in vacuo. The residue is taken up in dichloromethane, washed with a 0.5 N HCl solution, a saturated aqueous sodium carbonate solution and water, dried and concentrated. Crystallization from hexanes-ethyl acetate gives trans-{4-[(naphthalene-1-sulfonylamino)-methyl]cyclohexylmethyl}-carbamic acid tert-butyl ester as a white powder, melting at 199–200° C. Rf (A1) 0.42.

e) trans-Naphthalene-1-sulfonic acid (4-aminomethylcyclohexylmethyl)-amide

A suspension of trans-{4-[(naphthalene-1-sulfonylamino) methyl]-cyclohexylmethyl}-carbamic acid tert-butyl ester (25 g) in chloroform (300 ml) is treated with a 4 N HCl solution in dioxane (300 ml) at 0° C. After completion, the reaction mixture is concentrated in vacuo, the residue is taken up in a 1 N sodium hydroxide solution and dichloromethane. After extraction with dichloromethane, the organics are dried over sodium sulfate and concentrated to 18.5 g of trans-naphthalene-1-sulfonic acid (4-aminomethyl-cyclohexylmethyl)-amide as a white powder melting at 157–162° C. Rf(C3) 0.36.

Compound 6: 2-[4-(Piperidin-1-yl)-phenylamino]-4-phenylamino-quinazoline dihydrochloride A mixture of 2-chloro-4-phenylamino-quinazoline (0.18 g) and N-(4-aminophenyl)-piperidine (0.164 g) is heated for 3 min to produce a melt which is dissolved in isopropanol (4 ml). 4 N HCl in dioxane (1 ml) is added. Recrystallization from ethanol and diethylether yields 2-[4-(piperidin-1-yl) -phenylamino]-4-phenylamino-quinazoline dihydrochloride, Rf (A1) 0.64, FAB-MS: (M+H)⁺=396. m.p.: (decomposition).

Compound 7: trans-2-(4-Acetoxy-cyclohexylamino)-4-phenylamino-quinazoline hydrochloride A solution of trans-2-(4-hydroxy-cyclohexyamino)-4-phenylamino-quinazoline hydrochloride (1.3 g) and acetic anhydride (0.33 ml) in acetic acid (5 ml) is stirred at ambient temperature for 16 h. The solvent is removed in vacuo and the residue is added to 2N aqueous NaOH. Extraction with ethyl acetate followed by chromatography on silica gel (A4) gives a crude product which is treated with 4 N HCl in dioxane. Crystallization from acetonitrile and acetone yields trans-2-(4-acetoxycyclohexylamino)-4-phenylamino-quinazoline hydrochloride, m.p. 217–220° C; FAB-MS: (M+H)⁺=377; analytical data: $C_{22}H_{24}N_4O_2$+HCl.

The starting material is prepared as follows:

a) 2-(4-Hydroxy-cyclohexyamino)-4-phenylamino-quinazoline hydrochloride

A mixture of 2-chloro-4-phenylamino-quinazoline (2.3 g) and trans-4-amino-cyclohexanol (1.26 g) is heated for 3 min to produce a melt which is dissolved in isopropanol. 4 N HCl in dioxane (0.1 ml) is added. Crystallization from isopropanol and acetone yields 2-(4-hydroxycyclohexyamino)-4-phenylamino-quinazoline hydrochloride, m.p. 258–259° C.

Compound 9: 8-Methoxy-2-(4-methoxy-phenylamino)-4-phenylamino-quinazoline hydrochloride A mixture of 2-chloro-8-methoxy-4-phenylamino-quinazoline (1.20 g) and 4-methoxy-aniline (0.66 g) is heated for 3 min to produce a melt which is dissolved in isopropanol (15 ml). 4N HCl in dioxane (0.2 ml) is added. Crystallization from isopropanol and diethylether yields 8-methoxy-2-(4-methoxy-phenylamino)-4-phenylamino-quinazoline dihydrochloride, m.p. 287–289° C., FAB-MS: (M+H)$^+$=373. Analytical data: $C_{22}H_{20}N_4O_2$+HCl.

The starting material can be prepared as follows:

a) 2-Chloro-8-methoxy-4-phenylamino-quinazoline

A solution of 2,4-dichloro-8-methoxy-quinazoline (prepared as described in *J. Chem. Soc.* 1948, 1759) (0.6 g), N,N-diisopropyl-ethylamine (0.87 ml), and aniline (0.26 ml) in isopropanol (10 ml) is heated to reflux for 45 min. The cold reaction mixture is filtered and residue is crystallized from dichloromethane and hexanes to give 2-chloro-8-methoxy-4-phenylamino-quinazoline, m.p. 245–246° C.

Compound 10: N-Methyl-[4-(6-methoxy-4-phenylamino-quinazolin-2-ylamino)-phenyl]-methanesulfonamide hydrochloride A solution of 2-chloro-6-methoxy-4-phenylamino-quinazoline (1.15 g) and N-methyl-(4-aminophenyl)-methanesulfonamide (prepared as described in *Tetrahedron Letters* 1992, 33, 8011) (0.89 g) in 5 ml of isopentylalcohol is stirred under nitrogen at 180° C. for 20 min in a sealed vessel. The warm reaction mixture is diluted with methanol and the hydrochloride salt, which is crystallizing on cooling, is filtered off. The crude product is redissolved in ethylacetate and aqueous sodium carbonate solution and extracted with ethylacetate. The organic extracts are dried and evaporated and the solid residue is titurated with diethylether to give N-methyl-[4-(6-methoxy-4-phenylamino-quinazolin-2-ylamino)-phenyl]-methanesulfonamide as light yellow crystals melting at 212–215° C.; (Rf (A2) 0.16. Recrystallisation from methanolic hydrogen chloride and diethylether yields N-methyl-[4-(6-methoxy-4-phenylamino-quinazolin-2-ylamino)-phenyl]-methanesulfonamide hydrochloride as light yellow crystals melting at 264–268° C.; Rf (A2) 0.16, FAB-MS: (M+H)$^+$=450. Analytical data: $C_{23}H_{23}N_5O_3S$+HCl.

The starting material can be prepared as follows:

a) 2-Chloro-6-methoxy-4-phenylamino-quinazoline

In a procedure analogous to that of Example 1a 2,4-dichloro-6-methoxy-quinazoline (1.53 g) (prepared as described in *J. Chem. Soc.* 1948, 1759), aniline (0.8 g) (0.184 g) and N,N-diisopropyl-ethylamine (1.72 g) are reacted together to give 2-chloro-6-methoxy-4-phenylamino-quinazoline as light yellow crystals melting at 177–179° C., Rf (A2) 0.59.

Compound 11: N-Methyl-[4-(4-phenylamino-quinazolin-2-ylamino)-phenyl]-methanesulfonamide hydrochloride A solution of 2-chloro-4-phenylamino-quinazoline (0.92 g) (prepared as described in Example 1a and N-methyl-(4-aminophenyl)-methanesulfonamide (0.80 g) in 10 ml of isopentylalcohol is stirred under nitrogen at 170° C. for 15 min in a sealed vessel. The warm reaction mixture is diluted with 10 ml ethanol and the hydrochloride salt, which is crystallizing on cooling, is filtered off to yield N-methyl-[4-(4-phenylamino-quinazolin-2-ylamino)-phenyl]-methanesulfonamide hydrochloride as light yellow crystals melting at 259–263° C.; Rf (A2) 0.11, FAB-MS: (M+H)$^+$=420. Analytical data: $C_{22}H_{21}N_5O_2S$+HCl.

Synthesis of Compounds 17–23, Compound 26 and Compound 27.

Compounds 17–23, 26 and 27 were synthesized according to the general method in Scheme 1, as described below. An example of the synthesis of a specific compound, Compound 17, follows the general description. Compounds 18–23, 26 and 27 were synthesized in the same manner but using the appropriately substituted starting materials.

Preparation of the compounds of the present invention having the structure shown in Formula 1–3, Scheme 1, is carried out using well-known methodology for the preparation of a sulfonamide from an amine. Preferably the appropriate arylsulfonyl halide, preferably the chloride (i.e., Ar-SO$_2$Cl), is reacted with a monoprotected linear or cyclic alkylamine (Krapcho and Kuell, *Synth. Comm.* 20(16) :2559–2564, 1990) comprising H$_2$N-L-K", where K" comprises methylene, in the presence of a base such as a tertiary amine, e.g., triethylamine, dimethylaminopyridine, pyridine or the like, in an appropriate solvent (e.g. CHCl$_3$, CH$_2$Cl$_2$) as shown in Scheme 1, step A, followed by deprotection of the resulting amine as shown in Scheme 1, Step B, all under mild conditions (typically room temperature), to yield the deprotected amine of Formula 1-1. The arylsulfonyl halides are either known in the art or can be prepared according to methods well known in the art.

Compounds of Formula 1-2 in Scheme 1, may be synthesized from the compound of Formula 1-1 by amidation using suitable methods such as those taught in "The Peptides," Vol. 1 (Gross and Meinehofer, Eds. Acaemic Press, N.Y., 1979). For example, the compound of Formula 1-1 may be treated with a carboxylic acid derivative of W in the presence of 1-(3-dimethylaminopropyl)-3-ethylcarbodiimide hydrochloride (EDC) and dimethylaminopyridine (DMAP) in a suitable solvent such as CH$_2$Cl$_2$ as shown in Scheme 1, Step C, at room temperature in an inert atmosphere of argon or nitrogen, to yield the amide compound of Formula 1-2. The K" amine and the carboxylic acid carbon attached to W together form K in the product.

Alternatively, the compound of Formula 1-2 may be synthesized by acylation of the amine of Formula 1-1 using the acid chloride of W, i.e., WCOCl, in a solvent such as CH$_2$Cl$_2$ and a suitable tertiary amine such as triethylamine, at room temperature. Again, the K" amine and the acid chloride carbon attached to W together form K in the product.

The product compounds of Formula 1-3 are then formed by reduction of the amide of Formula 1-3 using borane-tetrahydorfuran (THF) complex, in THF as shown in Scheme 1, Step D, at elevated temperature in an inert atmosphere.

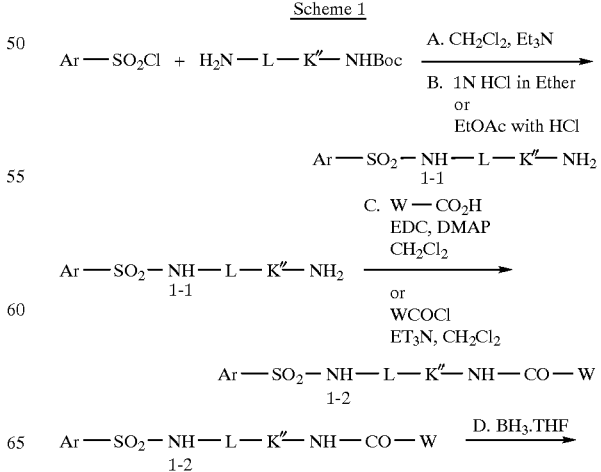

Ar—SO$_2$—NH—L—K—W
1-3

As a specific example of the synthesis of compounds 17–23, 26 and 27, the synthesis of Compound 17 is given hereinbelow.

Compound 17: Naphthalene-2-sulfonic acid(4-[{(1, 2, 3, 4-tetrahydronaphthalen-2-yl)methyl}-amino]-transyclohexylmethyl)-amide Step A Scheme 1

{4-[(Naphthalene-2-sulfonylamino)-transcyclohexylmethyl]-carbamic acid tert-butyl ester:

To a stirred solution of (4-aminomethylcyclohexylmethyl)carbamic acid tert-butyl ester(0.50 g, 2.1 mmol) and triethyl amine (0.42 g, 4.2 mmol) in 50 mL methylene chloride was added 2-naphthalenesulfonyl chloride (0.51 g, 2.3 mmol). The reaction mixture was stirred for 6 h at room temperature, quenched with brine, and extracted with methylene chloride (2×50 mL). The organic layer was washed with brine, dried over anhydrous sodium sulfate, and concentrated in vacuo to yield the titled compound as white solid(0.74 g, 83%): mp 114–5° C.

Step B, Scheme 1

Naphthalene-2-sulfonic acid-(4-aminomethyl-transcyclohexylmethyl)-amide:

To a stirred solution of {4-[(naphthalene-2-sulfonylamino)-transcyclohexylmethyl]-carbamic acid tert-butyl ester(0.73 g, 1.6 mmol) in 25 mL of methylene chloride at room temperature was added 3 mL of saturated HCl solution in ethyl acetate and stirred for 4 h. The precipitated solid was filtered to yield the titled compound as white solid (0.58 g, 99%); mp 286–7° C.

Step C, Scheme 1

1, 2, 3, 4-Tetrahydronaphthalene-2-carboxylic acid[4-{(naphthalen-2-sulfonylamino)methyl}-tanscyclohexylmethyl]amide A mixture of naphthalene-2-sulfonic acid-(4-aminomethyltrans-cyclohexylmethyl)amide(0.5 g, 1.4 mmol), EDC (0.54 g, 2.8 mmol), and DMAP (0.34 g, 2.8 mmol) in methylene chloride(30 mL) was stirred at room temperature for 0.5 h. 1,2,3,4-tetrahydronaphthalen-2-carboxylic acid (0.24 g, 1.4 mmol) was added to the reaction mixture and stirred at room temperature till the completion of the reaction(by TLC). The reaction mixture was washed with saturated ammonium chloride (3×30 mL), dried over sodium sulfate and concentrated in vacuo. The residue was flash chromatographed over silica gel to afford white solid (0.66 g, 99%); mp 225–6° C.

Step D, Scheme 1

Naphthalene-2-sulfonic acid(4-[{(1, 2, 3, 4-tetrahydronaphthalen-2-yl)methyl}-amino]-transcyclohexylmethyl)-amide To a solution of 1, 2, 3, 4-tetrahydronaphthalen-2-carboxylic acid[4-{(naphthalen-2-sulfonylamino) methyl}tanscyclohexylmethyl]amide(0.65 g, 1.3 mmol) in tetrahydrofuran(5 mL) cooled to 0° C. was added 6.6 mL 1M solution of borane:THF complex and the reaction mixture was refluxed for 12 h. The reaction mixture was cooled in ice bath and quenched with 2 mL of 1N HCl. The reaction mixture was neutralized with 10% aqueous sodium hydroxide solution and extracted with ethyl acetate (3×25 mL). Organic phase was washed with the brine, dried over sodium sulfate, evaporated in vacuo to afford an oil which was purified by preparative TLC to afford the titled compound (0.44 g, 70%); hydrochloride salt mp (210° C.).

In order to synthesize compounds 18–24, 26 and 27, the 2-naphthalenesulfonyl chloride of Step A above, which comprises the "Ar" moiety of Table 2, is replaced with the appropriate Ar- sulfonyl chloride, and the 1,2,3,4-tetrahydronaphthalen-2-carboxylic acid used in Step C above, which comprises the "W" moiety of Table 2, is replaced with the appropriate W-carboxylic acid, to yield product containing the corresponding Ar and W moieties shown in Table 2.

Synthesis of Compound 25

Compound 25 was synthesized according to Scheme 2. After protection of H$_2$N—L—COOH with Boc anhydride in CH$_2$Cl$_2$, as shown in Scheme 2, Step A, the protected amine may be amidated with W—K''' as in Scheme 2, Step B, where K''' is (CH$_2$)jCHR$_7$—NH$_2$, where R$_7$ is an ester and j is 1 using EDC and DMAP in a suitable solvent such as CH$_2$Cl$_2$, to yield compounds of Formula 3-1, where K''' and the carboxylic acid carbonyl of H$_2$N—L—COOH together form K. The compounds of Formula 3-1 may be deprotected using well known methods as shown in Scheme 2, Step C, and further sulfonylated with a sulfonyl halide of Ar, as shown in Scheme 2, Step D, in a suitable solvent such as CH$_2$Cl$_2$ and a tertiary amine such as triethylamine, to form the compound of Formula 3-3. Compounds of Formula 3-3 may be reduced to yield the compounds of Formula 3-3, as shown in Scheme 2, Step E, using borane-tetrahydorfuran (THF) complex, in THF, at elevated temperature in an inert atmosphere.

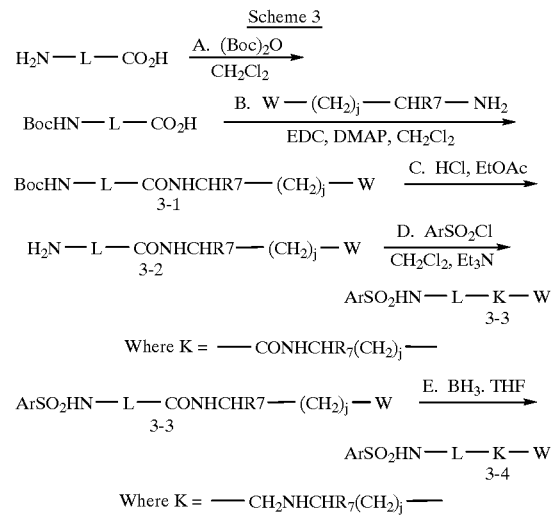

A detailed description of the synthesis of Compound 25 is given below:

Compound 25: trans-3-(4-Chloro-phenyl)-2-({[4-(naphthalene-1-sulfonylamino)-methyl] cyclohexanecarbonyl}-amino]-propionic acid methyl ester:

(a) Step A, Scheme 2 trans-4- (tert-Butoxycarbonylamino-methyl)-cyclohexanecarboxylic acid:

To a solution of trans-4-(aminomethyl) cyclohexanecarboxylic acid (10 g, 57 mmol) in 1 N NaOH (110 mL) cooled to 0° C. was added a solution of di-tert-butyl dicarbonate (15 g, 69 mmol) in dioxane (50 mL). The reaction mixture was stirred at 0° C. for 12 h. The reaction mixture was neutralized by 1 N HCl solution to pH 3, extracted with ethyl ether (2×300 mL), washed with brine (2×300 mL), dried over anhydrous magnesium sulfate, and concentrated in vacuo to afford the titled compound (16 g, 100%); white solid, mp 128–9° C.

(b) Step B, Scheme 2
trans-2-{[4-(tert-Butoxycarbonylamino-methyl)-cyclohexanecarbonyl]-amino}3-(4-Chloro-phenyl)-propionic acid methyl ester:

Using the general procedure described for the preparation Step B, Scheme 2, trans-4-(tert-butoxycarbonylaminomethyl)-cyclohexanecarboxylic acid (1.1 g, 4.0 mmol) was acylated with D,L-4-chlorophenylalanine methyl ester hydrochloride (1.0 g, 4.0 mmol) to afford the titled compound (1.9 g, 99%); white solid, mp 178–9° C.

(c) Step C, Scheme 2
trans-2-[4-(Aminomethyl-cyclohexanecarbonyl)-amino]3-(4-chloro-phenyl)-propionic acid methyl ester hydrochloride:

Using the general procedure described in step C Scheme 2, trans-2-{[4-(tert-butoxycarbonylamino-methyl)cyclohexanecarbonyl]-amino}3-(4-chloro-phenyl)-propionic acid methyl ester (1.8 g, 4.3 mmol) was deprotected using HCl in ethyl acetate to afford the titled compound; light yellow solid mp 146–9° C.

(d) Step D, Scheme 2
trans-3-(4-Chloro-phenyl)-2-({[4-(naphthalene-1-sulfonylamino)-methyl]-cyclohexanecarbonyl}-amino] propionic acid methyl ester:

Using the general procedure described in step B Scheme 2, trans-2-[4-(aminomethyl-cyclohexanecarbonyl)-amino]-3-(4-Chloro-phenyl)-propionic acid methyl ester hydrochloride (0.35 g, 0.86 mmol) was sulfonylated with 1-naphthalenesulfonyl chloride (0.42 g, 91%) to afford the titled compound; white solid, mp 84–6° C.

Compound 25 was synthesized from the above compound by borane-THF reduction as follows:

(e) Step E, Scheme 2
Naphthalene-1-sulfonic Acid trans- (4-{[2-(4-Chlorophenyl)-1-hydroxymethyl-ethylamino]-methyl}cyclohexylmethyl)-amide:

Using the general procedure described in Step E, Scheme 2, trans-3-(4-chloro-phenyl)-2-({[4-(naphthalene-1-sulfonylamino)-methyl]-cyclohexanecarbonyl}-amino]-propionic acid methyl ester (0.30 g, 0.55 mmol) was reduced by borane:THF complex (1.0 M in THF) to afford the titled compound; colorless oil.

Synthesis of Compound 28

2-(Naphthalen-1-ylamino)-3-phenylpropionitrile

To a solution of 1-naphthalenemethylamine (2.9 g, 20 mmol) and benzylaldehyde (2.0 g, 17 mmol) in 30 ml of $CHCl_3$ and 10 ml of MeOH was added TMSCN (6.6 ml, 51 mmol) and the resulting solution was stirred for 12 h at 25° C. The reaction mixture was concentrated in vacuo, yielding an oil which was subjected to column chromatography (EtOAc, neat) to provide 3.5 g (74%) of the desired product as a colorless oil. Product was identified by NMR.

2-(Naphthalen-1-yl)-3-phenylpropane-1,2-diamine

To a solution of the nitrile (0.5 g, 1.8 mmol) in THF was added 6.9 ml of 1N $LiAlH_4$ in THF dropwise and the resulting solution was stirred for 2 h. The reaction was quenched by adding a few pieces of ice into the solution. The reaction mixture was diluted with EtOAc and filtered through pad of Celite. Organic filtrate was concentrated in vacuo to provide a oily residue which was subjected to column chromatography (EtOAc, neat) to provide 0.28 g (57%) of the desired product as a colorless oil. The product was identified by NMR.

| No. | Ar | X | $R_1$ | L | K | W | mp | Analysis |
|---|---|---|---|---|---|---|---|---|
| 17 | naphthalen-2-yl | — | H | cyclohexyl (trans) | $CH_2NHCH_2$ | tetrahydronaphthalen-2-yl | 210 | $C_{29}H_{36}N_2O_2S$ + HCl |
| 19 | naphthalen-1-yl | — | H | cyclohexyl (trans) | $CH_2NHCH_2$ | tetrahydronaphthalen-2-yl | 220 | $C_{29}H_{36}N_2O_2S$ + HCl + 0.15 $CH_2Cl_2$ |
| 20 | 2-nitrophenyl | — | H | cyclohexyl (trans) | $CH_2NHCH_2$ | tetrahydronaphthalen-2-yl | 200–2 | $C_{25}H_{33}N_3O_4S$ + HCl |
| 21 | 2-(trifluoromethyl)phenyl | — | H | cyclohexyl (trans) | $CH_2NHCH_2$ | naphthalen-2-yl | 171–4 | $C_{26}H_{29}N_2O_2SF_3$ + HCl + 0.075 $CHCl_3$ |

-continued

| No. | Ar | X | R₁ | L | K | W | mp | Analysis |
|---|---|---|---|---|---|---|---|---|
| 22 | 2-methyl-aniline (NH₂, CH₃) | — | H | cyclohexyl | CH₂NHCH₂ | methyl-tetrahydronaphthyl | 175–7 | $C_{25}H_{35}N_3O_2S$ + 2 HCl + 0.8 Et₂O |
| 23 | 2-methyl-(trifluoromethyl)benzene (CF₃, CH₃) | — | H | cyclohexyl | CH₂NHCH₂ | methyl-naphthyl | 216–7 | $C_{26}H_{29}N_2O_2SF_3$ + HCl |
| 25 | methyl-naphthyl | — | H | cyclohexyl | CH₂OH / CH₂NHCHCH₂ | 4-chloro-methylphenyl | 223–3 | $C_{27}H_{33}N_2O_3SCl$ + HCl |
| 26 | 2-methyl-nitrobenzene (NO₂, CH₃) | — | H | cyclohexyl | CH₂NHCH₂ | 2-methyl-quinolinyl | 89 dec | $C_{24}H_{28}N_4O_4S$ + 2 HCl |
| 27 | 2-methyl-nitrobenzene (NO₂, CH₃) | — | H | cyclohexyl | CH₂NHCH₂ | 4-methyl-quinolinyl | 104–6 | $C_{25}H_{28}N_4O_4S$ + 2 HCl + 0.2 CHCl₃ |

In vivo STUDIES IN RATS

Food intake in satiated rats

For these determinations food intake may be measured in normal satiated rats after intracerebroventricular application (i.c.v.) of NPY in the presence or absence of the test compound. Male Sprague Dawley rats (Ciba-Geigy AG, Sisseln, Switzerland) weighing between 180 g and 220 g are used for all experiments. The rats are individually housed in stainless steel cages and maintained on an 11:13 h light-dark cycle (lights off at 18:00 h) at a controlled temperature of 21–23° C. at all times. Water and food (NAFAG lab chow pellets NAFAG, Gossau, Switzerland) are available ad libidum.

Rats under pentobarbital anesthesia are stereotaxically implanted with a stainless steel guide cannula targeted at the right lateral ventricle. Stereotaxic coordinates, with the incisor bar set –2.0 mm below interaural line, are: –0.8 mm, anterior and +1.3 mm lateral to bregma. The guide cannula is placed on the dura. Injection cannulas extend the guide cannulas –3.8 mm ventrally to the skull surface. Animals are allowed at least 4 days of recovery postoperatively before being used in the experiments. Cannula placement is checked postoperatively by testing all rats for their drinking response to a 50 ng intracerebroventricular (i.c.v.) injection of angiotensin II. Only rats which drink at least 2.5 ml of water within 30 min. after angiotensin II injection are used in the feeding studies.

All injections are made in the morning 2 hours after light onset. Peptides are injected in artificial cerebrospinal fluid (ACSF) in a volume of 5 μl. ACSF contains: NaCl 124 mM, KCl 3.75 mM, CaCl₂ 2.5 mM, MgSO₄ 2.0 mM, KH₂PO₄ 0.22 mM, NaHCO₃ 26 mM and glucose 10 mM. Porcine-NPY (p-NPY) are dissolved in artificial cerebrospinal fluid (ACS). For i.c.v. injection the test compounds are preferably dissolved in DMSO/water (10%, v/v). The vehicle used for intraperitoneal (i.p.), subcutaneous (s.c.) or oral (p.o.) delivery of compounds is preferably water, physiological saline or DMSO/water (10% v/v), or cremophor/water (20% v/v), respectively.

Animals which are treated with both test compounds and porcine-NPY are treated first with the test compound. Then, 10 min. after i.c.v. application of the test compound or vehicle (control), or for i.p., s.c., or p.o. administration, 30–60 min after application of the test compound or vehicle, generally, NPY is administered by intracerebroventricular (i.c.v.) application.

Food intake may be measured by placing preweighed pellets into the cages at the time of NPY injection. Pellets are then removed from the cage subsequently at each selected time point and replaced with a new set of preweighed pellets. The food intake of animals treated with test compound may be calculated as a percentage of the food intake of control animals i.e., animals treated with vehicle. Alternatively, food intake for each group of animals subjected to a particular experimental condition may be expressed as the mean ±S.E.M. Statistical analysis is performed by analysis of variance using the Student-Newman-Keuls test.

Food intake in food-deprived rats

Food-deprivation experiments are conducted with male Sprague-Dawley rats weighing between 220 and 250 g. After receipt, the animals are individually housed for the duration of the study and allowed free access to normal food together with tap water. The animals are maintained in a room with a 12 h light/dark cycle (8:00 a.m. to 8:00 p.m. light) at 24° C. and monitored humidity. After placement into individual cages the rats undergo a 4 day equilibration period, during which they are habituated to their new environment and to eating a powdered or pellet diet NAFAG, Gossau, Switzerland).

At the end of the equilibration period, food is removed from the animals for 24 hours starting at 8:00 a.m. At the end of the fasting period compound or vehicle may be administered to the animals orally or by injection intraperitoneally or intravenously. After 10–60 min. food is returned to the animals and their food intake is monitored at various time periods during the following 24 hour period. The food intake of animals treated with test compound may be calculated as a percentage of the food intake of control animals (i.e., animals treated with vehicle). Alternatively, food intake for each group of animals subjected to a particular experimental condition may be expressed as the mean ±S.E.M.

Food intake in obese Zucker rats

The antiobesity efficacy of the compounds according to the present invention might also be manifested in Zucker obese rats, which are known in the art as an animal model of obesity. These studies are conducted with male Zucker fatty rats (fa/fa Harlan CPB, Austerlitz NL) weighing between 480 g and 500 g. Animals are individually housed in metabolism cages for the duration of the study and allowed free access to normal powdered food and water. The animals are maintained in a room with a 12 h light/dark cycle (light from 8:00 A.M. to 8:00 P.M.) at 24° C. and monitored humidity. After placement into the metabolism cages the rats undergo a 6 day equilibration period, during which they are habituated to their new environment and to eating a powdered diet. At the end of the equilibration period, food intake during the light and dark phases is determined. After a 3 day control period, the animals are treated with test compounds or vehicle (preferably water or physiological saline or DMSO/water (10%,v/v) or cremophor/water (20%,v/v)). Food intake is then monitored over the following 3 day period to determine the effect of administration of test compound or vehicle alone. As in the studies described hereinabove, food intake in the presence of drug may be expressed as a percentage of the food intake of animals treated with vehicle, or as the amount of food intake for a group of animals subjected to a particular experimental condition.

Materials

Cell culture media and supplements are from Specialty Media (Lavallette, N.J.). Cell culture plates (150 mm and 96-well microtiter) were from Corning (Corning, N.Y.). Sf9, Sf21, and High Five insect cells, as well as the baculovirus transfer plasmid, pBlueBacIII™, were purchased from Invitrogen (San Diego, Calif.). TMN-FH insect medium complemented with 10% fetal calf serum, and the baculovirus DNA, BaculoGold™, was obtained from Pharmingen (San Diego, Calif.). Ex-Cell 400™ medium with L-Glutamine was purchased from JRH Scientific. Polypropylene 96-well microtiter plates were from Co-star (Cambridge, Mass.). All radioligands were from New England Nuclear (Boston, Mass.). Commercially available NPY and related peptide analogs were either from Bachem California (Torrance, Calif.) or Peninsula (Belmont, Calif.); [D-Trp$^{32}$]NPY and PP C-terminal fragments were synthesized by custom order from Chiron Mimotopes Peptide Systems (San Diego, Calif.). Bio-Rad Reagent was from Bio-Rad (Hercules, Calif.). Bovine serum albumin (ultra-fat free, A-7511) was from Sigma (St. Louis. Mo.). All other materials were reagent grade.

EXPERIMENTAL RESULTS cDNA Cloning

Figure 1:
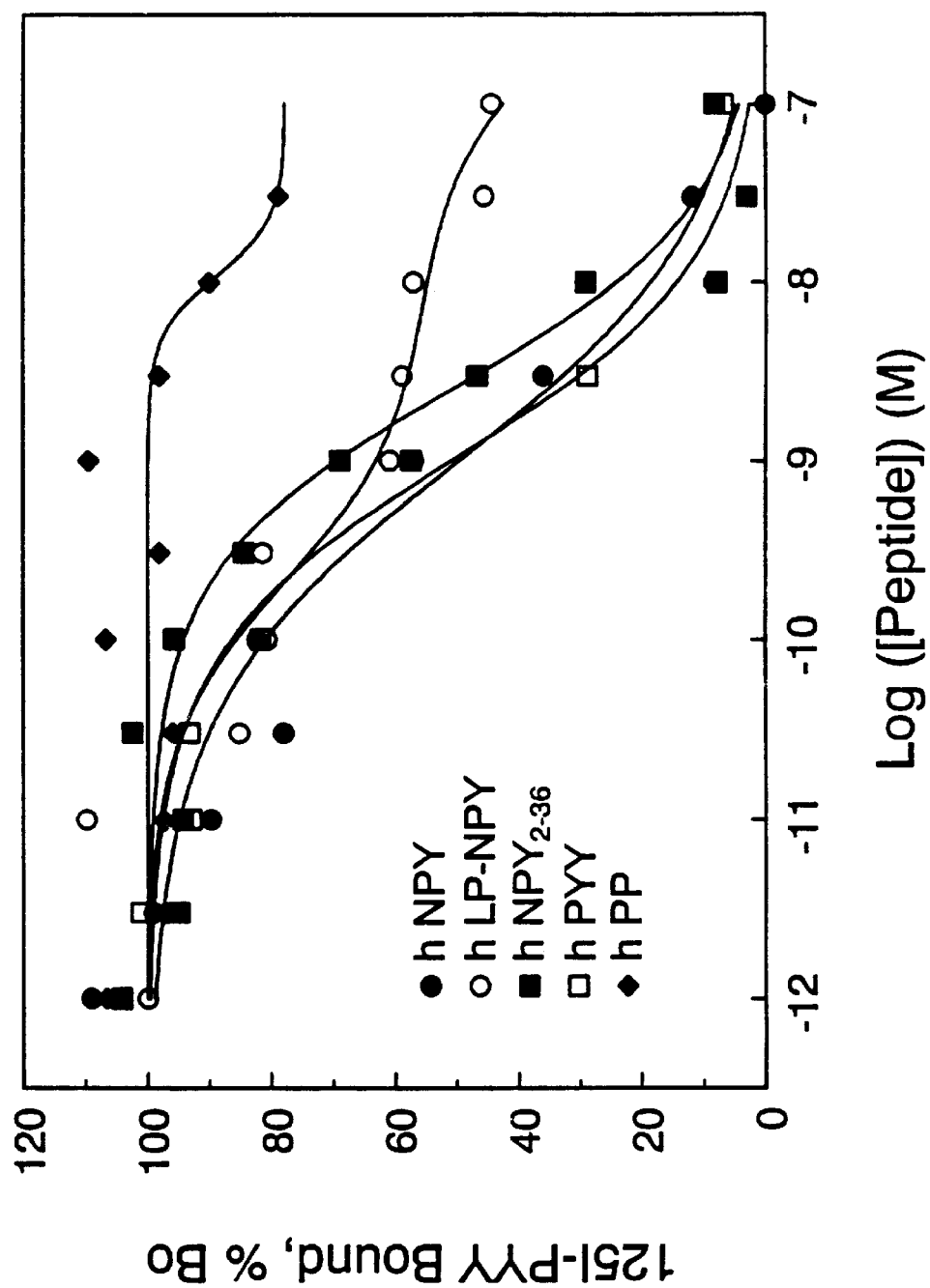
FIG. 1 Competitive displacement of $^{125}$I-PYY on membranes from rat hypothalamus. Membranes were incubated with $^{125}$I-PYY and increasing concentrations of peptide competitors. IC$_{50}$ values corresponding to 50% displacement were determined by nonlinear regression analysis. Data are representative of at least two independent experiments. IC$_{50}$ values for these compounds are listed separately in Table 2.
Figure 2:
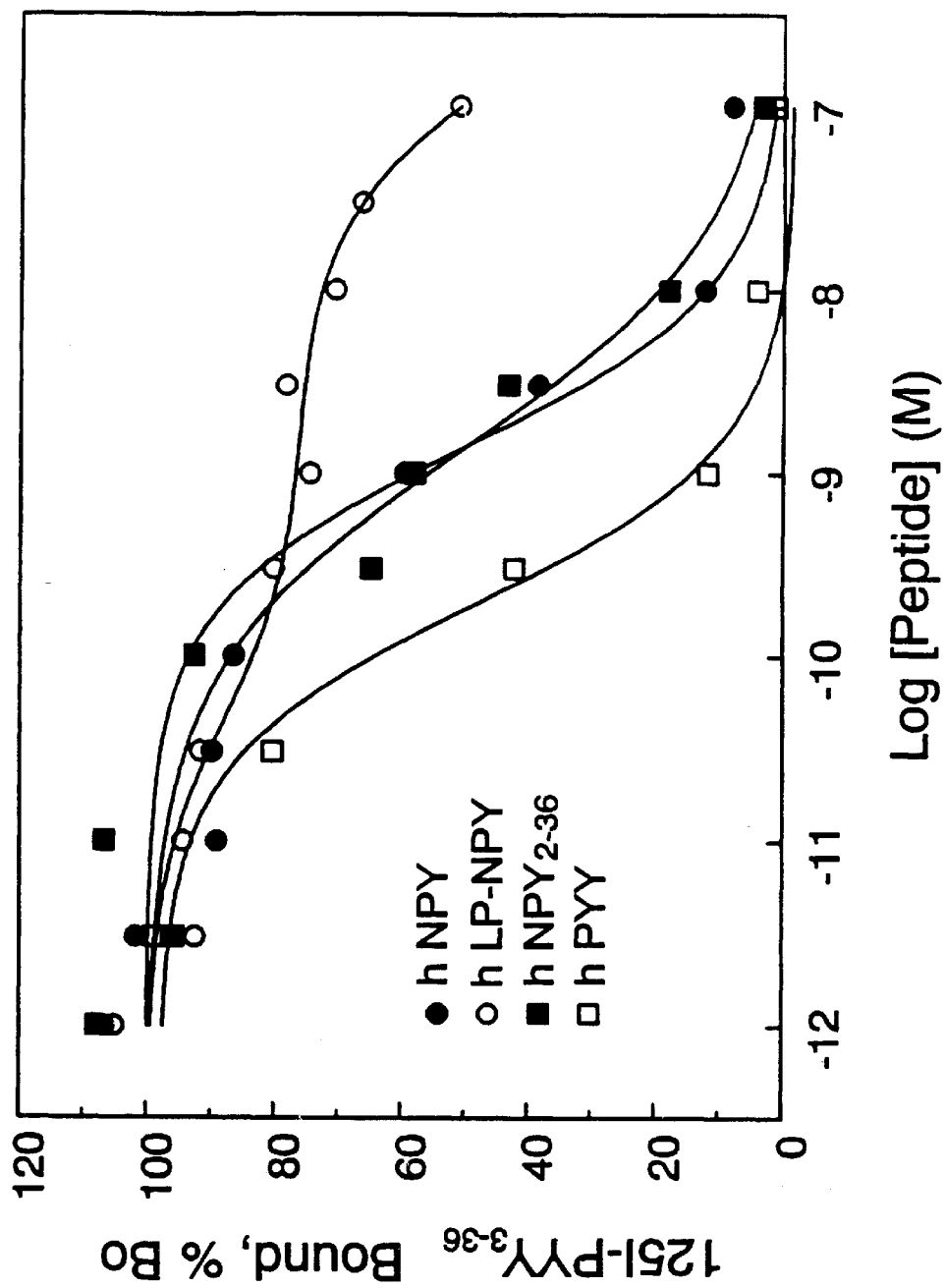
FIG. 2 Competitive displacement of $^{125}$I-PYY$_{3-36}$ on membranes from rat hypothalamus. Membranes were incubated with $^{125}$I-PYY$_{3-36}$ and increasing concentrations of peptide competitors. IC$_{50}$ values corresponding to 50% displacement were determined by nonlinear regression analysis. Data are representative of at least two independent experiments. IC$_{50}$ values for these compounds are listed separately in Table 2.

In order to clone a rat hypothalamic "atypical" NPY receptor subtype, applicants used an expression cloning strategy in COS-7 cells (Gearing et al, 1989; Kluxen et al, 1992; Kiefer et al, 1992). This strategy was chosen for its extreme sensitivity since it allows detection of a single "receptor positive" cell by direct microscopic autoradiography. Since the "atypical" receptor has only been described in feeding behavior studies involving injection of NPY and NPY related ligands in rat hypothalamus (see introduction), applicants first examined its binding profile by running competitive displacement studies of $^{125}$I-PYY and $^{125}$I-PYY$_{3-36}$ on membranes prepared from rat hypothalamus. The competitive displacement data indicate: 1) Human PP is able to displace 20% of the bound $^{125}$I-PYY with an IC$_{50}$ of 11 nM (FIG. 1 and Table 3). As can be seen in Table 5, this value does not fit with the isolated rat Y1, Y2 and Y4 clones and could therefore correspond to another NPY/PYY receptor subtype. 2) [Leu$_{31}$, Pro$_{34}$] NPY (a Y1 specific ligand) is able to displace with high affinity (IC$_{50}$ of 0.38) 27% of the bound $^{125}$I-PYY$_{3-36}$ ligand (a Y2 specific ligand) (FIG. 2 and Table 3). These data provide the first evidence based on a binding assay that rat hypothalamic membranes could carry an NPY receptor subtype with a mixed Y1/Y2 pharmacology (referred to as the "atypical" subtype) which fits with the pharmacology defined in feeding behavior studies.

TABLE 3: Pharmacological profile of the rat hypothalamus.

Binding data reflect competitive displacement of $^{125}$I-PYY and $^{125}$I-PYY$_{3-36}$ from rat hypothalamic membranes. Peptides were tested at concentrations ranging from 0.001 nM to 100 nM unless noted. The IC$_{50}$ value corresponding to 50% displacement, and the percentage of displacement relative to that produced by 300 nM human NPY, were determined by nonlinear regression analysis. Data shown are representative of at least two independent experiments.

TABLE 3

| Peptide | IC$_{50}$ Values, nM (% NPY-produced displacement) | |
| --- | --- | --- |
| | $^{125}$I-PYY | $^{125}$I-PYY$_{3-36}$ |
| human NPY | 0.82 (100%) | 1.5 (100%) |
| human NPY2–36 | 2.3 (100%) | 1.2 (100%) |
| human [Leu$^{31}$, Pro$^{34}$] NPY | 0.21 (44%) 340 (56%) | 0.38 (27%) 250 (73%) |
| human PYY | 1.3 (100%) | 0.29 (100%) |
| human PP | 11 (20%) | untested |

Based on the above data, a rat hypothalamic cDNA library of 3×10$^6$ independent recombinants with a 2.7 kb average insert size was fractionated into 450 pools of ≈7500 independent clones. All pools were tested in a binding assay with $^{125}$I-PYY as previously described (U.S. Ser. No. 08/192, 288). Seven pools gave rise to positive cells in the screening assay (#'s 81, 92, 147, 246, 254, 290, 312). Since Y1, Y2, Y4 and Y5 receptor subtypes (by PCR or binding analysis) are expressed in rat hypothalamus, applicants analyzed the DNA of positive pools by PCR with rat Y1, Y2 and Y4 specific primers. Pools #147, 246, 254 and 312 turned out to contain cDNAs encoding a Y1 receptor; pool #290 turned out to contain cDNA encoding a Y2 receptor subtype; but pools #81 and 92 were negative by PCR analysis for Y1, Y2 and Y4 and therefore likely contained a cDNA encoding a new rat hypothalamic NPY receptor (Y5). Pools #81 and 92 later turned out to contain an identical NPY receptor cDNA. Pool 92 was subjected to sib selection as described (U.S. Ser. No. 08/192,288) until a single clone was isolated (designated CG-18).

The isolated clone carries a 2.8 kb cDNA. This cDNA contains an open reading frame between nucleotides 779 and 2146 that encodes a 456 amino acid protein. The long 5' untranslated region could be involved in the regulation of translation efficiency or mRNA stability. The flanking sequence around the putative initiation codon does not conform to the Kozak consensus sequence for optimal translation initiation (Kozak, 1989, 1991). The hydrophobicity plot displayed seven hydrophobic, putative membrane spanning regions which makes the rat hypothalamic Y5 receptor a member of the G-protein coupled superfamily. The nucleotide and deduced amino acid sequences are shown in FIGS. 3 and 4, respectively. Like most G-protein coupled receptors, the Y5 receptor contains consensus sequences for N-linked glycosylation, in the amino terminus (position 21 and 28) involved in the proper expression of membrane proteins (Kornfeld and Kornfeld, 1985). The Y5 receptor carries two highly conserved cysteine residues in the first two extracellular loops that are believed to form a disulfide bond stabilizing the functional protein structure (Probst et al, 1992). The Y5 receptor shows 9 potential phosphorylation sites for protein kinase C in positions 204, 217, 254, 273, 285, 301, 328, 336 and 409 and 2 cAMP- and cGMP-dependent protein kinase phosphorylation sites in positions 298 and 370. It should be noted that 8 of these 11 potential phosphorylation sites are located in the third intra-cellular loop, two in the second intra-cellular loop, and one in the carboxy terminus of the receptor and could therefore play a role in regulating functional characteristics of the Y5 receptor (Probst et al, 1992). In addition the rat Y5 receptor carries a leucine zipper motif in its first putative transmembrane domain (Landschulz et al, 1988). A tyrosine kinase phosphorylation site is found in the middle of the leucine zipper.

Localization studies (see below) show that the Y5 mRNA is present in several areas of the rat hippocampus. Assuming a comparable localization in human brain, applicants screened a human hippocampal cDNA library (as described in U.S. Ser. No. 08/192,288, now U.S. Pat. No. 5,595,549) with rat oligonucleotide primers which were shown to yield a DNA band of the expected size in a PCR reaction run on human hippocampal cDNA (C. Gerald, unpublished results). Using this PCR screening strategy (Gerald et al, 1994, submitted for publication), three positive pools were identified. One of these pools was analyzed further, and an isolated clone was purified by sib selection. The isolated clone (CG-19) turned out to contain a full length cDNA cloned in the correct orientation for functional expression (see below). The human Y5 nucleotide and deduced amino acid sequences are shown in FIGS. 5 and 6, respectively. When compared to the rat Y5 receptor the human sequence shows 84.1% nucleotide identity (FIG. 7A to 7E) and 87.2% amino acid identity (FIG. 7F and 7G). The rat protein sequence is one amino acid longer at the very end of both amino and carboxy tails of the receptor when compared to the rat. The human 5–6 loop is one amino acid longer than the rat and shows multiple non conservative substitutions. Even though the 5–6 loops show significant changes between the rat and human homologs, all of the protein motifs found in the rat receptor are present in the human homolog. All putative transmembrane domains and extra cellular loop regions are highly conserved (FIG. 7F and 7G). Therefore, both pharmacological profiles and functional characteristics of the rat and human Y5 receptor subtype homologs may be expected to match closely.

Figures 8A, 8B, 8C:
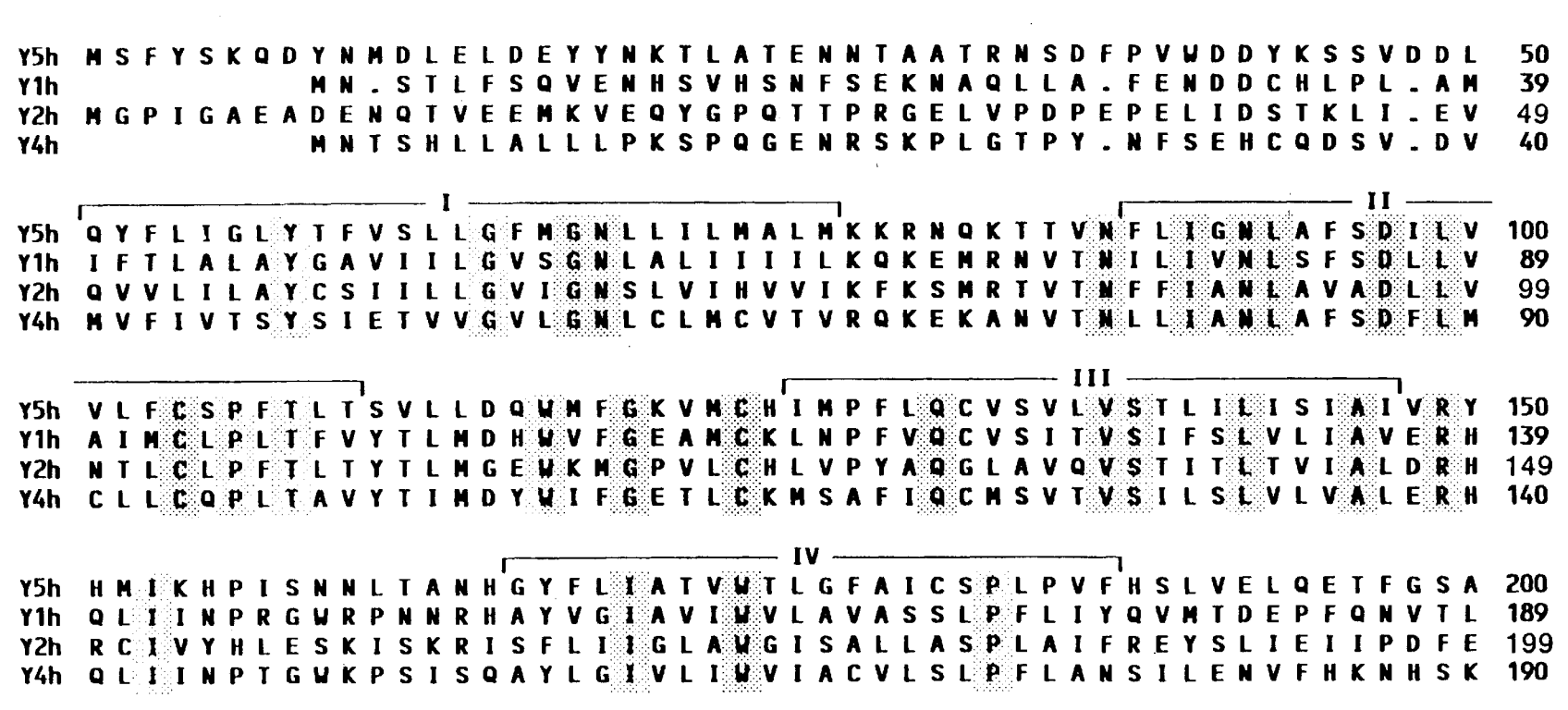

When the human and rat Y5 receptor sequences were compared to other NPY receptor subtypes or to other human G protein-coupled receptor subtypes, both overall and transmembrane domain identities were very low, showing that the Y5 receptor genes are not closely related to any other previously characterized cDNAs (Table 4). Even among the human NPY receptor family, Y1, Y2, Y4 and Y5 members show unusually low levels of amino acid identity (FIGS. 8A through 8C).

TABLE 4

Human Y5 transmembrane domains identity with other human NPY receptor subtypes and other human G-protein coupled receptors

| Receptor subtype | % TM identity |
| --- | --- |
| Y-4 | 40 |
| Y-2 | 42 |
| Y-1 | 42 |
| MUSGIR | 32 |
| DroNPY | 31 |
| Beta-1 | 30 |
| Endothelin-1 | 30 |
| Dopamine D2 | 29 |
| Adenosine A2b | 28 |
| Subst K | 28 |
| Alpha-2A | 27 |
| 5-HT1Dalpha | 26 |
| Alpha-1A | 26 |
| IL-8 | 26 |
| 5-HT2 | 25 |
| Subst P | 24 |

Northern blot analysis

Using the rat Y5 probe, northern hybridizations reveal a strong signal at 2.7 kb and a weak band at 8 kb in rat whole brain. A weak signal is observed at 2.7 kb in testis. No signal was seen in heart, spleen, lung, liver, skeletal muscle and kidney after a three day exposure (FIG. 16A). This is in good agreement with the 2.7 kb cDNA that we isolated by expression cloning from rat hypothalamus and indicates that our cDNA clone is full length. The 8 kb band seen in whole brain probably corresponds to unspliced pre-mRNA.

With the human Y5 probe, northern hybridizations (FIGS. 16B and 16C) showed a strong signal at 3.5 kb with a much weaker band at 2.2 and 1.1 kb in caudate nucleus, putamen and cerebral cortex, a medium signal in frontal lobe and amygdala and a weak signal in hippocampus, occipital and temporal lobes, spinal cord, medulla, thalamus, subthalamic nucleus, and substantia nigra. No signal at 3.5 kb was detectable in cerebellum or corpus callosum after a 48 h exposure. It should be noted that Clontech's MTN II and III blots do not carry any mRNA from hypothalamus, periaquiductalgray, superior colliculus and raphe.

Southern blot analysis on human genomic DNA reveals a unique band pattern in 4 of the 5 restriction digests (FIG. 17A). The two bands observed in the PstI digest can be explained by the presence of a PstI site in the coding region of the human Y5 gene. Rat southern blotting analysis showed a unique band pattern in all five restriction digests tested (FIG. 17B). These analyses are consistent with the human and rat genomes containing a single copy of the Y5 receptor gene.

Canine Y5 homolog

The canine nucleotide sequence obtained to date (PCR and 3' RACE products) spans the canine Y5 receptor from the first extracellular loop immediately upstream of TM III into the 3' untranslated region (FIG. 14). In the coding region, this nucleotide sequence is highly identical to both the human and the rat sequences (91% and 83.3% respectively). The deduced canine Y5 amino acid sequence is shown in FIG. 15. This amino acid sequence is again highly identical to both the human and rat Y5 sequences (94.6% and 89.5% respectively), with most amino acid changes located in the 5–6 loop. Therefore the pharmacological profile of the canine Y5 receptor subtype is expected to closely resemble the human and rat Y5 profiles.

Binding Studies

Figure 9:
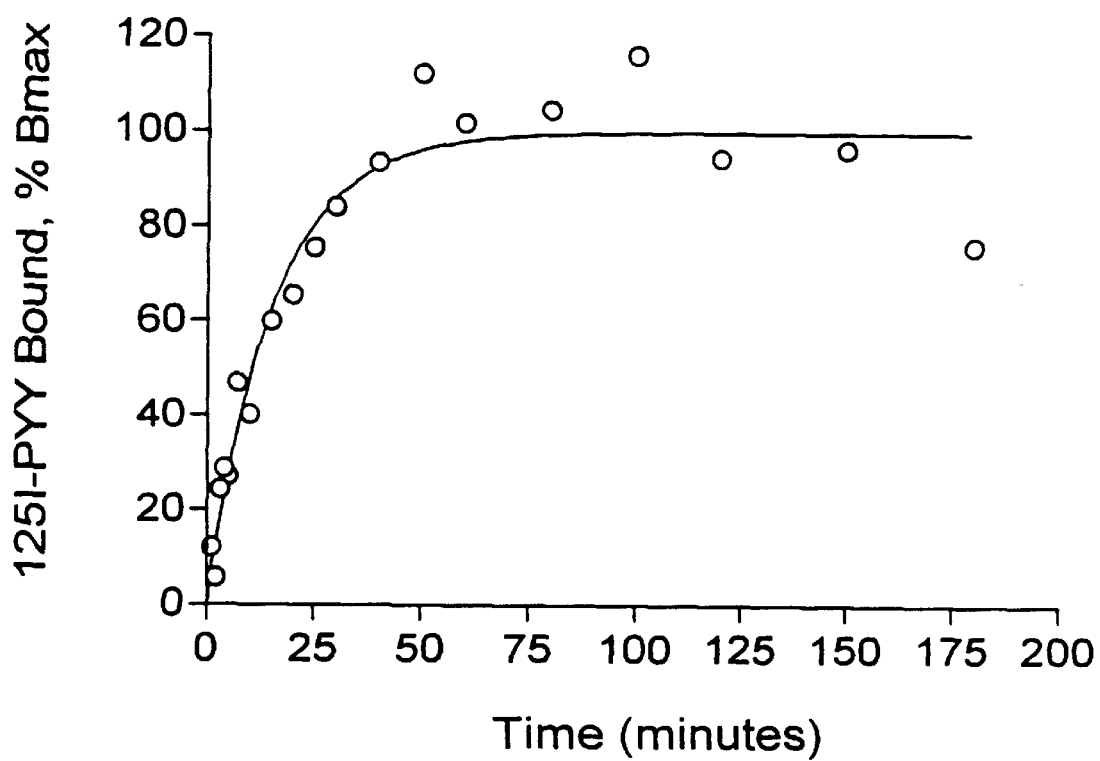
FIG. 9 Equilibrium binding of $^{125}$I-PYY to membranes from COS-7 cells transiently expressing rat Y5 receptors. Membranes were incubated with $^{125}$I-PYY for the times indicated, in the presence or absence of 300 nM human NPY. Specific binding, B, was plotted against time, t, to obtain the maximum number of equilibrium binding sites, B$_{max}$, and observed association rate, K$_{obs}$, according to the equation, B=B$_{max}$* (1-e$^{-(kobs * t)}$). Binding is shown as the percentage of total equilibrium binding, B$_{max}$, determined by nonlinear regression analysis. Each point represents a triplicate determination.
Figure 10:
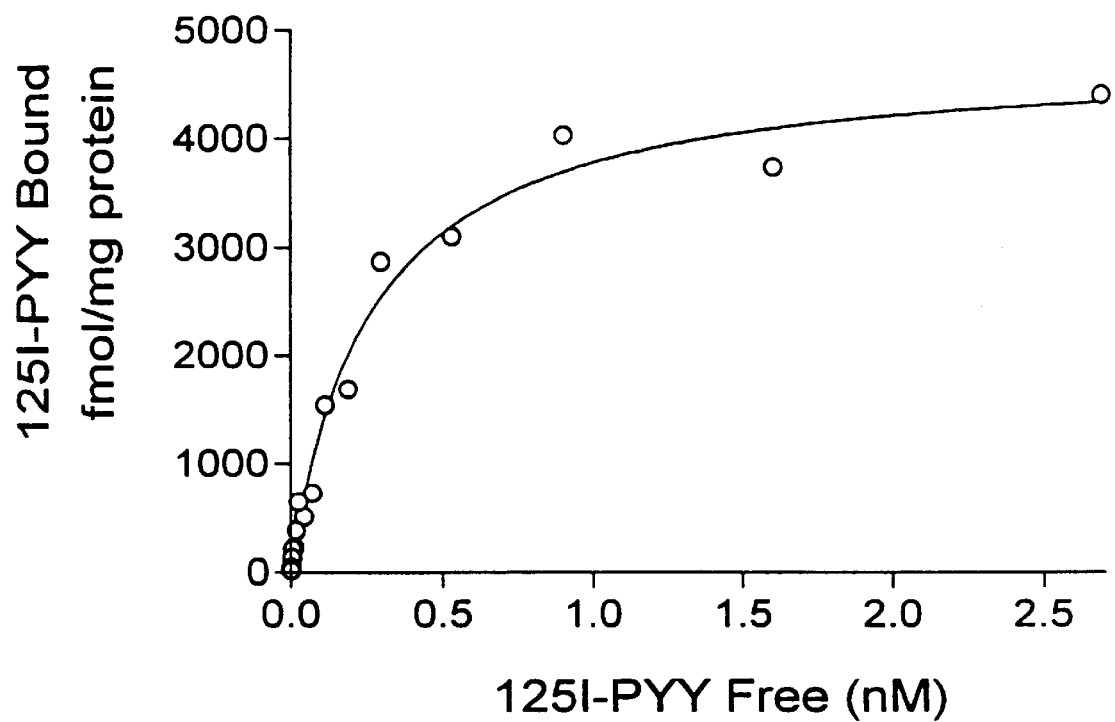
FIG. 10 Saturable equilibrium binding of $^{125}$I-PYY to membranes from COS-7 cells transiently expressing rat Y5 receptors. Membranes were incubated with $^{125}$I-PYY ranging in concentration from 0.4 pM to 2.7 µM, in the presence or absence of 300 nM human NPY. Specific binding, B, was plotted against the free $^{125}$I-PYY concentration, [L], to obtain the maximum number of saturable binding sites, B$_{max}$, and the $^{125}$I-PYY equilibrium dissociation constant, K$_d$, according to the binding isotherm, B=B$_{max}$[L]/([L]+K$_d$). Specific binding is shown. Data are representative of three independent experiments, with each point measured in triplicate.

The cDNA for the rat hypothalamic Y5 receptor was transiently expressed in COS-7 cells for full pharmacological evaluation. $^{125}$I-PYY bound specifically to membranes from COS-7 cells transiently transfected with the rat Y5 receptor construct. The time course of specific binding was measured in the presence of 0.08 nM $^{125}$I-PYY at 30° C. (FIG. 9). The association curve was monophasic, with an observed association rate ($K_{obs}$) of 0.06 min$^{-1}$ and a $t_{1/2}$ of 11 min; equilibrium binding was 99% complete within 71 min and stable for at least 180 min. All subsequent binding assays were carried out for 120 min at 30° C. The binding of $^{125}$I-PYY to transiently expressed rat Y5 receptors was saturable over a radioligand concentration range of 0.4 pM to 2.7 nM. Binding data were fit to a one-site binding model with an apparent $K_d$ of 0.29 nM (p$K_d$=9.54±0.13, n=4). A receptor density of between 5 and 10 pmol/mg membrane protein was measured on membranes which had been frozen and stored in liquid nitrogen (FIG. 10). Membranes from mock-transfected cells, when prepared and analyzed in the same way as those from CG-18-transfected cells, displayed no specific binding of $^{125}$I-PYY (data not shown). Applicants conclude that the $^{125}$I-PYY binding sites observed under the described conditions were derived from the rat Y5 receptor construct.

A closely related peptide analog, porcine $^{125}$I-[Leu$^{31}$, Pro$^{34}$]PYY, also bound specifically to membranes from COS-7 cells transiently transfected with rat Y5 receptor cDNA. The time course of specific binding was measured at room temperature in both standard binding buffer ([Na$^+$]=10 mM) and isotonic binding buffer ([Na$^+$]=138 mM) using 0.08 nM nM $^{125}$I-[Leu$^{31}$,Pro$^{34}$]PYY nM (FIG. 18). The association curve in 10 mM [Na$^+$] was monophasic, with an observed association rate ($K_{obs}$) of 0.042 min$^{-1}$ and a $t_{1/2}$ of 17 min; equilibrium binding was 99% complete within 110 min and stable for at least 210 min (specific binding was maximal at 480 fmol/mg membrane protein). The association curve in 138 mM [Na$^+$] was also monophasic with a slightly slower time course: ($K_{obs}$) of 0.029 min$^{-1}$ and a $t_{1/2}$ of 24 min.; equilibrium binding was 99% complete within 160 min. and stable for at least 210 min. (specific binding was maximal at 330 fmol/mg membrane protein). Note that the specific binding was reduced as [Na$^+$] was increased; a similar phenomenon has been observed for other G protein coupled receptors and may reflect a general property of this receptor family to be modulated by Na$^+$ (Horstman et. al., 1990). Saturation binding studies were performed with $^{125}$I-[Leu$^{31}$,Pro$^{34}$]PYY in isotonic buffer at room temperature over a 120 minute period. Specific binding to transiently expressed rat Y5 receptors was saturable over a radioligand concentration range of 0.6 pM to 1.9 nM. Binding data were fit to a one-site binding model with an apparent $K_d$ of 0.072 nM (pKd=10.14+0.07, n=2). A receptor density of 560±150 pmol/mg on membranes which had been frozen and stored in liquid nitrogen. That $^{125}$I-[Leu$^{31}$,Pro$^{34}$]PYY can bind to the rat Y5 receptor with high affinity at room temperature in isotonic buffer makes it a potentially useful ligand for characterizing the native Y5 receptor in rat tissues using autoradiographic techniques. Care must be taken, however, to use appropriate masking agents to block potential radiolabeling of other receptors such as Y1 and Y4 receptors (note in Table 6 that rat Y1 and Y4 bind the structural homolog [Pro$^{34}$]PYY). Previously published reports of $^{125}$I-[Leu$^{31}$, Pro$^{34}$]PYY as a Y1-selective radioligand should be re-evaluated in light of new data obtained with the rat Y5 receptor (Dumont et al., 1995).

Figure 11:
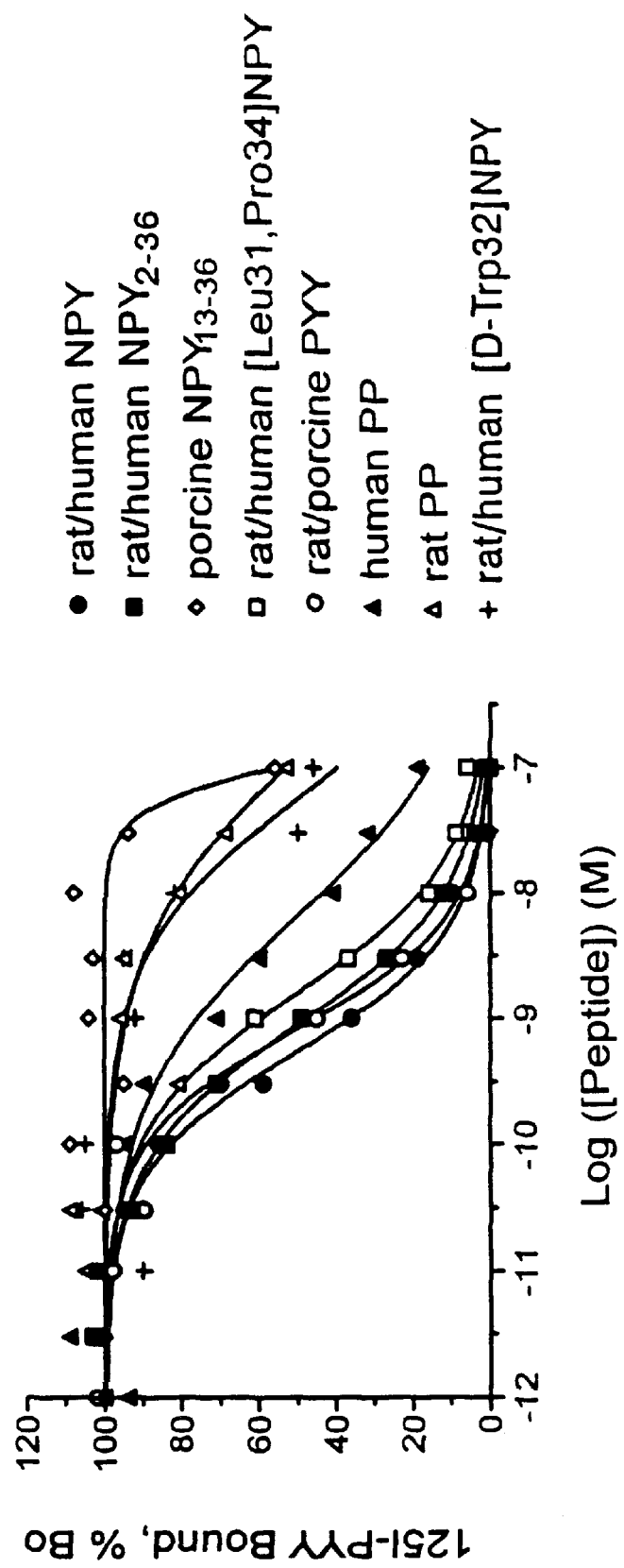
FIG. 11 Competitive displacement of $^{125}$I-PYY from COS-7 cells transiently expressing rat Y5 receptors. Membranes were incubated with $^{125}$I-PYY and increasing concentrations of peptide competitors. IC$_{50}$ values corresponding to 50% displacement were determined by nonlinear regression analysis and converted to K$_i$ values according to the equation, K$_i$=IC$_{50}$/(1+[L]/K$_d$), where [L] is the $^{125}$I-PYY concentration and K$_d$ is the equilibrium dissociation constant of $^{125}$I-PYY. Data are representative of at least two independent experiments. Rank orders of affinity for these and other compounds are listed separately in Table 4.

The pharmacological profile of the rat Y5 receptor was first studied by using pancreatic polypeptide analogs in membrane binding assays. The rank order of affinity for selected compounds was derived from competitive displacement of $^{125}$I-PYY (FIG. 11). The rat Y5 receptor was compared with cloned Y1, Y2, and Y4 receptors from human (Table 5) and rat (Table 6), all expressed transiently in COS-7 cells. One receptor subtype absent from our panel was the Y3, human or rat, as no model suitable for radioligand screening has yet been identified.

TABLE 5: Pharmacological profile of the rat Y5 receptor vs. Y-type receptors cloned from human.

Binding data reflect competitive displacement of $^{125}$I-PYY from membranes of COS-7 cells transiently expressing rat Y5 and human subtype clones. Peptides were tested at concentrations ranging from 0.001 nM to 1000 nM unless noted. IC$_{50}$ values corresponding to 50% displacement were determined by nonlinear regression analysis and converted to $K_i$ values according to the Cheng-Prusoff equation. The data shown are representative of at least two independent experiments.

TABLE 5

| | $K_i$ Values (nM) | | | |
|---|---|---|---|---|
| Peptide | Rat Y5 | Human Y4 | Human Y1 | Human Y2 |
| rat/human NPY | 0.68 | 2.2 | 0.07 | 0.74 |
| porcine NPY | 0.66 | 1.1 | 0.05 | 0.81 |
| human NPY$_{2-36}$ | 0.86 | 16 | 3.9 | 2.0 |
| porcine NPY$_{2-36}$ | 1.2 | 5.6 | 2.4 | 1.2 |
| porcine NPY$_{13-36}$ | 73 | 38 | 60 | 2.5 |
| porcine NPY$_{26-36}$ | >1000 | 304 | >1000 | 380 |
| porcine C2-NPY | 470 | 120 | 79 | 3.5 |
| human [Leu$^{31}$, Pro$^{34}$] NPY | 1.0 | 1.1 | 0.17 | >130 |
| human [D-Trp$^{32}$] NPY | 53 | >760 | >1000 | >1000 |
| human NPY free acid | 480 | >1000 | 490 | >1000 |
| rat/porcine PYY | 0.64 | 0.14 | 0.35 | 1.26 |
| human PYY | 0.87 | 0.87 | 0.18 | 0.36 |
| human PYY$_{3-36}$ | 8.4 | 15 | 41 | 0.70 |
| human PYY$_{13-36}$ | 190 | 46 | 33 | 1.5 |
| human [Pro$^{34}$] PYY | 0.52 | 0.12 | 0.14 | >310 |
| human PP | 5.0 | 0.06 | 77 | >1000 |
| human PP$_{2-36}$* | not tested | 0.06 | >40 | >100 |
| human PP$_{13-36}$* | not tested | 39 | >100 | >100 |
| rat PP | 180 | 0.16 | 450 | >1000 |
| salmon PP | 0.31 | 3.2 | 0.11 | 0.17 |

*Tested only up to 100 nM.

TABLE 6: Pharmacological profile of the rat Y5 receptor vs. Y-type receptors cloned from rat.

Binding data reflect competitive displacement of $^{125}$I-PYY from membranes of COS-7 cells transiently expressing rat Y5 and rat subtype clones. Peptides were tested at concentrations ranging from 0.001 nM to 1000 nM. $IC_{50}$ values corresponding to 50% displacement were determined by nonlinear regression analysis and converted to $K_i$ values according to the Cheng-Prusoff equation. The data shown are representative of at least two independent experiments. Exception: new peptides (marked with a double asterisk) were tested in one or more independent experiments.

TABLE 6

| Peptide | $K_i$ Values (nM) | | | |
|---|---|---|---|---|
| | Rat Y5 | Rat Y4 | Rat Y1 | Rat Y2 |
| rat/human NPY | 0.68 | 1.7 | 0.12 | 1.3 |
| porcine NPY ** | 0.66 | 1.78 | 0.06 | 1.74 |
| frog NPY ** (melanostatin) | 0.71 | | 0.09 | 0.65 |
| human $NPY_{2-36}$ | 0.86 | 5.0 | 12 | 2.6 |
| porcine $NPY_{2-36}$ ** | 1.1 | 18 | 1.6 | 1.6 |
| porcine $NPY_{3-36}$ | 7.7 | 36 | 91 | 3.7 |
| porcine $NPY_{13-36}$ | 73 | 140 | 190 | 31 |
| porcine $NPY_{16-36}$ ** | 260 | 200 | 140 | 35 |
| porcine $NPY_{18-36}$ ** | >1000 | | 470 | 12 |
| porcine $NPY_{20-36}$ ** | >100 | | 360 | 93 |
| porcine $NPY_{22-36}$ ** | >1000 | >1000 | 54 | |
| porcine $NPY_{26-36}$ ** | >1000 | >1000 | >830 | |
| human [$Leu^{31}$, $Pro^{34}$] NPY | 1.0 | 0.59 | 0.10 | >1000 |
| porcine ** [$Leu^{31}$, $Pro^{34}$] NPY | 1.6 | 0.32 | 0.25 | 840 |
| human (O-Methyl-$Tyr^{21}$) NPY ** | 1.6 | | | 2.3 |
| human NPY free acid ** | >610 | >1000 | 720 | >980 |
| porcine C2-NPY ** | >260 | 22 | 140 | 2.6 |
| human $NPY_{1-24}$ amide ** | >1000 | | >320 | >1000 |
| human [D-$Trp^{32}$] NPY | 35 | >630 | >1000 | 760 |
| rat/porcine PYY | 0.64 | 0.58 | 0.21 | 0.28 |
| human PYY ** | 0.87 | | 0.12 | 0.30 |
| human $PYY_{3-36}$ ** | 8.4 | 15 | | 0.48 |
| human $PYY_{13-36}$ ** | 290 | | 130 | 14 |
| human [$Pro^{34}$] PYY | 0.52 | 0.19 | 0.25 | >1000 |
| porcine [$Pro^{34}$] PYY ** | 0.64 | 0.24 | 0.07 | >980 |
| avian PP ** | >930 | >81 | >320 | >1000 |
| human PP | 5.0 | 0.04 | 43 | >1000 |
| human $PP_{13-36}$ ** | 84 | | >1000 | >650 |
| human $PP_{31-36}$ ** | >1000 | 26 | >10 000 | >10 000 |
| human $PP_{31-36}$ free acid ** | >10,000 | >100 | | |
| bovine PP ** | 8.4 | 0.19 | 120 | >1000 |
| frog PP (rana temporaria) ** | >550 | >1000 | 720 | >980 |
| rat PP | 230 | 0.19 | 350 | >1000 |
| salmon PP | 0.33 | 3.0 | 0.30 | 0.16 |
| PYX-1 ** | 920 | | | |
| PYX-2 ** | >1000 | | | |
| FLRF-amide ** | 5500 | | 45000 | |
| FMRF-amide ** | 18000 | | | |
| W(nor-L) RF-amide ** | 8700 | | | |

The rat Y5 receptor possessed a unique pharmacological profile when compared with human and rat Y-type receptors. It displayed a preference for structural analogs of rat/human NPY ($K_i$=0.68 nM) and rat/porcine PYY ($K_i$=0.64 nM) over most PP derivatives. The high affinity for salmon PP ($K_i$=0.31 nM) reflects the close similarity between salmon PP and rat NPY, sharing 81% of their amino acid sequence and maintaining identity at key positions: $Tyr^1$, $Gln^{34}$, and $Tyr^3$. Both N- and C-terminal peptide domains are apparently important for receptor recognition. The N-terminal tyrosine of NPY or PYY could be deleted without an appreciable loss in binding affinity ($K_i$=0.86 nM for rat/human $NPY_{2-36}$), but further N-terminal deletion was disruptive ($K_i$=73 nM for porcine $NPY_{13-36}$). This pattern places the binding profile of the Y5 receptor somewhere between that of the Y2 receptor (which receptor can withstand extreme N-terminal deletion) and that of the Y1 receptor (which receptor is sensitive to even a single-residue N-terminal deletion). Note that the human Y4 receptor can be described similarly ($K_i$=0.06 nM for human PP, 0.06 nM for human $PP_{2-36}$, and 39 nM for human $PP_{13-36}$). The Y5 receptor resembled both Y1 and Y4 receptors in its tolerance for ligands containing $Pro^{34}$ (as in human [$Leu^{31}$,$Pro^{34}$]NPY, human [$Pro^{34}$]-PYY, and human PP). Interestingly, the rat Y5 receptor displayed a preference for human PP ($K_i$=5.0 nM) over rat PP ($K_i$=180 nM). This pattern distinguishes the rat Y5 from the rat Y4 receptor, which binds both human and rat PP with $K_i$ values <0.2 nM. Hydrolysis of the carboxy terminal amide to free carboxylic acid, as in NPY free acid, was disruptive for binding affinity for the rat Y5 receptor ($K_i$=480 nM). The terminal amide appears to be a common structural requirement for pancreatic polypeptide family/receptor interactions.

Several peptides shown previously to stimulate feeding behavior in rats bound to the rat Y5 receptor with $K_i \leq 5.0$ nM. These include rat/human NPY ($K_i$=0.68 nM), rat/porcine PYY ($K_i$=0.64 nM), rat/human $NPY_{2-36}$ ($K_i$=0.86 nM), rat/human [$Leu^{31}$,$Pro^{34}$]NPY ($K_i$=1.0 nM), and human PP ($K_i$=5.0 nM). Conversely, peptides which were relatively less effective as orexigenic agents bound weakly to CG-18. These include porcine $NPY_{13-36}$ ($K_i$=73 nM), porcine C2-NPY ($K_i$=470 nM) and human NPY free acid ($K_i$=480 nM). The rank order of $K_i$ values are in agreement with rank orders of potency and activity for stimulation of feeding behavior when peptides are injected i.c.v. or directly into rat hypothalamus (Clark et al., 1984; Stanley et al., 1985; Kalra et al., 1991; Stanley et al., 1992). The rat Y5 receptor also displayed moderate binding affinity for [D-$Trp^{32}$]NPY ($K_i$=53 nM), the modified peptide reported to regulate NPY-induced feeding by Balasubramaniam et al. (1994). It is noteworthy that [D-$Trp^{32}$]NPY was $\geq$10-fold selective for CG-18 over the other cloned receptors studied, whether human or rat. These data clearly and definitively link the cloned Y5 receptor to the feeding response.

The cDNA corresponding to the human Y5 homolog isolated from human hippocampus was transiently expressed in COS-7 cells for membrane binding studies. The binding of $^{125}$I-PYY to the human Y5 receptor (CG-19) was saturable over a radioligand concentration range of 8 pM to 1.8 nM. Binding data were fit to a one-site binding model with an apparent $K_d$ of 0.10 nM in the first experiment. Repeated testing yielded an apparent $K_d$ of 0.18 nM ($pK_d$=9.76±0.11, n=4). A maximum receptor density of 500 fmol/mg membrane protein was measured on fresh membranes. As determined by using peptide analogs within the pancreatic polypeptide family, the human Y5 pharmacological profile bears a striking resemblance to the rat Y5 receptor (Tables 7 and 8).

TABLE 7: Pharmacological profile of the rat Y5 receptor vs. the human Y5 receptor, as expressed both transiently in COS-7 and stably in LM(tk–) cells.

Binding data reflect competitive displacement of radioligand (either $^{125}$I-PYY or $^{125}$I-PYY$_{3-36}$ as indicated) from membranes of COS-7 cells transiently expressing the rat Y5 receptor and its human homolog or from LM(tk–) cells stably expressing the human Y5 receptor. Peptides were tested at concentrations ranging from 0.001 nM to 1000 nM. IC$_{50}$ values corresponding to 50% displacement were determined by nonlinear regression analysis and converted to K$_i$ values according to the Cheng-Prusoff equation. New peptides are marked with a double asterisk.

TABLE 7

| | K$_i$ Values (nM) | | | |
|---|---|---|---|---|
| Peptide | Rat Y5 (COS-7, $^{125}$I-PYY) | Human Y5 (COS-7, $^{125}$I-PYY) | Human Y5 (LM(tk-), $^{125}$I-PYY) | Human Y5 (LM(tk-), $^{125}$I-PYY$_{3-36}$) |
| rat/human NPY | 0.68 | 0.15 | 0.89 | 0.65 |
| porcine NPY ** | | 0.68 | 1.4 | |
| human NPY$_{2-36}$ | 0.86 | 0.33 | 1.6 | 0.51 |
| porcine NPY$_{2-36}$ ** | 0.66 | 0.58 | 1.2 | |
| porcine NPY$_{13-36}$ | 73 | 110 | | 39 |
| porcine NPY$_{16-36}$ ** | 260 | 300 | | 180 |
| porcine NPY$_{18-36}$ ** | >1000 | >470 | | 310 |
| porcine NPY$_{22-36}$ ** | >1000 | >1000 | | |
| porcine NPY$_{26-36}$ ** | >1000 | >1000 | | |
| human [Leu$^{31}$, Pro$^{34}$] NPY | 1.0 | 0.72 | 3.0 | |
| human [Leu$^{31}$, Pro$^{34}$] NPY ** | | | 2.4 | 1.4 |
| human NPY free acid ** | >610 | >840 | | |
| porcine C2-NPY ** | 260 | 370 | 260 | 220 |
| human [D-Trp$^{32}$] NPY | 35 | 35 | 16 | 10 |
| rat/porcine PYY | 0.64 | 0.75 | | |
| human PYY ** | 0.87 | 0.44 | 1.3 | 0.43 |
| human PYY$_{3-36}$ ** | 8.4 | 17 | 8.1 | 1.6 |
| human [Pro$^{34}$] PYY | 0.52 | 0.34 | 1.7 | 1.7 |
| human PP | 5.0 | 1.7 | 3.0 | 1.2 |
| human PP$_{2-36}$ ** | | 2.1 | | |
| human PP$_{13-36}$ ** | 290 | 720 | | |
| human PP 31-36 ** | >10 000 | >10 000 | | 41 000 |
| human [Ile$^{31}$, Gln$^{34}$] PP ** | | 2.0 | | |
| bovine PP ** | 8.4 | 1.6 | 7.9 | 5.0 |
| rat PP | 230 | 630 | | 130 |
| salmon PP | 0.33 | 0.27 | | 0.63 |

TABLE 8: Pharmacological profile of the human Y5 receptor vs. Y-type receptors cloned from human.

Binding data reflect competitive displacement of $^{125}$I-PYY from membranes of COS-7 cells transiently expressing human Y5 other sub-type clones. Peptides were tested at concentrations ranging from 0.001 nM to 1000 nM unless noted. IC$_{50}$ values corresponding to 50% displacement were determined by nonlinear regression analysis and converted to K$_i$ values according to the Cheng-Prusoff equation. The data shown are representative of at least two independent experiments.

TABLE 8

| | K$_i$ Values (nM) | | | |
|---|---|---|---|---|
| Peptide | Human Y5 | Human Y4 | Human Y1 | Human Y2 |
| rat/human NPY | 0.46 | 2.2 | 0.07 | 0.74 |
| porcine NPY | 0.68 | 1.1 | 0.05 | 0.81 |
| human NPY$_{2-36}$ | 0.75 | 16 | 3.9 | 2.0 |
| porcine NPY$_{2-36}$ | 0.58 | 5.6 | 2.4 | 1.2 |
| porcine NPY$_{13-36}$ | 110 | 38 | 60 | |
| porcine NPY$_{26-36}$ | >1000 | 304 | >1000 | 380 |
| porcine C2-NPY | 370 | 120 | 79 | 3.5 |
| human [Leu$^{31}$, Pro$^{34}$] NPY | 1.6 | 1.1 | 0.17 | >130 |
| human [D-Trp$^{32}$] NPY | 35 | >760 | >1000 | >1000 |
| human NPY free acid | >840 | >1000 | 490 | >1000 |
| rat/porcine PYY | 0.58 | 0.14 | 0.35 | 1.26 |
| human PYY | 0.44 | 0.87 | 0.18 | 0.36 |
| human PYY$_{3-36}$ | 17 | 15 | 41 | 0.70 |
| human PYY$_{13-36}$ | not tested | 46 | 33 | 1.5 |
| human [Pro$^{34}$] PYY | 0.77 | 0.12 | 0.14 | >310 |
| human PP | 1.4 | 0.06 | 77 | >1000 |
| human PP$_{2-36}$* | 2.1 | 0.06 | >40 | >100 |
| human PP$_{13-36}$* | 720 | 39 | >100 | >100 |
| rat PP | 630 | 0.16 | 450 | >1000 |
| salmon PP | 0.46 | 3.2 | 0.11 | 0.17 |

*Tested only up to 100 nM.

Binding Studies of hY5 Expressed in Insect Cells

Tests were initially performed to optimize expression of hY5 receptor. Infecting Sf9, Sf21, and High Five cells with hY5BB3 virus at a multiplicity of infection (MOI) of 5 and preparing membranes for binding analyses at 45 hrs. postinfection, we observed B$_{max}$ ranges from 417 to 820 fmoles/mg protein, with the highest expression being hY5BB3 in Sf21 cells. Therefore, our next series of experiments used Sf21 cells. We next examined optimal multiplicity of infection (the ratio of viral particles to cells) by testing MOI of 1, 2, 5 and 10. The B$_{max}$ values were ≈1.1–1.2 pmoles/mg protein for any of the MOIs, suggesting that increasing the number of viral particles per cell is neither deleterious nor advantageous. Since viral titer calculations are approximate, we used MOI=5 for future experiments. The last parameter we tested was hours postinfection for protein expression, ranging from 45–96 hours postinfection. We found that optimal expression occurred 45–73 hrs. postinfection. In summary, we have created a hY5 recombinant baculovirus which binds $^{125}$I-PYY with a B$_{max}$ of ≈1.2 pmoles/mg protein.

Human Y5 Homolog: Transient Expression in Baculovirus-Infected Sf21 Insect Ovary Cells Sf21 cells infected with a human Y5 baculovirus construct were harvested as membrane homogenates and screened for specific binding of $^{125}$I-PYY using 0.08 nM radioligand. Specific binding was greatest (500 fmol/mg membrane protein) for sample D-2/[4], derived from Sf-21 cells. No specific binding was observed after infection with the baculovirus plasmid alone (data not shown). If we make the assumption that the binding affinity of porcine $^{125}$I-PYY for the human Y5 receptor is the same whether the expression system is COS-7 or baculovirus/Sf-21 (0.18 nM), the specific binding in sample D-2/[4] predicts an apparent $B_{max}$ of 1600 fmol/mg membrane protein. The Y5 receptor yield in the baculovirus/Sf21 expression system is therefore as good or better than that in COS-7. We conclude that the baculovirus offers an alternative transfection technique amenable to large batch production of the human Y5 receptor.

Stable Expression Systems for Y5 Receptors: Characterization in Binding Assays

The cDNA for the rat Y5 receptor was stably transfected into 293 cells which were pre-screened for the absence of specific $^{125}$I-PYY binding (data not shown). After co-transfection with the rat Y5 cDNA plus a G-418-resistance gene and selection with G-418, surviving colonies were screened as membrane homogenates for specific binding of $^{125}$I-PYY using 0.08 nM radioligand. A selected clone (293 clone #12) bound 65 fmol $^{125}$I-PYY /mg membrane protein and was isolated for further study in functional assays.

The cDNA for the human Y5 receptor was stably transfected into both NIH-3T3 and LM(tk-) cells, each of which were pre-screened for the absence of specific $^{125}$I-PYY binding (data not shown). After co-transfection with the human Y5 cDNA plus a G-418-resistance gene and selection with G-418, surviving colonies were screened as membrane homogenates for specific binding of $^{125}$I-PYY using 0.08 nM radioligand. NIH-3T3 clone #8 bound 46 fmol $^{125}$I-PYY/mg membrane protein and LM(tk-) clone #7 bound 32 fmol $^{125}$I-PYY/mg membrane protein. These two clones were isolated for further characterization in binding and cAMP functional assays. A third clone which bound 25 fmol/mg membrane protein, LM(tk-) #3, was evaluated in calcium mobilization assays.

The human Y5 stably expressed in NIH-3T3 cells (clone #8) was further characterized in saturation binding assays using $^{125}$I-PYY. The binding was saturable over a concentration range of 0.4 pM to 1.9 nM. Binding data were fit to a one-site binding model with an apparent $K_d$ of 0.30 nM ($pK_d$=9.53, n=1) and an apparent $B_{max}$ of 2100 fmol/mg membrane protein using fresh membranes.

The human Y5 stably expressed in LM(tk-) cells (clone #7) was further characterized in saturation binding assays using $^{125}$I-PYY, $^{125}$I-PYY$_{3-36}$, and $^{125}$I-NPY. $^{125}$I-PYY binding was saturable according to a 1-site model over a concentration range of 0.4 pM to 1.9 nM, with an apparent $K_d$ of 0.47 nM ($pK_d$=9.32±0.07, n=5) and an apparent $B_{max}$ of up to 8 pmol/mg membrane protein when membranes had been frozen and stored in liquid nitrogen. Peptide $K_i$ values derived from $^{125}$I-PYY binding to human Y5 receptors from LM(tk-) were comparable to those derived from the previously described human and rat Y5 expression systems (Table 7). $^{125}$I-PYY$_{3-36}$ binding to the human Y5 in LM(tk-) cells was also saturable according to a 1-site model over a concentration range of 0.5 pM to 2.09 nM, with an apparent $K_d$ of 0.40 nM ($pK_d$=9.40, n=1) and an apparent $B_{max}$ of 490 fmol/mg membrane protein when membranes had been frozen and stored in liquid nitrogen. Peptide ligands appeared to bind with comparable affinity to human Y5 receptors in LM(tk-) cells whether the radioligand used was $^{125}$I-PYY or $^{125}$I-PYY$_{3-36}$ (Table 7). Finally, $^{125}$I-NPY binding to the human Y5 in LM(tk-) cells was saturable according to a 1-site model over a concentration range of 0.4 pM to 1.19 nM, with an apparent $K_d$ of 0.28 and an apparent $B_{max}$ of 360 fmol/mg membrane protein when membranes had been frozen and stored in liquid nitrogen.

Considering the saturation binding studies for the human and rat Y5 receptor homologs as a whole, the data provide evidence that the Y5 receptor is a target for multiple radioiodinated peptide analogs in the pancreatic polypeptide family, including $^{125}$I-PYY, $^{125}$I-NPY, $^{125}$I-PYY$_{3-36}$, and $^{125}$I-[Leu$^{31}$, Pro$^{34}$]PYY. The so-called Y1 and Y2-selective radioligands (such as $^{125}$I-[Leu$^{31}$,Pro$^{34}$]PYY and $^{125}$I-PYY$_{3-36}$, respectively (Dumont et al., 1995)) should be used with caution when probing native tissues for Y-type receptor expression.

Receptor/G protein Interactions: Effects of Guanine Nucleotides

For a given G protein-coupled receptor, a portion of the receptor population can typically be characterized in the high affinity ligand binding site using discriminating agonists. The binding of GTP or a non-hydrolyzable analog to the G protein causes a conformational change in the receptor which favors a low affinity ligand binding state. We investigated whether the non-hydrolyzable GTP analog, Gpp (NH)p, would alter the binding of $^{125}$I-PYY to Y5 in COS-7 and LM(tk-) cells (FIG. 19). $^{125}$I-PYY binding to both human and rat Y5 receptors in COS-7 cells was relatively insensitive to increasing concentrations of Gpp(NH)p ranging from 1 nM to 100 µM. The human Y5 receptor in LM(tk-) cells, however, displayed a concentration dependent decrease in radioligand binding (-85 fmol/mg membrane protein over the entire concentration range). The difference between the receptor preparations could be explained by several factors, including 1) the types of G proteins available in the host cell for supporting a high affinity receptor-agonist complex, 2) the level of receptor reserve in the host cell, and 3) the efficiency of receptor/G protein coupling, and 4) the intrinsic ability of the agonist (in this case, $^{125}$I-PYY) to distinguish between multiple conformations of the receptor.

Functional Assay

Figure 12:
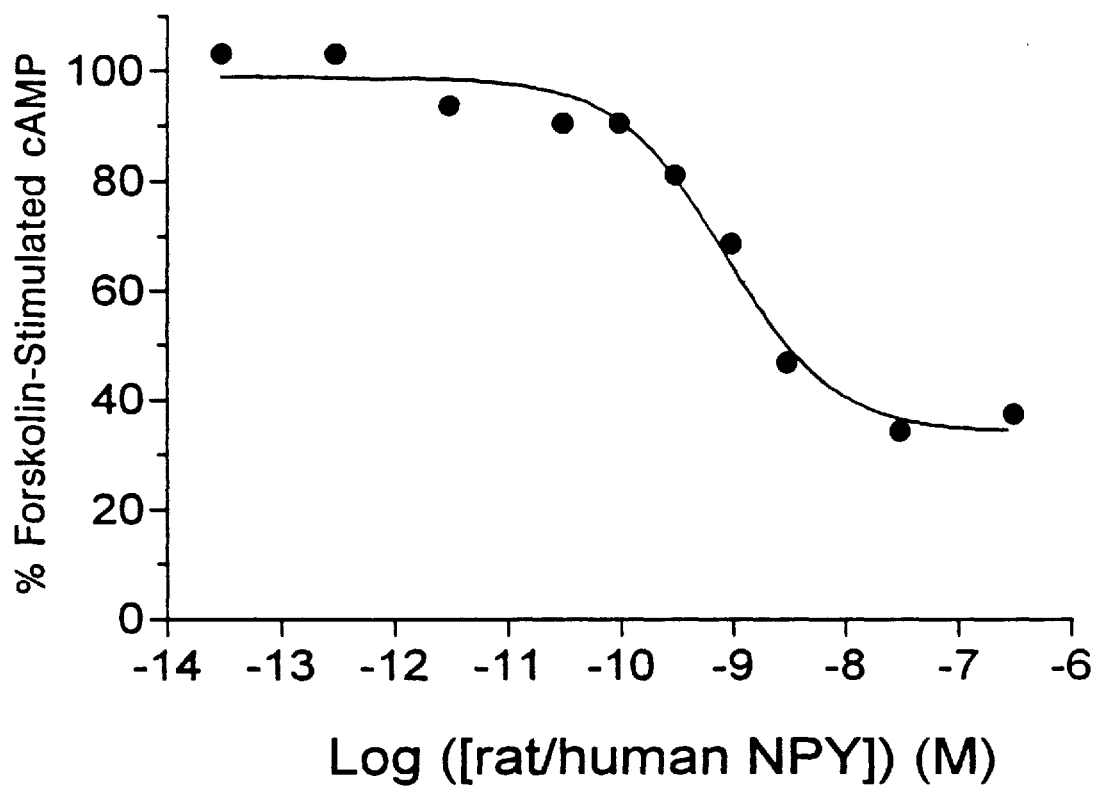
FIG. 12 Inhibition of forskolin-stimulated cAMP accumulation in intact 293 cells stably expressing rat Y5 receptors. Functional data were derived from radioimmunoassay of cAMP in 293 cells stimulated with 10 µM forskolin over a 5 minute period. Rat/human NPY was tested for agonist activity at concentrations ranging from 0.03 pM to 0.3 µM over the same period. The EC$_{50}$ value corresponding to 50% maximal activity was determined by nonlinear regression analysis. The data shown are representative of three independent experiments.
Figure 13D:
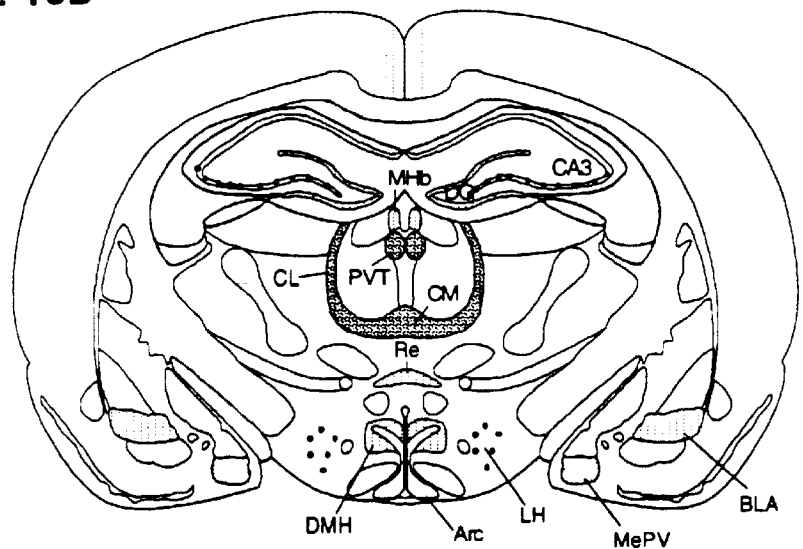
Figure 13E:
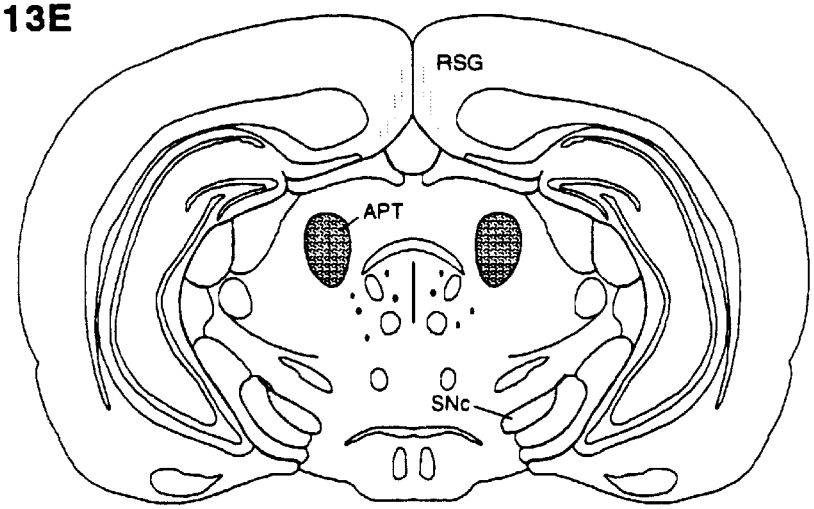
Figure 13F:
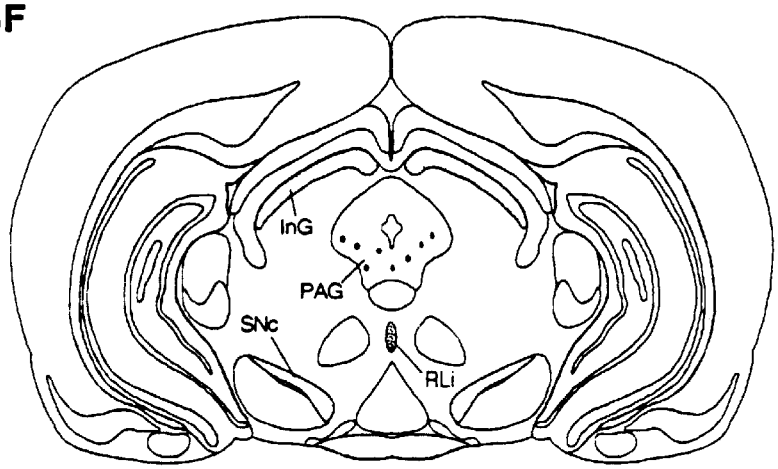
Figure 13G:
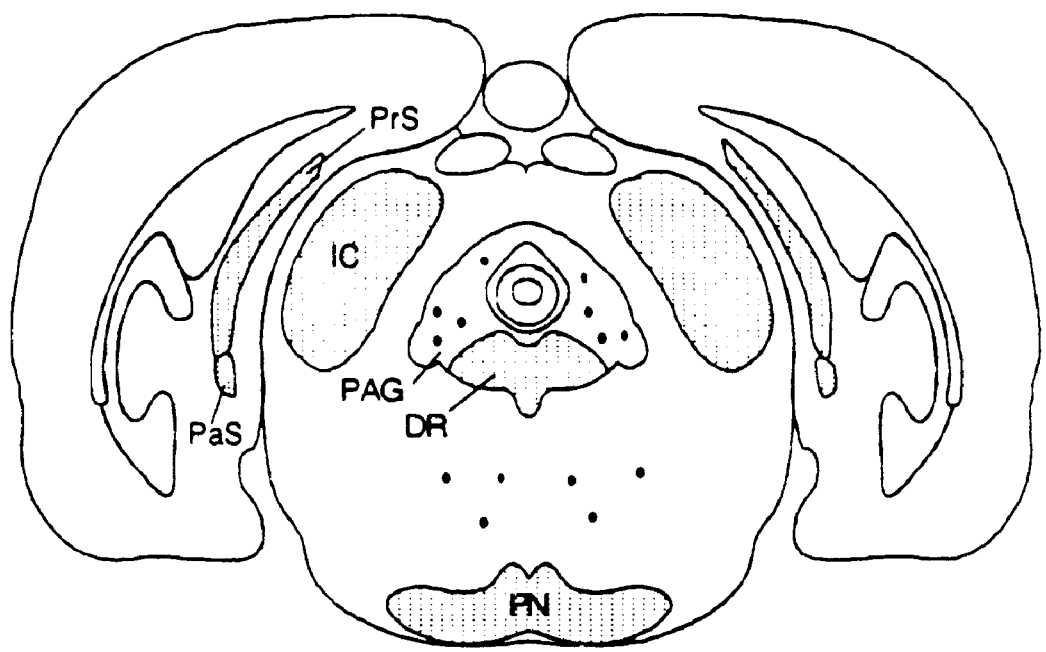
Figure 13H:
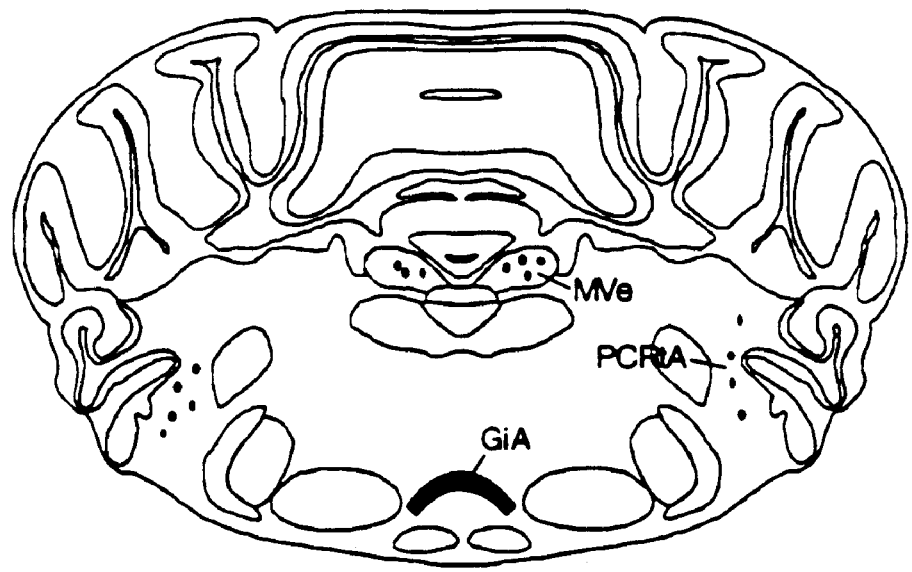

Activation of all Y-type receptors described thus far is thought to involve coupling to pertussis toxin-sensitive G-proteins which are inhibitory for adenylate cyclase activity ($G_i$ or $G_o$) (Wahlestedt and Reis, 1993). That the atypical Y1 receptor is linked to cyclase inhibition was prompted by the observation that pertussis toxin inhibited NPY-induced feeding in vivo (Chance et al., 1989); a more definitive analysis was impossible in the absence of the isolated receptor. Based on these prior observations, applicants investigated the ability of NPY to inhibit forskolin-stimulated cAMP accumulation in human embryonic kidney 293 cells stably transfected with rat Y5 receptors. Incubation of intact cells with 10 µM forskolin produced a 10-fold increase in cAMP accumulation over a 5 minute period, as determined by radioimmunoassay. Simultaneous incubation with rat/human NPY decreased the forskolin-stimulated cAMP accumulation by 67% in stably transfected cells (FIG. 12), but not in untransfected cells (data not shown). Applicants conclude that the rat Y5 receptor activation results in decreased cAMP accumulation, very likely through inhibition of adenylate cyclase activity. This result is consistent with the proposed signalling pathway for all Y-type receptors and for the atypical Y1 receptor in particular.

Peptides selected for their ability to stimulate feeding behavior in rats were able to activate the rat Y5 receptor with $EC_{50}$<10 nM (Kalra et al., 1991; Stanley et al., 1992; Balasubramaniam et al., 1994). These include rat/human NPY ($EC_{50}$=1.8 nM), rat/human NPY$_{2-36}$ ($EC_{50}$=2.0 nM), rat/human [Leu$^{31}$,Pro$^{34}$]NPY ($EC_{50}$=0.6 nM), rat/porcine PYY ($EC_{50}$=4.0 nM), and rat/human [D-Trp$^{32}$]NPY ($EC_{50}$=7.5 nM) (Table 9). $K_i$ values derived from rat Y5-dependent binding of $^{125}$I-PYY and peptide ligands (Table 5) were in close range of EC$_{50}$ values derived from rat Y5-dependent regulation of cAMP accumulation (Table 9). The maximal suppression of cAMP produced by all peptides in Table 9 was between 84% and 120% of that produced by human NPY, except in the case of FLRFamide (42%). Of particular interest is the Y5-selective peptide [D-Trp$^{32}$]NPY. This is a peptide which was shown to stimulate food intake when injected into rat hypothalamus, and which also attenuated NPY-induced feeding in the same paradigm (Balasubramaniam, 1994). Applicants observed that [D-Trp$^{32}$]NPY bound weakly to other Y-type clones with K$_i$>500 nM (Tables 5 and 6) and displayed no activity in functional assays (Table 11). In striking contrast, [D-Trp$^{32}$]NPY bound to the rat Y5 receptor with a K$_i$=53 nM and was fully able to mimic the inhibitory effect of NPY on forskolin-stimulated cAMP accumulation with an EC$_{50}$ of 25 nm and an E$_{max}$=72%. That [D-Trp$^{32}$]NPY was able to selectively activate the Y5 receptor while having no detectable activity at the other subtype clones strongly suggests that Y5 receptor activation is responsible for the stimulatory effect of [D-Trp$^{32}$]NPY on feeding behavior in vivo.

TABLE 9: Functional activation of the rat Y5 receptor.

Functional data were derived from radioimmunoassay of cAMP accumulation in stably transfected 293 cells stimulated with 10 µM forskolin. Peptides were tested for agonist activity at concentrations ranging from 0.03 pM to 0.3 µM. The maximum inhibition of cAMP accumulation (E$_{max}$) and the concentration producing a half-maximal effect (EC$_{50}$) were determined by nonlinear regression analysis according to a 4 parameter logistic equation. New peptides are marked with a double asterisk.

TABLE 9

| Peptide | E$_{max}$ | EC$_{50}$ (nM) |
|---|---|---|
| rat/human NPY | 67% | 1.8 |
| porcine NPY ** | | 0.79 |
| rat/human NPY$_{2-36}$ | 84% | 2.0 |
| porcine NPY$_{2-36}$ ** | | 1.2 |
| porcine NPY$_{13-36}$ ** | | 21 |
| rat/human [Leu$^{31}$, Pro$^{34}$] NPY | 70% | 0.6 |
| porcine [Leu$^{31}$, Pro$^{34}$] NPY ** | | 1.1 |
| porcine C2-NPY ** | | 240 |
| rat/human [D-Trp$^{32}$] NPY | 72% | 9.5 |
| rat/porcine PYY | 86% | 4.0 |
| human PYY ** | | 1.5 |
| human PYY$_{3-36}$ ** | | 4.9 |
| human [Pro$^{34}$] PYY ** | | 1.8 |
| human PP ** | | 1.4 |
| bovine PP ** | | 5.7 |
| salmon PP ** | | 0.92 |
| rat PP ** | | 130 |
| PYX-1 ** | | >300 |
| PYX-2 ** | | >300 |
| FLRFamide ** | | 13 000 |

The ability of the human Y5 receptor to inhibit cAMP accumulation was evaluated in NIH-3T3 and LM(tk-) cells, neither of which display an NPY-dependent regulation of [cAMP] without the Y5 construct. Intact cells stably transfected with the human Y5 receptor were analyzed as described above for the rat Y5 cAMP assay. Incubation of stably transfected NIH-3T3 cells with 10 uM forskolin generated an average 21-fold increase in [cAMP] (n=2). Simultaneous incubation with human NPY decreased the forskolin-stimulated [cAMP] with an E$_{max}$ of 42% and an EC$_{50}$ of 8.5 nM (FIG. 20). The technique of suspending and then replating the Y5-transfected LM(tk-) cells was correlated with a robust and reliable cellular response to NPY-like peptides and was therefore incorporated into the standard methodology for the functional evaluation of the human Y5 in LM(tk-). Incubation of stably transfected LM(tk-) cells prepared in this manner produced an average 7.4-fold increase in [cAMP] (n=87). Simultaneous incubation with human NPY decreased the forskolin-stimulated [cAMP] with an E$_{max}$ of 72% and with an EC$_{50}$ of 2.4 nM (FIG. 21). The human Y5 receptor supported a cellular response to NPY-like peptides in a rank order similar to that described for the rat Y5 receptor (Table 6, 10). As the rat Y5 receptor is clearly linked by D-Trp32-NPY and other pharmacological tools to the NPY-dependent regulation of feeding behavior, the human Y5 receptor is predicted to function in a similar fashion. Both the human and receptor homologs represent useful models for the screening of compounds intended to modulate feeding behavior by interfering with NPY-dependent pathways.

TABLE 10: Functional activation of the human Y5 receptor in a cAMP radioimmunoassay.

Functional data were derived from radioimmunoassay of cAMP accumulation in stably transfected LM(tk-) cells stimulated with 10 µM forskolin. Peptides were tested for agonist activity at concentrations ranging from 0.03 pM to 0.3 µM. The maximum inhibition of cAMP accumulation (E$_{max}$) and the concentration producing a half-maximal effect (EC$_{50}$) were determined by nonlinear regression analysis according to a 4 parameter logistic equation.

TABLE 10

| Peptide | % inhibition relative to human NPY | EC$_{50}$ (nM) |
|---|---|---|
| rat/human NPY | 100% | 2.7 |
| porcine NPY | 107% | 0.99 |
| rat/human NPY$_{2-36}$ | 116% | 2.6 |
| porcine NPY$_{2-36}$ | 85% | 0.71 |
| porcine NPY$_{13-36}$ | | 49 |
| rat/human [Leu$^{31}$, Pro$^{34}$] NPY | | 3.0 |
| porcine [Leu$^{31}$, Pro$^{34}$] NPY | | 1.3 |
| rat/human [D-Trp$^{32}$] NPY | 108% | 26 |
| rat/porcine PYY | 109% | 3.6 |
| human PYY | 111% | 4.9 |
| human PYY$_{3-36}$ | | 18 |
| human [Pro$^{34}$] PYY | 108% | 2.5 |
| human PP | 96% | 14 |
| human PP$_{2-36}$ | | 2.0 |
| human [Ile$^{31}$, Gln$^{34}$] PP | | 5.6 |
| bovine PP | | 4.0 |
| salmon PP | 96% | 4.5 |

TABLE 11: Binding and functional characterization of [D-Trp$^{32}$]NPY.

Binding data were generated as described in Tables 5 and 6. Functional data were derived from radioimmunoassay of cAMP accumulation in stably transfected cells stimulated with 10 µM forskolin. [D-Trp$^{32}$]NPY was tested for agonist activity at concentrations ranging from 0.03 pM to 0.3 µM. Alternatively, [D-Trp$^{32}$]NPY was included as a single spike (0.3 µM) in the human PYY concentration curve for human Y1 and human Y2 receptors, or in the human PP concentration curve for human Y4 receptors, and antagonist activity was detected by the presence of a rightward shift (from EC$_{50}$ to EC$_{50}$'). K$_b$ values were calculated according to the equation: K$_b$=[[D-Trp$^{32}$]NPY/((EC50/EC$_{50}$')−1). The data shown are representative of at least two independent experiments.

TABLE 11

| Receptor Subtype | Species | Binding K$_i$ (nM) | EC$_{50}$ (nM) | K$_b$ (nM0) | Function Activity |
|---|---|---|---|---|---|
| Y1 | Human | >1000 | | | None detected |
| Y2 | Human | >1000 | | | None detected |
| Y4 | Human | >1000 | | | None detected |
| Y5 | Human | 18 | 26 | | Not Determined |
| Y1 | Rat | >1000 | | | Not Determined |
| Y2 | Rat | >1000 | | Not | Determined |
| Y4 | Rat | >1000 | | | Not Determined |
| Y5 | Rat | 53 | 9.50 | | Agonist |

Functional Assay: Intracellular Calcium Mobilization

Figure 21A:
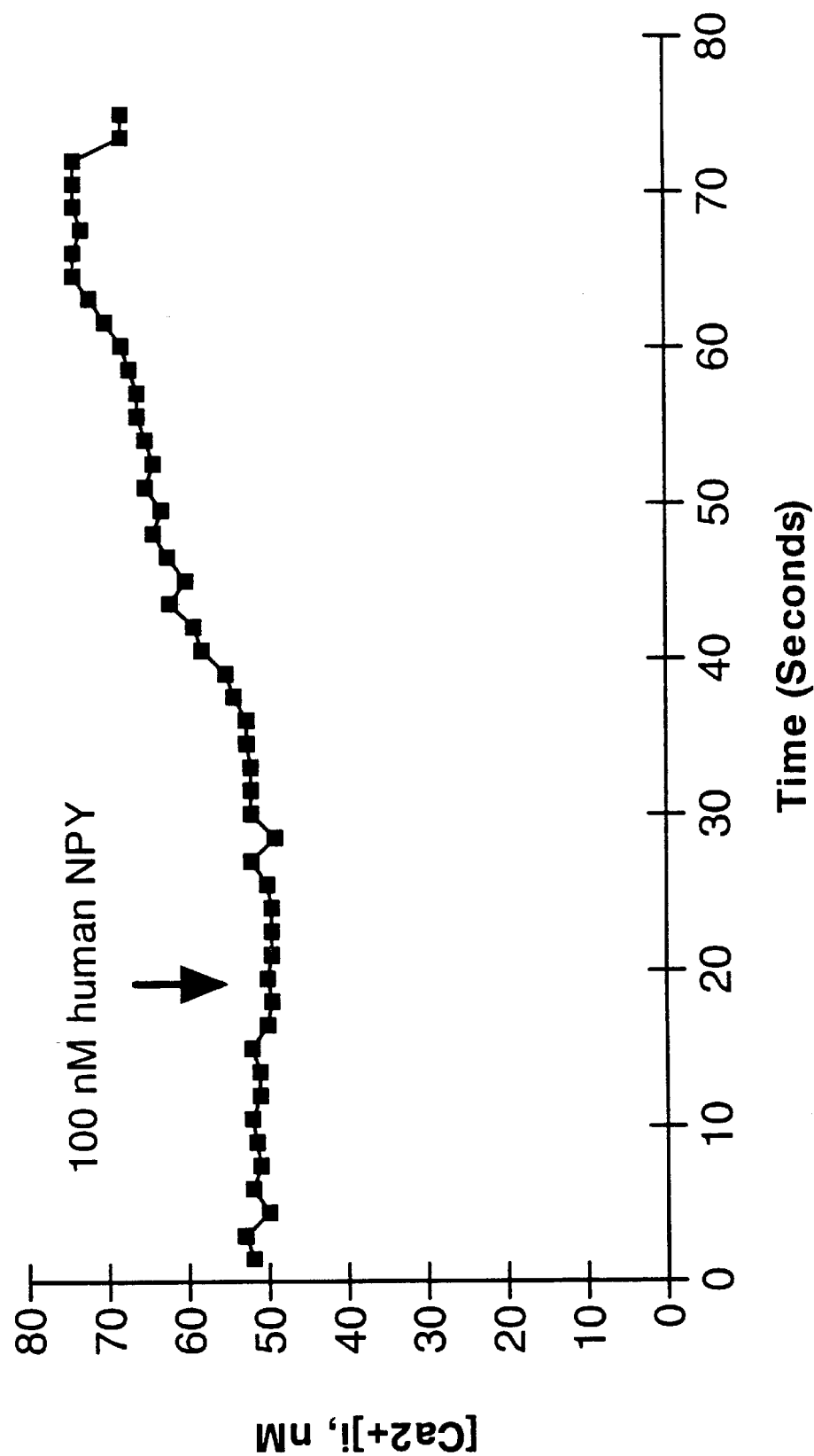
Figure 21B:
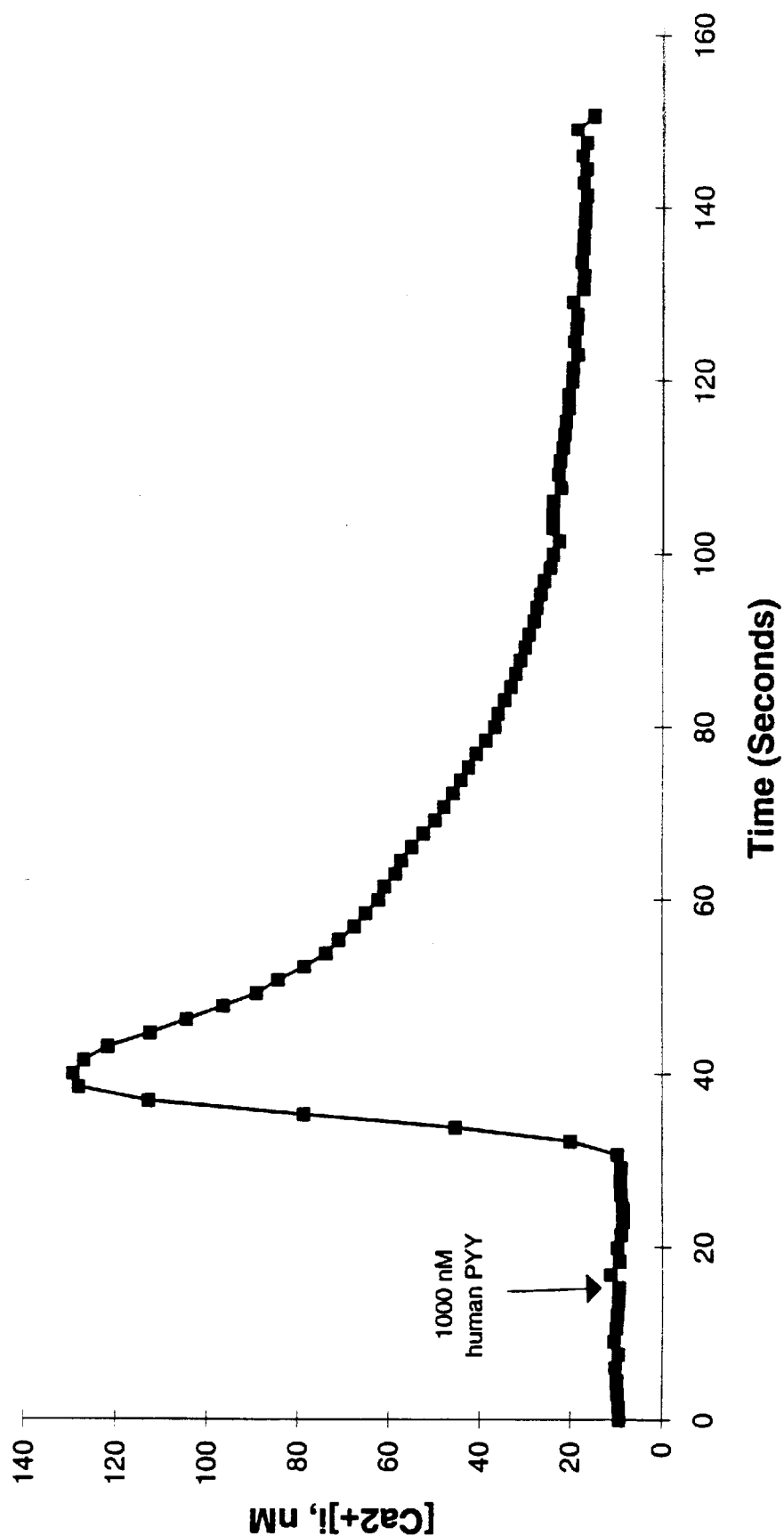
Figure 21D:
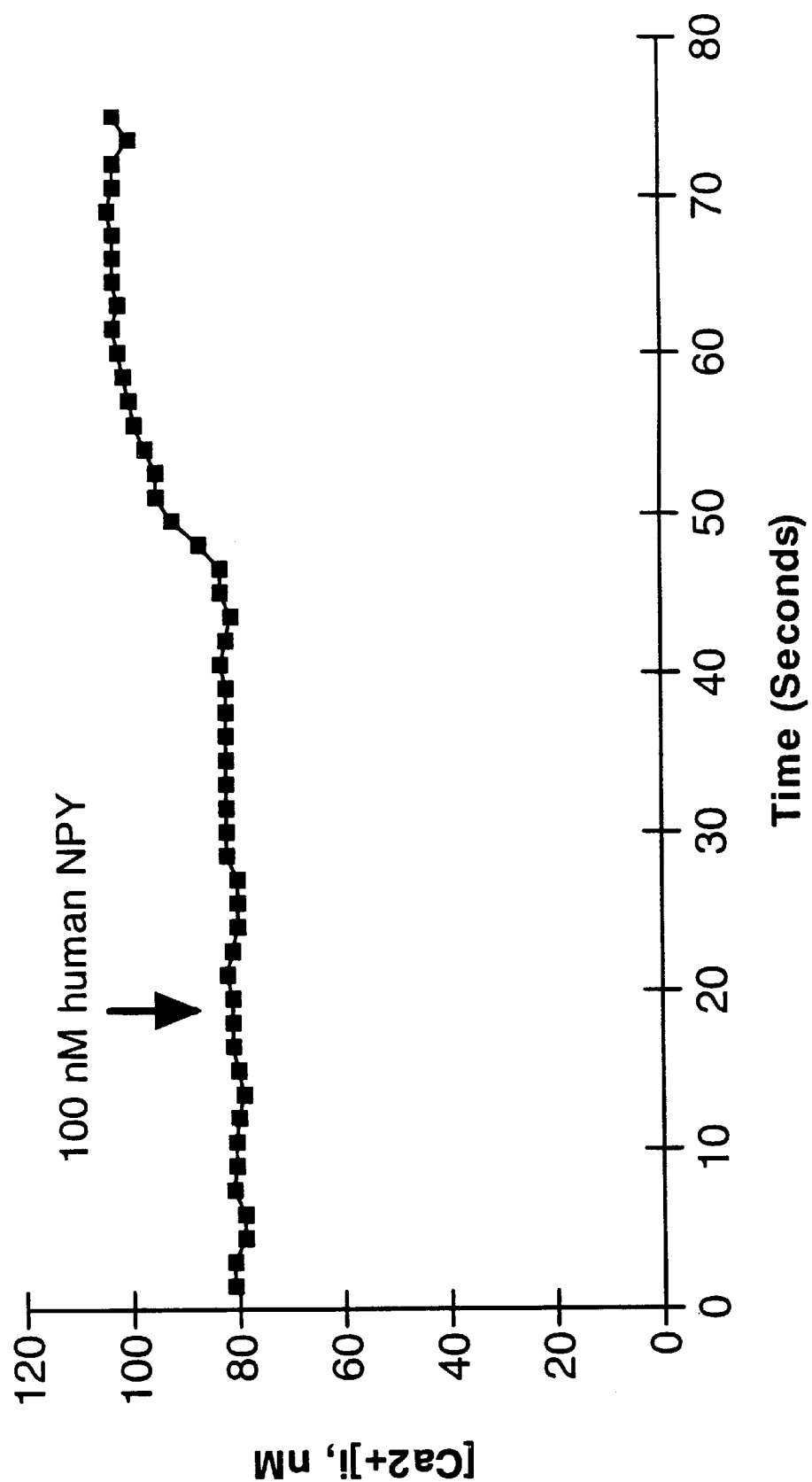

The intracellular free calcium concentration was increased in LM(tk−) cells stably transfected with the human Y5 receptor within 30 seconds of incubation with 100 nM human NPY (Δ Ca$^{2+}$=34 nM, FIG. 21D). Untransfected LM(tk−) cells did not respond to human NPY (data not shown). The calcium mobilization provides a second pathway through which Y5 receptor activation can be measured. These data also serve to link with the Y5 receptor with other cloned human Y-type receptors, all of which have been demonstrated to mobilize intracellular calcium in various expression systems (FIG. 21).

Localization Studies

The mRNA for the NPY Y5 receptor was widely distributed in rat brain, and appeared to be moderately abundant (Table 12 and FIG. 13). The midline thalamus contained many neurons with silver grains over them, particularly the paraventricular thalamic nucleus, the rhomboid nucleus, and the nucleus reunions. In addition, moderately intense hybridization signals were observed over neurons in both the centromedial and anterodorsal thalamic nuclei. In the hypothalamus, a moderate level of hybridization signal was seen over scattered neurons in the lateral hypothalamus, paraventricular, supraoptic, arcuate, and dorsomedial nuclei. In both the medial preoptic nucleus and suprachiasmatic nucleus, weak or moderate accumulations of silver grains were present. In the suprachiasmatic nucleus, hybridization signal was restricted mainly to the ventrolateral subdivision. In the paraventricular hypothalamus, positive neurons were observed primarily in the medial parvicellular subdivision.

TABLE 12

Distribution of NPY Y5 mRNA in the Rat CNS

| REGION | Y5 mRNA |
|---|---|
| Cerebral cortex | +1 |
| Thalamus | |
| paraventricular n. | +3 |
| rhomboid n. | +3 |
| reunions n. | +3 |
| anterodorsal n. | +2 |
| Hypothalamus | |
| paraventricular n. | +2 |
| lateral hypoth. area | +2/+3 |
| supraoptic n. | +1 |
| medial preoptic n. | +2 |
| suprachiasmatic n. | +1/+2 |
| arcuate n. | +2 |
| Hippocampus | |
| dentate gyrus | +1 |
| polymorph dentate gyrus | +2 |
| CA1 | 0 |
| CA3 | +1 |
| Amygdala | |
| central amygd. n., medial | +2 |
| anterior cortical amygd. n. | +2 |
| Olivary pretectal n. | +3 |
| Anterior pretectal n. | +3 |
| Substantia nigra, pars compacta | +2 |
| Superior colliculus | +2 |
| Central gray | +2 |
| Rostral linear raphe | +3 |
| Dorsal raphe | +1 |
| Inferior colliculus | +1 |
| Medial vestibular n. | +2/+3 |
| Parvicellular ret. n., alpha | +2 |
| Gigantocellular reticular n., alpha | +2 |
| Pontine nuclei | +1/+2 |

Moderate hybridization signals were found over most of the neurons in the polymorphic region of the dentate gyrus in the hippocampus, while lower levels were seen over scattered neurons in the CA3 region. In the amygdala, the central nucleus and the anterior cortical nucleus contained neurons with moderate levels of hybridization signal. In the mesencephalon, hybridization signals were observed over a number of areas. The most intense signals were found over neurons in the anterior and olivary pretectal nuclei, periaquaductal gray, and over the rostral linear raphe. Moderate hybridization signals were observed over neurons in the internal gray layer of the superior colliculus, the substantia nigra, pars compacta, the dorsal raphe, and the pontine nuclei. Most of the neurons in the inferior colliculus exhibited a low level of signal. In the medulla and pons, few areas exhibited substantial hybridization signals. The medial vestibular nucleus was moderately labeled, as was the parvicellular reticular nucleus, pars alpha, and the gigantocellular reticular nucleus.

Little or no hybridization signal was observed on sections hybridized with the radiolabeled sense oligonucleotide probe. More importantly, in the transfected COS-7 cells, the antisense probe hybridized only to the cells transfected with the rat Y5 cDNA (Table 13). These results indicate that the probe used to characterize the distribution of Y5 mRNA in rat brain is specific for this mRNA, and does not cross-hybridize to any of the other known NPY receptor mRNAs.
TABLE 13: Hybridization of antisense oligonucleotide probes to transfected COS-7 cells.

Hybridization was performed as described in Methods. The NPY Y5 probe hybridizes only to the cells transfected with the Y5 cDNA. ND=not done.

| Cells | Mock | rY1 | rY2 | rY4 | rY5 |
|---|---|---|---|---|---|
| Oligo | | | | | |
| rY1 | − | + | − | ND | ND |
| rY2 | − | − | + | − | − |
| rY4 | − | − | − | + | − |
| rY5 | − | − | − | − | + |

In vivo studies with Y5-selective compounds

The results reported above strongly support a role for the Y5 receptor in regulating feeding behavior. Accordingly, applicants have synthesized and evaluated the binding and functional properties of several compounds at the cloned human Y1, human Y2, human Y4, and human Y5 receptors.

As shown below in Table 14, applicants have discovered several compounds which bind selectively to the human Y5 receptor and act as Y5 receptor antagonists, as measured by their ability to block NPY-induced inhibition of cAMP accumulation in forskolin-stimulated LM(tk−) cells stably transfected with the cloned human Y5 receptor. The structures of the compounds described in Table 13 are shown in FIG. 22. Preliminary experiments indicate that compound 28 is a Y5 receptor antagonist.

Table 14: Evaluation of human Y5 receptor antagonists

The ability of the compounds to antagonize the Y-type receptors is reported as the $K_b$. The $K_b$ is derived from the $EC_{50}$, or concentration of half-maximal effect, in the presence ($EC_{50}$) or absence ($EC_{50}'$) of compound, according to the equation: $K_b = [NPY]/((EC_{50}/EC_{50}')-1)$. Results shown are representative of at least three independent experiments. N.D.=Not determined.

TABLE 14

| | Binding Affinity ($K_i$ (nM) vs. $^{125}$I-PYY) | | | | $K_b$ (nM) |
|---|---|---|---|---|---|
| Compound | Human Receptor | | | | |
| | Y1 | Y2 | Y4 | Y5 | |
| 1 | 1660 | 1920 | 4540 | 38.9 | 183 |
| 2 | 1806 | 386 | 1280 | 17.8 | 9.6 |
| 5 | 3860 | 249 | 2290 | 1.27 | 2.1 |
| 6 | 4360 | 4610 | 32,900 | 47.5 | 93 |
| 7 | 2170 | 2870 | 7050 | 42.0 | 105 |
| 9 | 3240 | >100,000 | 3720 | 108 | 479 |
| 10 | 1070 | >100,000 | 5830 | 40.7 | 2.8 |
| 11 | 1180 | >100,000 | 7130 | 9.66 | 1.5 |
| 17 | 5550 | 1000 | 8020 | 14 | 6.0 |
| 19 | 3550 | 955 | 11700 | 11 | 23 |
| 20 | 16000 | 7760 | 20400 | 8.3 | 26 |
| 21 | 13000 | 1610 | 18500 | 9.8 | 16 |
| 22 | 17200 | 7570 | 27500 | 11 | 3.0 |
| 23 | 14500 | 617 | 21500 | 26 | 38 |
| 25 | 3240 | 851 | 13100 | 17 | 311 |
| 26 | 23700 | 58200 | 19300 | 14 | 50 |
| 27 | 48700 | 5280 | 63100 | 28 | 49 |
| 28 | >100,000 | >75,000 | >100,000 | 19,000 | N.D. |

Several of these compounds were further tested using in vivo animal models of feeding behavior.

Since NPY is the strongest known stimulant of feeding behavior, experiments were performed with several compounds to evaluate the effect of the compounds described above on NPY-induced feeding behavior in satiated rats.

First, 300 pmole of porcine NPY in vehicle (A.C.S.F.) was administered by intracerebroventricular (i.c.v.) injection, along with i.p. administration of compound vehicle (10% DMSO/water), and the food intake of NPY-stimulated animals was compared to food intake in animals treated with the vehicles. The 300 pmole injection of NPY was found to significantly induce food intake ($p<0.05$; Student-Newman-Keuls).

Using the 300 pmole dose of NPY found to be effective to stimulate feeding, other animals were treated with the compounds by intraperitoneal (i.p.) administration, followed 30–60 minutes later by i.c.v. NPY administration, and measurement of subsequent food intake. As shown in Table 15, NPY-induced food intake was significantly reduced in animals first treated with the compounds ($p<0.05$; Student-Newman-Keuls). These experiments demonstrate that NPY-induced food intake is significantly reduced by administration to animals of a compound which is a Y5-selective antagonist.

Table 15. NPY-induced cumulative food intake in rats treated with either the i.c.v. and i.p. vehicles (control), 300 pmole NPY alone (NPY), or in rats treated first with compound and then NPY (NPY+compound). Food intake was measured 4 hours after stimulation with NPY. Food intake is reported as the mean ±S.E.M. intake for a group of animals.

TABLE 15

| | Food intake (g) mean ± S.E.M. | | | |
|---|---|---|---|---|
| Compound | 1 | 5 | 17 | 19 |
| Compound Dose (mg/kg i.p.) | 10 | 10 | 10 | 30 |
| control (vehicles only) | 3.7 ± 0.6 | 2.4 ± 0.5 | 2.4 ± 0.7 | 2.9 ± 0.8 |
| NPY | 7.4 ± 0.5 | 6.8 ± 1.0 | 5.6 ± 0.5 | 4.9 ± 0.4 |
| NPY + compound | 4.6 ± 0.6 | 4.1 ± 0.4 | 3.8 ± 0.4 | 1.5 ± 0.6 |

Since food deprivation induces an increase in the hypothalamic NPY levels, it has been postulated that food intake following a period of food deprivation is NPY-mediated. Therefore, the Y5 antagonists of Table 14 were administered by intraperitoneal injection at a dose of 30 mg/kg to conscious rats following a 24 h food deprivation. The human Y5 receptor antagonists shown in Table 14 reduced food intake in the food-deprived animals, as shown below in Table 16. The food intake of animals treated with test compound is reported as the percentage of the food intake measured for control animals (treated with vehicle), i.e., 25 means the animals treated with the compound consumed only 25% as much food as the control animals. Measurements were performed two hours after administration of the test compound.

Table 16 Two-hour food intake of food-deprived rats.

Food intake is expressed as the percentage of intake compared to control rats. N.D.=Not done.

| Compound | Mean (%) | Compound | Mean (%) |
|---|---|---|---|
| 1 | 34 | 19 | 36 |
| 2 | 42 | 20 | 35 |
| 5 | 87 | 21 | 80 |
| 6 | 38 | 22 | 55 |
| 7 | 47 | 23 | 58 |
| 9 | 40 | 25 | 32 |

-continued

| Compound | Mean (%) | Compound | Mean (%) |
|---|---|---|---|
| 10 | 74 | 26 | 73 |
| 11 | 15 | 27 | 84 |
| 17 | 27 | 28 | ND |

These experiments indicate that the compounds of the present invention inhibit food intake in rats, especially when administered in a range of about 0.01 to about 100 mg/kg rat, by either oral, intraperitoneal or intravenous administration. The animals appeared normal during these experiments, and no ill effects on the animals were observed after the termination of the feeding experiments.

The binding properties of the compounds were also evaluated with respect to other cloned human G-protein coupled receptors. As shown in Table 17, below, the Y5-selective compounds described hereinabove exhibited lower affinity for receptors other than the Y-type receptors.

TABLE 17

Cross-reactivity of compounds at other cloned human receptors

| Com-pound | Receptor (pKi) | | | | | | | | |
|---|---|---|---|---|---|---|---|---|---|
| | $\alpha_{1d}$ | $\alpha_{ib}$ | $\alpha_{1a}$ | $\alpha_{2a}$ | $\alpha_{2b}$ | $\alpha_{2c}$ | H1 | H2 | D3 |
| 1 | 6.25 | 6.23 | 6.15 | 6.28 | 6.01 | 6.34 | 5.59 | 6.32 | 5.69 |
| 2 | N.D. | N.D. | N.D. | N.D. | N.D. | N.D. | N.D. | N.D. | N.D. |
| 5 | 7.24 | 7.36 | 7.63 | 7.39 | 7.29 | 7.63 | 6.65 | 6.68 | 7.24 |
| 6 | 5.68 | 5.73 | 6.54 | 7.14 | 5.79 | 6.35 | N.D. | N.D. | N.D. |
| 7 | 6.46 | 6.08 | 6.06 | 7.16 | 6.09 | 6.85 | N.D. | N.D. | N.D. |
| 9 | 6.45 | 6.26 | 6.57 | 7.04 | 5.00 | 6.81 | N.D. | N.D. | N.D. |
| 10 | 6.12 | 5.82 | 6.27 | 8.94 | 5.62 | 6.18 | N.D. | N.D. | N.D. |
| 11 | 7.03 | 5.6 | 6.05 | 7.38 | 5.60 | 6.00 | N.D. | N.D. | N.D. |
| 17 | 6.68 | 7.17 | 7.08 | 6.52 | 6.51 | 7.07 | 6.33 | 5.92 | 6.61 |
| 19 | 6.90 | 7.35 | 7.47 | 6.74 | 6.58 | 7.07 | 7.04 | 6.29 | 6.69 |
| 20 | 7.01 | 7.22 | 7.72 | 7.31 | 6.96 | 7.39 | 6.73 | 5.85 | 6.35 |
| 21 | N.D. | N.D. | N.D. | N.D. | N.D. | N.D. | N.D. | N.D. | N.D. |
| 22 | 6.80 | 6.98 | 7.34 | 7.05 | 6.43 | 7.15 | 6.22 | 5.72 | 6.29 |
| 23 | N.D. | N.D. | N.D. | N.D. | N.D. | N.D. | N.D. | N.D. | N.D. |
| 25 | 6.66 | 6.67 | 7.07 | 6.21 | 5.95 | 6.79 | 6.43 | 6.43 | 5.93 |
| 26 | N.D. | N.D. | N.D. | N.D. | N.D. | N.D. | N.D. | N.D. | N.D. |
| 27 | N.D. | N.D. | N.D. | N.D. | N.D. | N.D. | N.D. | N.D. | N.D. |

| Com-pound | Receptor (pKi) | | | | | | |
|---|---|---|---|---|---|---|---|
| | $5HT_{1a}$ | $5HT_2$ | $5HT_7$ | $5HT_{1F}$ | $5HT_{1E}$ | $5HT_{1D\beta}$ | $5HT_{1D\alpha}$ |
| 1 | 4.51 | 6.34 | 6.20 | 5.30 | 5.30 | 5.30 | 5.42 |
| 2 | N.D. | N.D. | N.D. | N.D. | N.D. | N.D. | N.D |
| 5 | 6.33 | 6.41 | 6.00 | 5.30 | 5.30 | 5.55 | 5.37 |
| 6 | N.D. | N.D. | 6.00 | 5.30 | 5.30 | 5.30 | 5.30 |
| 7 | N.D. | N.D. | 6.64 | 5.30 | 5.30 | 5.30 | 5.85 |
| 9 | N.D. | N.D. | 6.48 | 5.30 | 5.30 | 5.30 | 5.30 |
| 10 | N.D. | N.D. | 5.87 | 5.30 | 5.30 | 5.30 | 5.30 |
| 11 | N.D. | N.D. | 6.20 | 5.30 | 5.30 | 5.30 | 5.30 |
| 17 | 5.88 | 6.74 | 6.50 | 5.30 | 5.30 | 5.30 | 5.32 |
| 19 | 5.54 | 6.55 | 6.42 | 5.30 | 5.30 | 5.30 | 6.04 |
| 20 | 6.73 | 5.93 | 6.37 | 5.30 | 5.30 | 5.37 | 5.94 |
| 21 | N.D. | N.D. | N.D. | N.D. | N.D. | N.D. | N.D. |
| 22 | 6.56 | 5.99 | 6.39 | 5.30 | 5.30 | 5.41 | 5.98 |
| 23 | N.D. | N.D. | N.D. | N.D. | N.D. | N.D. | N.D. |
| 25 | 5.82 | 5.99 | 5.35 | 5.30 | 5.30 | 5.39 | 5.62 |
| 26 | N.D. | N.D. | N.D. | N.D. | N.D. | N.D. | N.D. |
| 27 | N.D. | N.D. | N.D. | N.D. | N.D. | N.D. | N.D. |

EXPERIMENTAL DISCUSSION

In order to isolate new NPY receptor subtypes applicants choose an expression cloning approach where a functional receptor is actually detected with exquisite sensitivity on the surface of transfected cells, using a highly specific iodinated ligand. Using this strategy, applicants have identified a rat hypothalamic cDNA encoding a novel Y-type receptor (Y5). The fact that applicants had to screen $3.5 \times 10^6$ independent clones with a 2.7 kb average insert size to find two clones reveals either a very strong bias against Y5 cDNA cloning in the cDNA library construction procedure or that the Y5 mRNA is expressed at very low levels in rat hypothalamic tissue. The longest reading frame in the rat Y5 cDNA (CG-18) encodes a 456 amino acid protein with an estimated molecular weight of 50.1 kD. Given there are two N-linked glycosylation site in the amino terminus, the apparent molecular weight could be slightly higher. Applicants have isolated the human Y5 homolog from a human hippocampal cDNA library. The longest reading frame in the human Y5 cDNA (CG-19) encodes a 455 amino acid protein with an estimated molecular weight of 50 kD. The human Y5 receptor is one amino acid shorter than the rat Y5 and shows significant amino acid differences both in the N-terminal and the middle of the third intracellular loop portions of the protein. The seven transmembrane domains and the extracellular loops, however, are virtually identical and the protein motifs found in both species homologs are identical. Both human and rat Y5 receptors carry a large number of potential phosphorylation sites in their second and third intracellular loops which could be involved in the regulation of their functional characteristics.

The rat and human Y5 receptors both carry a leucine zipper in the first putative transmembrane domain. In such a structure, it has been proposed that segments containing periodic arrays of leucine residues exist in an alpha-helical conformation. The leucine side chains extending from one alpha-helix interact with those from a similar alpha helix of a second polypeptide, facilitating dimerization by the formation of a coiled coil (O'Shea et al, 1989). Usually, such patterns are associated with nuclear DNA binding protein like c-myc, c-fos and c-jun, but it is possible that in some proteins the leucine repeat simply facilitates dimerization and has little to do with positioning a DNA-binding region. Further evidence supporting the idea that dimerization of specific seven transmembrane receptors can occur comes from coexpression studies with muscarinic/adrenergic receptors where intermolecular "cross-talk" between chimeric G-protein coupled receptors has been described (Maggio et al., 1993). The tyrosine phosphorylation site found in the middle of this leucine zipper in transmembrane domain one (TM I) could be involved in regulating dimerization of the Y5 receptor. The physiological significance of G-protein coupled receptor dimerization remains to be elucidated but by analogy with peptide hormone receptors oligomerization, it could be involved in receptor activation and signal transduction (Wells, 1994).

The nucleotide and amino acid sequence analysis of Y5 (rat and human) reveals low identity levels with all 7 TM receptors including the Y1, Y2 and Y4 receptors, even in the transmembrane domains which are usually highly conserved within receptor subfamilies. Applicants have named CG-18 and CG-19 "Y5" receptors because of their unique amino acid sequence (87.2% identical with each other, $\leq 42\%$ identical with the TM regions of previously cloned "Y" receptor subtypes) and pharmacological profile. The name is not biased toward any one member of the pancreatic polypeptide family. The "Y" has its roots in the original classification of Y1 and Y2 receptor subtypes (Wahlestedt et al., 1987). The letter reflects the conservation in pancreatic polypeptide family members of the C-terminal tyrosine, described as "Y" in the single letter amino acid code. The number is the next available in the Y-type series, position number three having been reserved for the pharmacologically defined Y3 receptor. Applicants note that the cloned human Y1 receptor was introduced by Larhammar and co-workers as a "human neuropeptide Y/peptide YY receptor of the Y1 type" (Larhammar et al., 1992). Similarly, the novel clones described herein can be described as rat and human neuropeptide Y/peptide YY receptors of the Y5 type.

The rat hypothalamic Y5 receptor displays a very similar pharmacological profile to the pharmacologically described "atypical" Y1 receptor thought to mediate NPY-induced food intake in rat hypothalamus. Both the Y5 receptor and the "feeding receptor" display a preference for NPY and PYY-like analogs, a sensitivity to N-terminal peptide deletion, and a tolerance for $Pro^{34}$. Each would be considered Y1-like except for the anomalous ability of $NPY_{2-36}$ to bind and activate as well as NPY. Each appears to be sensitive to changes in the mid-region of the peptide ligand. For example, a study by Kalra and colleagues (1991) indicated that replacement of the NPY midregion by an aminooctanoic chain to produce $NPY_{1-4}$–$Aca$–$_{25-36}$ dramatically reduced activity in a feeding behavioral assay. Likewise, applicants note that the robust difference in human PP binding ($K_i$=5.0 nM) and rat PP binding ($K_i$=230) to the rat Y5 receptor can be attributed to a series of 8 amino acid changes between residues 6–30 in the peptide ligands, with human PP bearing the closer resemblance to human NPY. Note also that FLRFamide, a structural analog of the FMRFamide peptide which is reported to stimulate feeding in rats, was able to bind and activate the rat Y5 receptor albeit at relatively high concentrations (Orosco, et al., 1989). These matching profiles, combined with a selective activation of the rat Y5 by the reported feeding "modulator" [D-$Trp^{32}$]NPY, support the identity of the rat Y5 as the "feeding receptor" first proposed to explain NPY-induced feeding in rat hypothalamus. That the human Y5 receptor has a pharmacological profile like that of the rat Y5 in both binding and functional assays suggests that the two receptors may have similar functions in vivo.

The distribution of Y5 mRNA in rat brain further extends the argument for a role of Y5 receptors in feeding behavior. The anatomical locus of the feeding response, for example, has been suggested to reside at least in part in the paraventricular hypothalamic nucleus (PVN) and also in the lateral hypothalamus, two places where Y5 mRNA was detected in abundance. Post-synaptic localization of the Y5 receptor in both of these regions can regulate the response to endogenously released NPY in vivo. The paraventricular nucleus receives projections from NPY-containing neurons in the arcuate nucleus, another region where Y5 mRNA was detected. This indicates a pre-synaptic role for the Y5 receptor in the control of NPY release via the arcuato-paraventricular projection, and consequently in the control of feeding behavior. The localization of the Y5 mRNA in the midline thalamic nuclei is also important. The paraventricular thalamic nucleus/centromedial nucleus complex projects heavily to the paraventricular hypothalamus and to the amygdala. As such, the Y5 receptor is a substrate for the emotional aspect of appetitive behaviors.

Y5 receptors are highly attractive targets for appetite and weight control based on several lines of research (Sahu and Kalra, 1993). NPY is the most potent stimulant of feeding behavior yet described (Clark et al., 1984; Levine and Morley, 1984; Stanley and Leibowitz, 1984). Direct injection of NPY into the hypothalamus of rats can increase food intake ~10-fold over a 4-hour period (Stanley et al., 1992). NPY-stimulated rats display a preference for carbohydrates over protein and fat (Stanley et al., 1985). Interestingly, NPY and NPY mRNA are increased in food-deprived rats (Brady et al., 1990; O'Shea and Gundlach, 1991) and also in rats which are genetically obese (Sanacora et al., 1990) or made diabetic by treatment with streptozotocin (White et al., 1990). One potential explanation is that NPY, a potent stimulant of feeding behavior in normal rats, is disregulated in the overweight or diabetic animal so that food intake is increased, accompanied by obesity. The physiological stress of obesity increases the risk for health problems such as cardiovascular malfunction, osteoarthritis, and hyperinsulinemia, together with a worsened prognosis for adult-onset diabetes. A nonpeptide antagonist targeted to the Y5 receptor could therefore be effective as a way to control not only appetite and body weight but an entire range of obesity- and diabetes-related disorders (Dryden et al., 1994). There is also neurochemical evidence to suggest that NPY-mediated functions are disregulated in eating disorders such as bulimia and anorexia nervosa, so that they too could be responsive to treatment by a Y5-selective drug. It has been proposed, for example, that food intake in NPY-stimulated rats mimics the massive food consumption associated with binge eating in bulimia (Stanley, 1993). CSF levels of PYY but not NPY were elevated in bulimic patients who abstained from binging, and then diminished when binging was allowed (Berrettini et al., 1988). Conversely, NPY levels were elevated in underweight anorectic patients and then diminished as body weight was normalized (Kaye et al., 1990).

As described above, the human and rat in vitro expression models were used in combination to screen for compounds intended to modulate NPY-dependent feeding behavior. Using this approach, applicants have discovered several compounds which inhibit feeding behavior in animal models, which should lead to additional drug discoveries.

The Y5 pharmacological profile further offers a new standard by which to review the molecular basis of all NPY-dependent processes; examples are listed in Table 18. Such an exercise suggests that the Y5 receptor is likely to have a physiological significance beyond feeding behavior. It has been reported, for example, that a Y-type receptor can regulate luteinizing hormone releasing hormone (LHRH) release from the median eminence of steroid-primed rats in vitro with an atypical Y1 pharmacological profile. NPY, $NPY_{2-36}$, and LP-NPY were all effective at 1 uM but deletion of as few as four amino acids from the N-terminus of NPY destroyed biological activity. The Y5 may therefore represent a therapeutic target for sexual or reproductive disorders. Preliminary in situ hybridization of rat Y5 mRNA in hippocampus and elsewhere further suggest that additional roles will be uncovered, for example, in the regulation of memory. It is worth while considering that the Y5 is so similar in pharmacological profile to the other Y-type receptors that it may have been overlooked among a mixed population of Y1, Y2 and Y4 receptors. Certain functions now associated with these subtypes could therefore be reassigned to Y5 as our pharmacological tools grow more sophisticated (Table 18). By offering new insight into NPY receptor pharmacology, the Y5 thereby provides a greater clarity and focus in the field of drug design.

TABLE 18

Pathophysiological Conditions Associate With NPY

The following pathological conditions have been linked to either 1) application of exogenous NPY, or 2) changes in levels of endogenous NPY.

| # | Condition | Reference |
|---|---|---|
| 1 | obesity | Sahu and Kalra, 1993 |
| 2 | eating disorders (anorexia and bulimia nervosa) | Stanley, 1993 |
| 3 | sexual/reproductive function | Clark, 1994 |
| 4 | depression | Heilig and Weiderlov, 1990 |
| 5 | anxiety | Wahlestedt et al., 1993 |
| 6 | cocaine addiction | Wahlestedt et al., 1991 |
| 7 | gastric ulcer | Penner et al., 1993 |
| 8 | memory loss | Morley and Flood, 1990 |
| 9 | pain | Hua et al., 1991 |
| 10 | epileptic seizure | Rizzi et al., 1993 |
| 11 | hypertension | Zukowska-Grojec et al., 1993 |
| 12 | subarachnoid hemorrhage | Abel et al., 1988 |
| 13 | shock | Hauser et al., 1993 |
| 14 | circadian rhythm | Albers and Ferris, 1984 |
| 15 | nasal congestion | Lacroix et al., 1988 |
| 16 | diarrhea | Cox and Cuthbert, 1990 |
| 17 | neurogenic voiding dysfunction | Zoubek et al., 1993 |

A successful strategy for the design of a Y5-receptor based drug or for any drug targeted to single G protein-coupled receptor subtype involves the screening of candidate compounds 1) in radioligand binding assays so as to detect affinity for cross-reactive G protein-coupled receptors, and 2) in physiological assays so as to detect undesirable side effects. In the specific process of screening for a Y5-selective drug, the receptor subtypes most likely to cross-react and therefore most important for radioligand binding screens include the other "Y-type" receptors, Y1, Y2, Y3, and Y4. Cross-reactivity between the Y5 and any of the other subtypes could result in potential complications as suggested by the pathophysiological indications listed in Table 18. In designing a Y5 antagonist for obesity and appetite control, for example, it is important not to design a Y1 antagonist resulting in hypertension or increased anxiety, a Y2 antagonist resulting in memory loss, or a Y4 antagonist resulting in increased appetite.

TABLE 19

Y-Type Receptor Indications

| Y-type Receptor Indications | Receptor Subtype | Drug Activity | Reference |
|---|---|---|---|
| obesity, appetite disorder | atypical Y1 | antagonist | Sahu and Kalra 1993 |
| adult onset diabetes | atypical Y1 | antagonist | Sahu and Kalra, 1993 |
| bulimia nervosa | atypical Y1 | antagonist | Stanley, 1993 |
| pheochromocytoma-induced hypertension | Y1 | antagonist | Grouzman et al., 1989 |
| subarachnoid hemorrhage | Y1 | antagonist | Abel et al., 1988 |
| neurogenic vascular hypertrophy | Y1 | antagonist | Zukowska-Grojec et al., 1993 |
| epileptic seizure | Y2 | antagonist | Rizzi et al., 1993 |
| hypertension central, peripheral regulation | peripheral Y1 central Y3 central Y2 | antagonist agonist antagonist | Grundemar and Hakanson, 1993 Barraco et al., 1991 |
| obesity appetite disorder | Y4 or PP | agonist | Malaisse-Lagae et al., 1977 |
| anorexia nervosa | atypical Y1 | agonist | Berrettini et. al., 1988 |
| anxiety | Y1 | agonist | Wahlestedt et al., 1993 |
| cocaine addiction | Y1 | agonist | Wahlestedt et al., 1991 |
| stress-induced gastric ulcer | Y1 Y4 or PP | agonist agonist | Penner et al., 1993 |
| memory loss | Y2 | agonist | Morley and Flood, 1990 |
| pain | Y2 | agonist | Hua et al., 1991 |
| shock | Y1 | agonist | Hauser et al., 1993 |
| sleep disturbances, jet lag | Y2 | not clear | Albers and Ferris, 1984 |
| nasal decongestion | Y1 Y2 | agonist agonist | Lacroix et al., 1988 |
| diarrhea | Y2 | agonist | Cox and Cuthbert, 1990 |

The cloning of the Y5 receptor from human and rat is especially valuable for receptor characterization based on in situ localization, anti-sense functional knock-out, and gene induction. These studies will generate important information related to Y5 receptor function and its therapeutic significance. The cloned Y5 receptor lends itself to mutagenesis studies in which receptor/ligand interactions can be modeled. The Y5 receptor further allows us to investigate the possibility of other Y-type receptors through homology cloning. These could include new receptor subtypes as well as Y5 species homologs for the establishment of experimental animal models with relevance for human pathology. The Y5 receptor therefore represents an enormous opportunity for the development of novel and selective drug therapies,. particularly those targeted to appetite and weight control, but also for memory loss, depression, anxiety, gastric ulcer, epileptic seizure, pain, hypertension, subarachnoid hemorrhage, sleeping disturbances, nasal congestion, neurogenic voiding dysfuncion, and diarrhea.

In particular, the discovery of Y5-selective antagonists which inhibit food intake in rats provides a method of modifying feeding behavior in a wide variety of vetebrate animals.

REFERENCES

Abel, P. W., Han, C., Noe, B. D., and McDonald, J. K. (1988). Neuropeptide Y: vasoconstrictor effects and possible role in cerebral vasospasm after experimental subarachnoid hemorrhage. *Brain Res.* 463: 250–258.

Albers, H. E., and Ferris, C. F. (1984). Neuropeptide Y: Role in light-dark cycle entrainment of hamster circadian rhythms. *Neurosci. Lett.* 50: 163–168.

Aruffo, A. and Seed, B. (1987). Molecular cloning of a CD28 cDNA by a high efficiency COS cell expression system. *PNAS,* 84, 8573–8577.

Balasubramaniam, A., Sheriff, S., Johnson, M. E., Prabhakaran, M., Huang, Y., Fischer, J. E., and Chance, W. T. (1994). [D-Trp$^{32}$]Neuropeptide Y: A competitive antagonist of NPY in rat hypothalamus. *J. Med. Chem.* 37: 311–815.

Berrettini, W. H., Kaye, W. H., Gwirtsman, H., and Allbright, A. (1988). Cerebrospinal fluid peptide YY immunoreactivity in eating disorders. *Neuropsychobiol* 19: 121–124.

Bradford, M. M. (1976). A rapid and sensitive method for the quantitation of microgram quantities of protein utilizing the principle of protein-dye binding. *Anal. Biochem.* 72: 248–254.

Brady, L. S., Smith, M. A., Gold, P. W., and Herkenham, M. (1990). Altered expression of hypothalamic neuropeptide Y mRNAs in food-restricted and food-deprived rats. *Neuroendocrinology* 52: 441–447.

Chance, W. T., Sheriff, S., Foley-Nelson, T., Fischer, J. E., and Balasubramaniam, A. (1989). Pertuss toxin inhibits neuropeptide Y-induced feeding in rats. *Peptides* 10, 1283–1286.

Clark, J. T. (1994). Aging-induced decrements in neuropeptide Y: The retention of ejaculatory behavior is associated with site-selective differences. *Neurobiology of Aging* 15: 191–196.

Clark, J. T., Kalra, P. S., Crowley, W. R., and Kalra, S. P. (1984). Neuropeptide Y and human pancreatic polypeptide stimulate feeding behavior in rats. *Endocrinology* 115: 427–429.

Cox, H., and Cuthbert, A. W. (1990). The effects of neuropeptide Y and its fragments upon basal and electrically stimulated ion secretion in rat jejunum mucosa. *Br. J. Pharmac.* 101: 247–252.

Cullen, B. (1987). Use of eukaryotic expression technology in the functional analysis of cloned genes. *Methods Enzymol.* 152: 685–704.

Dryden, S., Frankish, H., Wang, Q., and Williams, G. (1994). Neuropeptide Y and energy balance: one way ahead for the treatment of obesity? *Eur. J. Clin. Invest.* 24: 293–308.

Dumont, Y., Fournier, A., St.-Pierre, S., Quiron, R., (1995) Characterization of Neuropeptide Y Binding Sites In Rat Brain Membrane Preparations Using [$^{125}$I] [Leu$^{31}$, Pro$^{34}$] Peptide YY and [$^{125}$I] Peptide YY $_{3-36}$ as Selective Y$_1$ and Y$_2$ Radioligands *J. Pharm. Exper. Ther.* 272(2): 673–680.

Dumont, Y., J. -C. Martel, A. Fournier, S. St-Pierre, and R. Quirion. (1992). Neuropeptide Y and neuropeptide Y receptor subtypes in brain and peripheral tissues. *Progress in Neurobiology* 38: 125–167.

Eva, C., Oberto, A., Sprengel, R. and E. Genazzani. (1992). The murine NPY-1 receptor gene: structure and delineation of tissue specific expression. *FEBS lett.* 314: 285–288.

Eva, C., Keinanen, K., Monyer, H., Seeburg, P., and Sprengel, R. (1990). Molecular cloning of a novel G protein-coupled receptor that may belong to the neuropeptide receptor family. *FEBS Lett.* 271, 80–84.

Fuhlendorff, J., U. Gether, L. Aakerlund, N. Langeland-Johansen, H. Thogersen, S. G. Melberg, U. B. Olsen, O. Thastrup, and T. W. Schwartz. (1990). [Leu$^{31}$,Pro$^{34}$] Neuropeptide Y: A specific Y$_1$ receptor agonist. *Proc. Natl. Acad. Sci. U.S.A.* 87: 182–186.

Gerald, C., Adham, A., Kao, H T, Olsen, M. A., Laz, T. M., Vaysse, P., Hartig, P. R., Branchek, T. A. and R. L. Weinshank. The 5-HT$_4$ receptor: molecular cloning and pharmacological characterization of two splice variants (submitted for publication).

Grouzman, E., Comoy, E., and Bohuon, C. (1989). Plasma neuropeptide Y concentrations in patients with neuroendocrine tumors. *J. Clin. Endoc. Metab.* 68: 808–813.

Grundemar, L. and Rl Hakanson (1994). Neuropeptide Y effector systems: perspectives for drug development. *Trends. Pharmacol.* 15:153–159.

Grundemar, L., J. L. Krstenansky, and R. Hakanson. (1992). Activation of neuropeptide Y1 and neuropeptide Y2 receptors by substituted and truncated neuropeptide Y analogs: identification of signal epitopes. *Eur. J. Pharmacol.* 232: 271–278.

Gubler, U abd B. J. Hoffman. (1983). A simple and very efficient method for generating cDNA libraries. *Gene.* 25, 263–269

Hau, X. -Y., Boublik, J. H., Spicer, M. A., Rivier, J. E., Brown, M. R., and Yaksh, T. L. (1991). The antinociceptive effects of spinally administered neuropeptide Y in the rat: Systematic studies on structure-activity relationship. *JPET* 258: 243–253.

Hauser, G. J., Myers, A. K., Dayao, E. K., and Zukowska-Grojec, Z. (1993). Neuropeptide Y infusion improves hemodynamics and survival in rat endotoxic shock. *Am. J. Physiol.* 265: H1416–H1423.

Heilig, M., and Widerlov, E. (1990). Neuropeptide Y: an overview of central distribution, functional aspects, and possible involvement in neuropsychiatric illnesses. *Acta Psychiatr. Scand.* 82: 95–114.

Herzog, H., Y. J. Hort, H. J. Ball, G. Hayes, J. Shine, and L. Selbie. (1992). Cloned human neuropeptide Y receptor couples to two different second messenger systems. *Proc. Natl. Acad. Sci. U.S.A.* 89: 5794–5798.

Herzog, H., Y. J. Hort, H. J. Ball, G. Hayes, J. Shine, and L. Selbie. (1992). Cloned human neuropeptide Y receptor couples to two different second messenger systems. *Proc. Natl. Acad. Sci. U.S.A.* 89, 5794–5798.

Horstman, D. A., Brandon, S., Wilson, A. L., Guyer, C. A., Cragoe, E. J., Jr., Limbird, L. E. (1990) An Aspartate Conserved among G-protein Receptors Confers Allosteric Regulation of $\alpha_2$-Adrenergic Receptors by Sodium. *J. Biol. Chem.* 265(35):21590–21595.

Kalra, S. P., Fuentes, M., Fournier, A., Parker, S. L., and Crowley, W. R. (1992). Involvement of the Y-1 receptor subtype in the regulation of luteinizing hormone secretion by neuropeptide Y in rats. *Endocrinology* 130: 3323–3330.

Kalra, S. P., Dube, M. G., Fournier, A., and Kalra, P. S. (1991). Structure-function analysis of stimulation of food intake by neuropeptide Y: Effects of receptor agonists. *Physiology & Behavior* 50: 5–9.

Kaye, W. H., Berrettini, W., Gwirtsman, H., and George, D. T. (1990). Altered cerebrospinal fluid neuropeptide Y and peptide YY immunoreactivity in anorexia and bulimia nervosa. *Arch. Gen. Psychiat.* 47: 548–556.

Kieffer, B., Befort, K., Gaveriaux-Ruff, C. and Hirth, C. G. (1992). The δ-opioid receptor: Isolation of a cDNA by expression cloning and pharmacological characterization. *Proc. natl. Acad. Sci. U.S.A.* 89, 12048–12052.

Kingston, R. E. (1987) in Ausubel, F. M., Brent, R., Kingston, R. E., Moore, D. D., Seidman, J. G., Smith, J. A. & Struhl, K. (Eds), *Current Protocols in Molecular Biology*, John Wiley and Sons, N.Y., Vol. 1, pp. 4.2.3–4.2.4.

Kluxen, F. W., Bruns, C. and Lubbert H. (1992). Expression cloning of a rat brain somatostatin receptor cDNA. *Proc. Natl. Acad. Sci. U.S.A.* 89, 4618–4622.

Kornfeld, R. and Kornfeld, S. (1985). Assembly of asparagine linked oligosaccharides. *Annu. Rev. Biochem.* 54, 631–664.

Kozak, M. (1989). The scanning model for translation: an update. *J. Cell Biol.* 108, 229–241.

Kozak, M. (1991). Structural features in eukaryotic mRNAs that modulate the initiation of translation. *J. Biol. Chem.* 266, 19867–19870.

Krause, J., C. Eva, P. H. Seeburg, and R. Sprengel. (1991). Neuropeptide $Y_1$ subtype pharmacology of a recombinantly expressed neuropeptide receptor. *Mol. Pharmacol.* 41: 817–821.

Lacroix, J. S., Stjarne, P., Angard, A., and Lundberg, M. (1988). Sympathetic vascular control of the pig nasal mucosa: reserpine-resistant, non-adrenergic nervous responses in relation to neuropeptide Y and ATP. *Acta Physiol. Scand.* 133: 183–197.

Landschultz, W. H., Johnson, P. F. and S. L. McKnight. (1988). The leucine zipper: a hypothetical structure common to a new class of DNA binding proteins. *Science* 240, 1759–1764.

Larhammar, D., A. G. Blomqvist, F. Yee, E. Jazin, H. Yoo, and C. Wahlestedt. (1992). Cloning and functional expression of a human neuropeptide Y/peptide YY receptor of the Y1 type. *J. Biol. Chem.* 267: 10935–10938.

Levine, A. S., and Morley, J. E. (1984). Neuropeptide Y: A potent inducer of consummatory behavior in rats. *Peptides* 5: 1025–1029.

Maggio, R., Vogel Z. and J. Wess. (1993). Coexpression studies with mutant muscarinic/adrenergic receptors provide evidence for intermolecular "cross-talk" between G-protein-linked receptors. *Proc. Natl. Acad. Sci. U.S.A.* 90: 3103–3107.

Malaisse-Lagai, F., Carpentier, J. -L., Patel, Y. C., Malaisse, W. J., and Orci, L. (1977). Pancreatic polypeptide: A possible role in the regulation of food intake in the mouse. Hypothesis. *Experientia* 33: 915–917.

McCormick, M. (1987). Sib Selection. *Methods in Enzymology*, 151: 445–449.

Miller, J. and Germain, R. N. (1986). Efficient cell surface expression of class II MHC molecules in the absence of associated invariant chain. *J. Exp. Med.* 164: 1478–1489.

Michel, M. C. (1991). Receptors for neuropeptide Y: multiple subtypes and multiple second messengers. *Trends Pharmacol.:* 12: 389–394.

Morley, J. E., and Flood, J. F. (1991). Neuropeptide Y and memory processing. *An. N.Y. Acad. Sci.* 611: 226–231.

Okayama, H. and P. Berg (1983). A cDNA cloning vector that permits expression of cDNA inserts in mammalian cells. *Mol. Cell. Biol.* 3: 280–289.

O'Shea, R. D., and Gundlach, A. L. (1991). Preproneuropeptide Y messenger ribonucleic acid in the hypothalamic arcuate nucleus of the rat is increased in food deprivation or dehydration. *J. Neuroendocrinol.* 3: 11–14.

O'Shea, E. K., Rutkowski, R. and P. S. Kim. (1989). Evidence that the leucine zipper is a coiled coil. *Science* 243: 538–542.

Penner, S. B., Smyth, D. D., and Glavin, G. B. (1993). Effects of neuropeptide Y and [Leu$^{31}$,Pro$^{34}$]Neuropeptide Y on experimental gastric lesion formation and gastric secretion in the rat. *JPET.* 266: 339–343.

Probst, W. C., Snyder, L. A., Schuster, D. I., Brosius, J and Sealfon, S. C. (1992). Sequence alignment of the G-protein coupled receptor superfamily. *DNA and Cell Bio.* 11, 1–20.

Sahu, A., and Kalra, S. P. (1993). Neuropeptidergic regulation of feeding behavior (neuropeptide Y). *Trends Endocrinol. Metab.* 4: 217–224.

Rizzi, M., Samini, R., Sperk, G., and Vezzani, A. (1993). Electrical kindling of the hippocampus is associated with functional activation of neuropeptide Y-containing neurons. *Eur. J. Neuroscience* 5: 1534–1538.

Robert, J. J., Orosco, M., Rouch, C., Jacquot, C., Cohen, Y. (1989) Unexpected Responses of the Obese "Cafeteria" Rat to the Peptide FMRF-Amide. *Pharm. Bioch. Behavior* 34:341–344.

Sanacora, G., Kershaw, M., Finkelstein, J. A., and White, J. D. Increased hypothalamic content of preproneuropeptide Y messenger ribonucleic acid in genetically obese Zucker rats and its regulation by food deprivation. *Endocrinology* 127: 730–737 (1990).

Schwartz, T. W., J. Fuhlendorff, L. L. Kjems, M. S. Kristensen, M. Vervelde, M. O'Hare, J. L. Krstenansky, and B. Bjornholm. (1990). Signal epitopes in the three-dimensional structure of neuropeptide Y. *Ann. N.Y. Acad. Sci.* 611: 35–47.

Stanley, B. G., Magdalin, W., Seirafi, A., Nguyen, M. M., and Leibowitz, S. F. (1992). Evidence for neuropeptide Y mediation of eating produced by food deprivation and for a variant of the $Y_1$ receptor mediating this peptide's effect. *Peptides* 13: 581–587.

Stanley, B. G., and Leibowitz, S. F. (1984). Neuropeptide Y: Stimulation of feeding and drinking by injection into the paraventricular nucleus. *Life Sci.* 35: 2635–2642.

Stanley, B. G. Neuropeptide Y in multiple hypothalamic sites controls eating behavior, endocrine, and autonomic systems for body energy balance. In: *The Biology of Neuropeptide Y and Related Peptides*, pp. 457–509. Eds. W. F. Colmers and C. Wahlestedt. Humana Press, Totowa, N.J. (1993).

Stanley, B. G., Daniel, D. R., Chin, A. S., and Leibowitz, S. F. (1985). Paraventricular nucleus injections of peptide YY and neuropeptide Y preferentially enhance carbohydrate ingestion. *Peptides* 6: 1205–1211.

Wahlestedt, C., L. Edvinsson, E. Ekblad, and R. Hakanson. Effects of neuropeptide Y at sympathetic neuroeffector junctions: Existence of $Y_1$ and $Y_2$ receptors. In: *Neuronal messengers in vascular function*, Fernstrom Symp. No 10., pp. 231–242. Eds A. Nobin and C. H. Owman. Elsevier: Amsterdam (1987).

Wahlestedt, C., Karoum, F., Jaskiw, G., Wyatt, R. J., Larhammar, D., Ekman, R., and Reis, D. J. (1991). Cocaine-induced reduction of brain neuropeptide Y synthesis dependent on medial prefrontal cortex. *Proc. Natl. Acad. Sci.* 88: 2978–2082.

Wahlestedt, C., Regunathan, S., and D. J. Reis (1991). Identification of cultured cells selectively expressing Y1-, Y2-, or Y3-type receptors for neuropeptide Y/peptide YY. *Life Sciences* 50: PL-7–PL-12.

Wahlestedt, C., Pich, E. M., Koob, G. F., Yee, F., and Heilig, M. (1993). Modulation of anxiety and neuropeptide Y-Y1 receptors by antisense oligodeoxynucleotides. *Science* 259: 528–531.

Wahlestedt, C., and D. J. Reis. (1993). Neuropeptide Y-Related Peptides and Their Receptors—Are the Receptors Potential Therapeutic Targets? *Ann. Rev. Pharmacol. Tox.* 32: 309–352

Warden, D. and H. V. Thorne. (1968). Infectivity of polyoma virus DNA for mouse embryo cells in presence of diethylaminoethyl-dextran. *J. Gen. Virol.* 3, 371.

Wells, J. A. (1994). Structural and functional basis for hormone binding and receptor oligomerization. *Current Opinion in Cell Biology* 6: 163–173

White, J. D., Olchovsky, D., Kershaw, M., and Berelowitz, M. (1990). Increased hypothalamic content of preproneuropeptide-Y messenger ribonucleic acid in streptozotocin-diabetic rats. *Endocrinology* 126: 765–772.

Zoubek, J., Somogyi, G. T., and De Groat, W. C. (1993). A comparison of inhibitory effects of neuropeptide Y on rat urinary bladder, urethra, and vas deferens. *Am. J. Physiol.* 265: R536–R543.

Zukowska-Grojec, Z., Haass, M., and Bayorh, M. (1986). Neuropeptide Y and peptide YY mediate non-adrenergic vasoconstriction and modulate sympathetic responses in rats.*Reg. Pept.* 15: 99–110.

Zukowska-Grojec, Z., Bergeson, S., Kuch-Wocial, A., and Colton, C. (1993). Mitogenic effect of neuropeptide Y in rat vascular smooth muscle cells. Neuropeptide Y Conference Abstracts, (Cambridge) C10.

What is claimed is:

1. An isolated nucleic acid encoding a human Y5 receptor, the amino acid sequence of which is encoded by the nucleotide sequence set forth in FIG. 5 (Sequence ID No: 3).

2. An isolated nucleic acid encoding a rat Y5 receptor, the amino acid sequence of which is encoded by the nucleotide sequence set forth in FIG. 3 (Sequence ID No: 1).

3. The nucleic acid of claim 1 or 2, wherein the nucleic acid is DNA.

4. The nucleic acid of claim 3, wherein the DNA is cDNA.

5. The nucleic acid of claim 3, wherein the DNA is genomic DNA.

6. The nucleic acid of claim 1 or 2, wherein the nucleic acid is RNA.

7. A vector comprising the nucleic acid of claim 1 or 2.

8. A vector of claim 7 adapted for expression in a bacterial cell which comprises the regulatory elements necessary for expression of the nucleic acid in the bacterial cell operatively linked to the nucleic acid encoding the Y5 receptor so as to permit expression thereof.

9. A vector of claim 7 adapted for expression in a yeast cell which comprises the regulatory elements necessary for expression of the nucleic acid in the yeast cell operatively linked to the nucleic acid encoding the Y5 receptor so as to permit expression thereof.

10. A vector of claim 7 adapted for expression in a insect cell which comprises the regulatory elements necessary for expression of the nucleic acid in the insect cell operatively linked to the nucleic acid encoding the Y5 receptor so as to permit expression thereof.

11. A vector of claim 7 adapted for expression in a mammalian cell which comprises the regulatory elements necessary for expression of the nucleic acid in the mammalian cell operatively linked to the nucleic acid encoding the Y5 receptor so as to permit expression thereof.

12. A vector of claim 11, wherein the vector is a plasmid.

13. A mammalian cell comprising the vector of claim 7.

14. A mammalian cell of claim 13, wherein the mammalian cell a COS-7 cell.

15. A mammalian cell of claim 13, wherein the cell is a 293 human embryonic kidney cell.

16. A vector of claim 10, wherein the vector is a baculovirus.

17. A baculovirus designated hY5-BB3 (ATCC Accession No. VR-2520).

18. An insect cell comprising the vector of claim 16.

19. A mammalian cell of claim 13, wherein the mammalian cell is a NIH-3T3 cell or a LM(tk−) cell.

20. The NIH-3T3 cell designated N-hY5-8 (ATCC Accession No. CRL-11994).

21. The LM(tk−) cell designated L-hY5-7 (ATCC Accession No. CRL-11995).

22. A membrane preparation isolated from the cell of claim 13 or 18.

* * * * *